US012662919B2

(12) United States Patent
Smith

(10) Patent No.: US 12,662,919 B2
(45) Date of Patent: Jun. 23, 2026

(54) CHARACTERIZING GEOLOGIC AREAS BASED ON COMPARATIVE COMPOSITIONAL ANALYSIS

(71) Applicant: Advanced Hydrocarbon Stratigraphy, Inc., Tulsa, OK (US)

(72) Inventor: Christopher Smith, Midland, TX (US)

(73) Assignee: Advanced Hydrocarbon Stratigraphy, Inc., Tulsa, OK (US)

( * ) Notice: Subject to any disclaimer, the term of this patent is extended or adjusted under 35 U.S.C. 154(b) by 829 days.

(21) Appl. No.: 17/887,507

(22) Filed: Aug. 14, 2022

(65) Prior Publication Data

US 2023/0175369 A1 Jun. 8, 2023

Related U.S. Application Data

(63) Continuation-in-part of application No. PCT/US2021/018075, filed on Feb. 14, 2021.

(Continued)

(51) Int. Cl.
*E21B 43/26* (2006.01)
*E21B 43/30* (2006.01)

(Continued)

(52) U.S. Cl.
CPC .............. *E21B 43/26* (2013.01); *E21B 43/30* (2013.01); *G01N 33/241* (2013.01); *G01N 33/2823* (2013.01)

(58) Field of Classification Search
CPC ........ E21B 43/26; E21B 43/30; E21B 49/005; E21B 49/08; G01N 33/241; G01N 33/2823; G01N 2030/065
See application file for complete search history.

(56) References Cited

U.S. PATENT DOCUMENTS 4,495,414 A 1/1985 Barrie
4,525,328 A 6/1985 Bredeweg
(Continued)

FOREIGN PATENT DOCUMENTS

BR 112019011944 4/2023
CA 2068012 12/1992
(Continued)

OTHER PUBLICATIONS

Clarkson, Jul. 2017. "Use of In-Situ Fluid Heterogeneity Characterization and Flowback Fluid Compositions to Constrain Fracture Height Growth and EOR Modeling in Liquid-Rich Low-Permeability Reservoirs" In Unconventional Resources Technology Conference.
(Continued)

*Primary Examiner* — Catherine T. Rastovski
*Assistant Examiner* — Brian Butler Geiss
(74) *Attorney, Agent, or Firm* — Transformative Legal; Len S. Smith

(57) ABSTRACT

The invention disclosed herein provides methods for analyzing oil production properties of an oil well. Methods comprise comparing characteristics of one or more samples of solid material (e.g., petroleum cuttings) or fluids with a produced fluid. Comparative analyses can occur between samples collected within a single well or across two or more wells. Select compounds, such as hydrocarbons, and select relationship(s) between compounds such as ratios of directly measured compounds or, e.g., classes thereof, are typically used in the methods; select methods (e.g., gentle volatiles extraction) are typically used to derive the compounds; or both. In a first exemplary application, methods herein are used to identify locations of relatively higher likelihood of petroleum productivity within a well. In a second exemplary (Continued)

application, methods are used to identify the likelihood of shared source locations (provenance) between oil samples.

29 Claims, 7 Drawing Sheets

Related U.S. Application Data

(60) Provisional application No. 62/977,677, filed on Feb. 17, 2020, provisional application No. 62/977,139, filed on Feb. 14, 2020, provisional application No. 62/977,116, filed on Feb. 14, 2020.

(51) Int. Cl.

| | | |
|---|---|---|
| G01N 33/24 | (2006.01) | |
| G01N 33/28 | (2006.01) | |

(56) References Cited

U.S. PATENT DOCUMENTS

| | | | |
|---|---|---|---|
| 4,797,906 | A | 1/1989 | Smith |
| 4,960,567 | A | 10/1990 | Smith |
| 5,241,859 | A | 9/1993 | Smith |
| 5,286,651 | A | 2/1994 | Smith |
| 5,328,849 | A | 7/1994 | Smith |
| 5,341,859 | A | 8/1994 | Howseman, Jr. |
| 5,411,707 | A | 5/1995 | Hiatt |
| 5,416,024 | A | 5/1995 | Smith |
| 5,447,556 | A | 9/1995 | Pleil |
| 5,457,316 | A | 10/1995 | Cohen |
| 5,767,399 | A | 6/1998 | Smith |
| 6,511,707 | B1 | 1/2003 | MacDonald |
| 6,541,272 | B1 | 4/2003 | Mitra |
| 6,661,000 | B2 | 12/2003 | Smith |
| 6,743,397 | B1 | 6/2004 | Zesiger |
| 7,210,342 | B1 | 5/2007 | Sterner |
| 7,395,691 | B2 | 7/2008 | Sterner |
| 8,256,282 | B2 | 9/2012 | Schlachter |
| 8,536,524 | B2 | 9/2013 | Pomerantz |
| 10,585,078 | B1 | 3/2020 | Liu |
| 10,760,418 | B1 | 9/2020 | Liu |
| 11,624,738 | B1 | 4/2023 | Liu |
| 11,774,417 | B1 | 10/2023 | Liu |
| 2001/0015093 | A1 | 8/2001 | Kempe |
| 2002/0194896 | A1 | 12/2002 | Stolper |
| 2004/0099804 | A1 | 5/2004 | Liu |
| 2005/0109207 | A1 | 5/2005 | Olander |
| 2005/0194134 | A1 | 9/2005 | McGregor |
| 2010/0277724 | A1 | 11/2010 | Bounouar |
| 2011/0297370 | A1 | 12/2011 | Michael |
| 2011/0305309 | A1 | 12/2011 | Brown |
| 2012/0167786 | A1 | 7/2012 | Laugharn, Jr. |
| 2012/0186331 | A1 | 7/2012 | Tipler |
| 2014/0026638 | A1 | 1/2014 | Bowers, II |
| 2014/0220700 | A1 | 8/2014 | Alexander |
| 2014/0283580 | A1 | 9/2014 | Rouchon |
| 2015/0123670 | A1 | 5/2015 | Robbat, Jr. |
| 2015/0155150 | A1 | 6/2015 | Bateman |
| 2015/0167052 | A1 | 6/2015 | Griffin |
| 2015/0346179 | A1 | 12/2015 | Pillot |
| 2016/0146970 | A1 | 5/2016 | Banas |
| 2016/0222781 | A1 | 8/2016 | Lawson |
| 2018/0306031 | A1 | 10/2018 | Smith |
| 2018/0313807 | A1 | 11/2018 | Michael |

FOREIGN PATENT DOCUMENTS

| | | |
|---|---|---|
| CN | 1609586 | 4/2005 |
| CN | 201740685 U | 2/2011 |
| CN | 104407089 | 3/2015 |
| EP | 0414564 B1 | 10/1995 |
| WO | WO2003050844 | 6/2003 |
| WO | WO2011077271 | 6/2011 |
| WO | WO2015050832 | 4/2015 |
| WO | WO2016186689 | 11/2016 |
| WO | WO2018111945 | 6/2018 |
| WO | WO2019178418 | 9/2019 |
| WO | WO2021163658 | 8/2021 |

OTHER PUBLICATIONS

International Search Report and Written Opinion relating to PCT/US2021/18075 mailed May 3, 2021.

Non-Final Office Action on May 17, 2018 for U.S. Appl. No. 15/908,760.

Extended European Search Report on Jul. 30, 2020 for EP178808861.

Indian Examination Report on May 16, 2021 for IN2019170221802.

International Search Report on Apr. 6, 2018 for PCT/US2017/065921.

Jorge et al. "Analysis of Volatiles in Fluid Inclusionc by Direction online Crushing Mass Spectrometry." Journal of Brazilian Chem Society 22.3, 2011: 43-455, p. 445, vol. 1 [online]. http://www.scielo.br/pdf/jbchs/v22n3a05.ped Published Oct. 19, 2010.

Mazidi et al. "Measurement of Uniaxial Compressive Strength of Rocks Using Reconstructed Cores from Rock Cuttings." Journal of Petroleum Science and Engineering 86-87 (Mar. 2012): 39-43.

McCarthy et al. "Basic Petroleum Geochemistry for Source Rock Evaluation." Oilfield Review, 23.2, Summer 2011.

Non-Final Office Action on Oct. 9, 2018 for U.S. Appl. No. 16/019,523.

Final Office Action on May 2, 2019 for U.S. Appl. No. 16/019,523.

European Examination Report on Feb. 27, 2023 for EP178808861.

Russian Office Action on Aug. 19, 2020 for EA201991461.

Non-Final Office Action on Oct. 9, 2018 for U.S. Appl. No. 16/019,529.

International Search Report and Written Opinion on Aug. 5, 2019 for PCT/US2019/22362.

CHARACTERIZING GEOLOGIC AREAS BASED ON COMPARATIVE COMPOSITIONAL ANALYSIS

CROSS REFERENCE TO RELATED APPLICATIONS

This Application is a continuation-in-part of PCT Application PCT/US21/18075, filed Feb. 14, 2021, which claims priority to U.S. Provisional Patent Application No. 62/977, 677, filed Feb. 17, 2020, U.S. Provisional Patent Application No. 62/977,139, filed Feb. 14, 2020, and U.S. Provisional Patent Application No. 62/977,116, filed Feb. 14, 2020, all of which are hereby incorporated herein by reference in their entirety.

FIELD OF THE INVENTION

The present invention relates to the characterization of geologic areas, such as oil wells. A primary aspect of the invention relates to the analysis of the oil producing properties of oil wells, including the oil producing properties of a single well.

BACKGROUND

Sophisticated and expensive technology is used by the petroleum industry to locate and evaluate economically viable petroleum deposits in geological units such as, e.g., formations (oil and gas "pay zones"). The high cost of oil exploration and extraction has driven the development of devices and methods aimed at improving the efficiency of oil exploration endeavors through characterizing samples of materials obtained from oil wells.

Oil wells can generally be characterized as either vertical wells or lateral wells, depending on the predominate direction of the productive portion of the well. In either case, wells are primarily formed by drilling through rock using various types of drills to form a borehole. In the process of drilling the borehole, drill cuttings are formed, which are ultimately brought to the surface, usually in drilling fluids called "muds." Muds are typically classified as either water-based mud (WBM) or oil-based mud (OBM). WBMs are typically a homogeneous blend of water and one or more clays, such as bentonite, and often including other performance-enhancing chemicals (e.g., potassium formate). OBM is usually an emulsion composed primarily of an oil-based continuous phase (comprising diesel, kerosene, fuel oil, mineral oil, or even crude oil) and an aqueous dispersed phase, which may optionally contain emulsifiers, wetting agents, or gelling agents. Oil-based muds have their own hydrocarbon signatures and often such signatures interfere with known analytical methods.

The type of rock in the geologic unit (a geologic unit being exemplified herein in exemplary aspects as a formation) and the relationship of the petroleum to the rock will often determine the production requirements and characteristics of a well. Increasingly production of oil from "tight rock" formations, such as formations predominately composed of shale, has become economically attractive. Tight rock typically is characterized on the basis of permeability. Typical tight hydrocarbon systems have permeabilities in the range of 1-10 millidarcies, whereas shales may be down to nanodarcies. In one aspect, tight rock can be characterized as having permeability of about 0.1 milliDarcy (mD) or less, with "very tight" rock characterized as having permeability of about 0.01 mD or less. As noted, some hydrocarbonbearing shale formations have permeability as low as 0.0001 mD, for example. In production from such "unconventional" wells, the use of fracking methods often enhances the amount of oil that is extracted.

Lateral wells and fracking methods are increasingly used in modern petroleum production. Lateral wells are commonly treated as being homogeneous in nature, due at least in part to limited existing technology available to sufficiently characterize such laterals. However, it is known that laterals are quite frequently heterogeneous. As the need to access tight formations via rock disaggregation (e.g., via the use of fracking) increases, and the use of unconventional drilling becomes more common, the impact on collected oil from geological characteristics of areas outside of the drilled bore, in lateral directions, have become of greater interest. For example, when fracking a well, there could be cracking of rock that occurs up to 50 feet, up to 100 feet, or even about 200 feet or more in one or more directions (e.g., circumferentially) from the well bore. Such cracking can create communication channels to other strata of rock beyond where a lateral might be drilled and such strata may have their own geological features, e.g., its own reservoirs, which, now having access to the wellbore, can contribute fluid/gas to the produced fluid/gas.

Identifying characteristics of well productivity, either in an operational well or in a predictive manner for a well yet to be brought online is an area of interest to those in the field. The ability to determine which areas of a well are contributing to well productivity and how those contributions change over time allows oil producers to make decisions about how to manage field operations. Further, the ability to predict which areas of a well yet to be completed will contribute most to the produced fluid/gas yielded by that well can save operators significant upfront costs, e.g., in determining which locations within the well warrant pipe placement, where landings might be positioned, what locations in the casing can be opened to allow flow of fluid/gas access to the well (e.g., which locations of the well can be completed with screens), or which areas may be amenable to fracking/well stimulation.

Existing technologies used to characterize production zones of oil wells, such as fiber optics, tracers, downhole fluid sampling, and, in certain cases, production logging, can be used to evaluate lateral wells but such technologies are subject to a number of performance limitations. Further, such technology is not applicable to predicting the production of new related wells and such methods often are prohibitively expensive.

Prior work contributed to the field by Dr. Michael P. Smith of Tulsa OK, USA, comprised analysis of drill cuttings capable of identifying and characterizing likely production zones of bore holes during an active drilling operation. Such characterization in real time provided actionable data with which drilling operators could direct drilling efforts. This technology is capable of identifying likely pay zones; however, like other technologies, typically did so by analysis only based upon the data that could be collected from rock from the specific geologic site impacted, such as cuttings formed by a well drill bit. Such art is described in, for example, International Patent Publication Nos. WO2018111945 and WO2019178418. This approach is helpful in characterizing production zones but does not tie that characterization back to a produced fluid/gas.

One way to identify relative contribution is by compositional analytical methods, which are sometimes referred to as "fingerprinting" methods. In such a method, a characteristic or set of characteristics is measured in both a produced fluid/gas (e.g., a whole oil) in addition to a series of samples representative of well material across the length of the well. The characteristic or set of characteristics is compared between each of the series of samples and the produced fluid/gas.

For example, Clarkson, 2017, "Use of In-Situ Fluid Heterogeneity Characterization and Flowback Fluid Compositions to Constrain Fracture Height Growth and EOR Modeling in Liquid-Rich Low-Permeability Reservoirs", in Unconventional Resources Technology Conference (URTec) (DOI 10.15530/urtec-2017-2691047), a continuation of an original study performed in 2016, describes a simple fingerprint style analysis comprising use of two of the more common molecules in the hydrocarbon system, methane and ethane, as a means of identifying relative vertical distribution of location-specific contribution to a final material. An isojar collection technique is used to collect cuttings samples, followed by analysis of the cuttings to obtain the gas composition of the cuttings, and finally the results compared to a produced fluid and correlated with where production within a well is likely coming from. Isojar compositions typically are composed of cuttings, water, and headspace gas, and the gas is analyzed by compositional gas chromatography and/or isotopic gas analysis (to prevent microbial degradation within the sample, bactericide is added to the cuttings sample within the isojar). A key limitation of the Clarkson 2017 method is the limited data set obtained by the method. More problematic in most cases is the fact that the method relies on the use of analytes (methane and ethane) that are easily influenced by rock: analyte interactions. Furthermore, the reliance on methane in this method is problematic because the compound is easily lost, introducing another source of assay error. While a bit less problematic, ethane is also very light and therefore subject to similar concerns.

US20110297370A1 (assigned to CONOCOPHILLIPS (herein referred to as the '370 publication), issued as U.S. Pat. No. 8,666,667) is one example of methods known in the art used to determine relative contribution of fluids associated with a geologic area. Methods of the '370 publication describe the relative contribution of fluid from each of a plurality of compartments to a final fluid. The '370 publication describes the determination of the contribution of multiple compartments to a final fluid with no consideration made to stratigraphy or the vertical or lateral orientation of a well, as the aims of the methods described therein do not require such precision. The '370 publication provides methods using fluids, which appear to be only liquid or gas in nature (exemplified primarily as mud gasses), such fluid compositions/profiles, including ratios of compounds within each fluid, compared one to another to determine relative contribution. The '370 publication provides a method that may be useful in scenarios wherein a vertical well is accessing multiple reservoirs ("reservoir compartments"). Co-mingled fluid and fluid from each compartment are separately analyzed. Results from the analysis of individual compartment fluid is compared to the analysis of the co-mingled sample, so that the relative contribution of each compartment of the multi-reservoir compartment area can be established. It may be possible that such a method is useful in larger field management. However, the method of the '370 publication is limited to the analysis of fluid samples and provides no method for having visibility as to the productivity or characteristics of a single geologic area, such as a single petroleum reservoir. As such, the method of the '370 publication is of limited utility.

US20180313807A1 (assigned to CONOCOPHILLIPS, subject to a recent USPTO notice of allowance, "the '807 publication") discloses a method for allocating production in reservoirs using a complex data set. The described gas fingerprints analyzed as part of the method disclosed in the '807 publication include carbon level, sulfur level, methane level, ethane level, propane level, butane level, pentane level and hydrogen sulfide level, each of which among others can be analyzed and fed into an automated numerical method engine wherein screening for the thousands of possible ratios (compounds and isotopes) is conducted to generate relative contribution information by stratigraphic interval of a well from which samples were collected. In view of these and other factors, the methods as described in the '807 publication are quite complex. A plurality of produced oil, produced water, and produced gas samples from unconventional reservoirs are collected over a period time. Rock samples are collected from the reservoir as well, and each sample is chemically fingerprinted using a broad range of technologies. Such data is then used to generate a number of reservoir maps over time, which are then used to optimize well placement within a reservoir. The process appears to primarily comprise obtaining a plurality of rock samples, a plurality of produced oil, produced water, and produced gas samples, which are each and all then chemically fingerprinted and assigned both a location and a time identifier, from which the allocation of production from one or more wells in relation to the time and location of fingerprints is deduced. Such complexity is not always warranted, can add additional costs and risks of errors, and is often inappropriate for the types of time-sensitive questions which may be pressing to operators seeking to work in "real time" or "near real time" operations.

Services/technology provided by RevoChem (described in limited fashion as of the date of this submission on RevoChem.com) and apparently described in U.S. Pat. No. 10,585,078 (herein the "'078 patent"), appear to be directed to improvements of the methods of the Conoco '807 publication. The '078 patent describes similarly the use petroleum well drill cuttings ("cuttings"), production fluid, or both to fingerprint production from different zones of wells, including unconventional wells. RevoChem describes the use of a far more data-intensive technique than even described in the '807 publication. The '078 patent describes method(s) capable of detecting the "thousands of naturally-occurring compounds existing in crude oil", reportedly fingerprinting samples based on "thousands of hydrocarbon compounds in one analysis" (web site), described in '078 as, " . . . well over 2000 compounds resolved in a typical crude oil GCXGC". In the '078 patent disclosed method, each one of these approximately 2000 compounds are either identified or assigned a "pseudo peak ID" and utilized in a comparative analysis across samples. The method is used to assess production zones and to track production over time. The '078 patent is unclear regarding exactly which compounds, e.g., hydrocarbon compounds, are analyzed, but examples appear to provide a description of samples collected from drilling operations using water-based bud; operations utilizing oil-based mud (OBM) are not described. The RevoChem methods described on both the RevoChem web site in the '078 patent would appear to be limited to use of cuttings and cores from wells drilled using water-based muds, as wells drilled using oil-based muds would provide interference in the provision of reliable results if heavier compounds (e.g., those above C12) we utilized. According to the RevoChem methods, samples are collected in intervals and over time (analyzing the performance of a well over time).

In both the Conoco '807 publication and the '078 patent to RevoChem, the approach for determining allocation utilizes a matching technique whereby compounds (including ratios of compounds) in produced oil are matched to compounds/ratios of compounds in rock samples. Upon identification of the ratio of compounds in a first rock sample and a second rock sample, such ratios are compared to a produced oil, and the application of linear mixing rules is utilized to determine relative contribution each rock is making to the total product. For such approaches to be applicable, contributing rock must have the same ratios of compounds as a produced oil in order assign contribution (e.g., in order to allocate relative contribution). In many scenarios, this is problematic, as in many cases, points along a well/borehole do not have exactly the same or even very similar composition as produced oil.

In addition, both the Conoco '807 publication and the '078 patent appear to fail to appreciate lateral heterogeneity in a well due to subsurface activity, such as, e.g., microbial activity. As an example, the '078 patent describes application of the method(s) utilizing samples collected over very wide intervals, e.g., 200-500 feet. In many scenarios, alterations (e.g., microbial alterations) in a resource are highly localized (e.g., can change significantly over the course of 100, 80, 60, 40 or 20 feet). Such localized alternations would be missed by such an analysis, both because it would fail to identify an endmember contribution and significant and variable alteration of the resource due to subsurface activity can occur (including but not limited to microbial activity and water washing effects), and because the wide sampling scheme would miss any compositional changing of a resource that may occur but be missed by such a sampling scheme.

Further, the applications described by the Conoco '807 and the '078 patent are related to the identification of relative contribution of locations within a well to a produced fluid (e.g., to a whole oil). Applicability of allocation methods beyond characterizing contributions to a whole oil are not contemplated.

As can be seen from the sophistication of the prior art, developed by scientists that have worked with some of the world's foremost oil production companies, new methods of characterizing the fluid characteristics of geologic areas will require significant inventive ingenuity. Surprisingly, several such methods are described here.

Principles of Construction, Terms, and Acronyms

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects, as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support any sub-groupings thereof, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "<" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/ suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10)" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/ step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/ collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~6%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most." or "mostly," means detectably ≥50% (e.g., mostly comprises, predominately includes, etc., mean ≥50%) (e.g., a system that mostly includes element X is composed of ≥50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤~25% of an element and terms such as "substantially free" of an element mean comprising ≤~5% of an element.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

Specific terms are used herein to describe elements and applications of the invention, but without limiting the scope of such terms as known in the art.

While the terms "well" and "borehole" can sometimes be used in common parlance distinguish mechanisms of drilling (e.g., a borehole typically drilled by machine and being small in diameter, a well typically being sunk by hand and being relatively larger in diameter), herein the two terms are used interchangeably to describe a vertical or horizontal shaft in the ground, commonly used herein to describe a petroleum well. The terms well or borehole should be interpreted as being applicable to petroleum wells, whereby either or both of oil and gas are produced. As used herein, the term well/borehole is a petroleum well (e.g., either an oil or a gas well), a carbon capture storage well, or a geothermal well. The term "well" as used herein is inclusive of producing and non-producing wells, online wells, wells not yet brought online, and dry (non-producing) wells (e.g., in aspects the methods herein can aid in the evaluation of, or determine, whether additional exploration/drilling of such a dry well should be considered, which can be indicated by cuttings from such a well sharing characteristics with that of nearby productive wells as determined by the application of the method(s)). The term "reservoir" is used to describe a geological formation or portion of a formation that includes sufficient porosity and permeability to store and transmit fluid, primarily oil, or, in aspects, a gas such as carbon dioxide. The term "compartment" is used to describe a geological area effectively sealed off from another, with little to no fluid communication occurring between two or more compartments. The phrases "well/borehole" or "reservoir/compartment" are used to reflect that either of such terms applies.

SUMMARY OF THE INVENTION

The invention described herein provides new methods for analyzing geologic areas. In particular aspects, the methods described herein relate to determining the characteristics of relatively large bodies of fluids contained in geologic areas (e.g., water-associated fluids in a geologic area with geothermal activity or an area associated with carbon sequestration applications). In aspects, methods relate to the oil production properties of at least one well, e.g., petroleum (e.g., oil) well, including the characteristics of individual petroleum reservoirs. Much of the description herein focuses on the application of the methods of the invention to petroleum well/reservoir characterization and the identification of source locations for fluid produced by a well, but skilled persons will recognize that such methods can be extended to other aspects (e.g., those exemplified above in this paragraph). There are several aspects of the invention, which can be combined in any suitable manner unless explicitly stated or clearly contradicted.

As indicated, the invention described herein further provides new methods for analyzing the status of carbon capture and storage efforts, such that the methods herein not only find applicability in allocating relative contribution of specific locations within a well to a final produced fluid, but can also be applied to carbon capture and storage applications to determine that such carbon capture and storage reservoirs, for example, remain appropriately sealed and are not detectibly or significantly leaking stored carbon dioxide.

The invention described herein yet further provides new methods for analyzing and establishing the migration volume of enhanced oil recovery ("EOR") carbon dioxide and has relevance in mapping geothermal reservoirs.

In aspects, the invention herein provides method(s) for determining the relative contributions of specific locations within a well, e.g., a horizontal oil well, to a final produced fluid while accounting for the lateral heterogeneity that can occur across or within a borehole/well. In certain aspects, such spatially identified allocation to a produced fluid is within a single well. In certain aspects, the invention provides methods to identify relative contribution of specific locations within a single reservoir, e.g., within a single compartment. In certain aspects, the invention provides methods of identifying compartment boundaries within a single well. In certain aspects, the method(s) of the invention comprise(s) the identification of fluids from multiple compartments and is capable of allocating the relative contribution to a final produced fluid of the location within a well providing fluid from such compartments. In particular aspects, the methods described herein relate to determining the source, sometimes referred to herein as "provenance" of fluid(s) contributing to a produced material from a given well. In aspects, methods of the invention can be applied to horizontal wells. In aspects, inventive methods can be applied to vertical wells (vertical workflows).

In aspects, the invention herein provides method(s) for determining presence of leaks in carbon capture and storage applications. In aspects, the method(s) of the invention are applied to the identification of locations at which carbon dioxide may be leaking from a carbon capture and storage reservoir. In aspects, the invention herein provides method(s) for establishing the migration volume of enhanced oil recovery (EOR)-related carbon dioxide. In aspects, the invention herein provides methods which find applicability in mapping geothermal reservoirs. In aspects the methods can be applied to differing applications simply based upon the election of compound(s) analyzed, methods of making such election of compounds being described elsewhere herein.

According to certain aspects, the method first comprises measuring the amount of at least one first compound component, such as, e.g., a single compound or, e.g., multiple compounds, such compound(s) being either organic or inorganic in nature (such compounds defined elsewhere herein) in a first sample fluid, such a fluid, in some aspects, at least substantially comprising a liquid (and typically primarily comprising, being generally composed of—i.e., being at least about 80% composed of, substantially consisting of, consisting essentially of, or consisting entirely of a liquid), wherein the sample comprises either a formation liquid (i.e., a fluid found in the geological formation in which the subject oil well is located, such as production oil) or a liquid that has been in contact with a formation liquid under conditions sufficient to transfer a detectable amount of the at least one compound, if present, to the liquid sample. In certain alternative aspects, the first sample fluid can be a gas, such as, for example, in applications wherein the method(s) herein is used in the characterization or monitoring of carbon capture and storage, and the aim is to detect leaking of CO2 from such storage reservoirs. In such aspects, the initial fluid can be carbon dioxide gas. Further, the fluid can be carbon dioxide in applications such as, e.g., enhanced oil recovery whereby carbon dioxide is injected into a well in an effort to increase petroleum production and the monitoring and/or tracking of such carbon dioxide is desired. The method further comprises measuring the amount of at least one compound, the at least one compound being the same or related to compound(s) measured in the first sample, which again can be an inorganic or organic compound, in at least a second sample comprising, typically at least primarily comprising, a related rock sample, wherein the second sample compound(s) is/are extracted from the second sample by, in aspects, subjecting the at least second sample to gentle volatiles extraction ("gentle extraction"). Herein, disclosure directed to methods or steps of a method applied to a second sample should be interpreted as also being applicable to that of any additional (e.g., subsequently analyzed) sample(s), such as, e.g., third, fourth, fifth, tenth, fiftieth, one hundredth, or one thousandth, etc. samples analyzed. The comparison of the compound(s) of the first sample (first sample compound(s)) with the same or related compound(s) of the second (or additional) sample(s), provides information concerning the likelihood of oil being present or in the area of the well, e.g., oil well. In aspects, the comparison is a direct compound-to-compound comparison between samples. In aspects, the method comprises first determining the ratio of two or more compounds within each sample. In aspects, the method comprises comparing one or more ratios of compounds in the first sample to one or more rations is the second (or additional) sample(s). In aspects, the comparison of the ratio(s) of compounds in the first sample (first sample compound ratio(s)) with the same or related compound ratio(s) in the second or additional sample(s) provides information concerning the likelihood of oil being present in or the area of the well, e.g., oil.

A "related" rock sample (or, alternatively, one can describe the relationship between the rock sample and the fluid sample as the fluid sample being a "related" fluid sample to the rock sample) is used here to describe a sample that is sufficiently related by, for example, location. In aspects, related samples (e.g., related fluid/rock samples) can be samples from the same region or area of oil exploration or, e.g., specifically the same site. In common aspects, related fluid/rock samples are samples collected from the same site, e.g., having been obtained from the same petroleum well (sometimes referred to as a borehole). In aspects, related fluid/rock samples comprise rock samples from a first borehole and a fluid sample from a different, second borehole within the same region or area of oil exploration (e.g., from within the same geologic unit), believed and/or otherwise known to be a sufficient analogue for, e.g., in aspects, oil or gas produced from the petroleum well from which the rock samples were collected. In aspects, a "related rock sample" or a "related fluid sample" is a sample having sufficiently similar characteristics as rock and fluid samples collected from an area/site of study, such that utilization of such related samples does not detectibly or significantly alter the final results, final interpretation of results, or both, from those obtained if such rock and fluid samples were actually collected from the same site, e.g., both liquid and solid samples of the same petroleum well were utilized in the method.

Typically, methods of the invention are performed using multiple samples from one or more geologic sites, such as one or more geologic sites within a geologic unit, and from one or more locations within such one or more sites. Site(s) can be any suitable type of geologic site(s). In aspects, a site is an active petroleum well or an area of petroleum exploration (a potential well site). Wells can be traditional vertical wells, lateral wells, or comprise aspects of both types of wells. In aspects, methods comprise application of such methods to vertical wells and/or lateral wells. As described herein, any suitable number of samples can be provided (or collected) in performance of such multi-sample methods. In aspects, at least about 10 samples, e.g., at least about 25 samples, at least about 50 samples, at least about 80 samples, or at least about 100 samples are subjected to analysis. In aspects, more than 100 samples, such as at least about 150 samples, at least about 200 samples, at least about 250 samples, at least about 300 samples, at least about 400 samples, at least about 500 samples or more, such as at least about 1000 samples, at least about 1500 samples, at least about 2000 samples or more are subjected to analysis.

In aspects, samples can be obtained from any suitable location within one or more sites. In aspects, samples are collected from one site, e.g., a single geologic site, such as, e.g., a well. In other aspects, as exemplified below, samples are obtained from multiple sites which are related such that use of samples from multiple sites is appropriate, e.g., a site which is located within the same region or area (e.g., geologic unit) of exploration, such as the same geological structure under analysis. Within a site, samples can be obtained from any suitable number of locations. In aspects, samples are obtained from at least about 10 separate locations in a site, such as from at least about 10 separate locations within a well. In aspects, samples are obtained from at least about 10 separate locations within an area containing multiple sites, from at least about 10 separate locations within a geologic unit, or from at least about 10 separate locations within any other suitable geologic unit, or from some combination thereof. For example, in aspects, a plurality of samples is collected from a single geologic site, e.g., a single well. In aspects, a plurality of samples is collected from a plurality of geologic sites within a single geologic unit. In aspects, single samples are collected from two or more geologic sites within the same geologic unit. In aspects, a single sample is collected from one geologic site and multiple samples are collected from a second geologic site within the same geologic unit. Such examples should not be viewed as limiting but rather exemplary types of the methods described herein. In aspects, most, generally all, or all samples analyzed in the method of at least one type of material, or both types of material (solid and liquid) are from parts of a site/area that are separated by no more than 120 feet, e.g., no more than 100, no more than 90, e.g., 10-100, 15-90, 15-85, or 20-80 feet, in at least one, at least two, or all directions from at least one or more other analyzed sample(s).

A "formation" is understood in the art to mean an identified area of strata having similar lithology. In some cases, a formation also may be defined by other characteristics, such as biostratigraphic characteristics, chemostratigraphic characteristics, or both, and sometimes such characterizations of a formation are used interchangeably. Typically, a formation is a series of strata/beds that is distinct from other beds above and below and is thick enough to be shown on the geological maps that are widely used within the area in question. Formations dominated by a rock typically include the dominant rock in the formation's name (e.g., the "Woodford Shale Formation" found in several parts of Oklahoma). However, formations in some cases can contain a variety of related or interlayered rock types, such as the Summerville Formation of Utah, which consists of thin alternating beds of shale, siltstone, and sandstone. Formations can be divided into sub-formations or "members" based on such characteristics.

A "source" is understood in the art to mean an identified area of strata (typically associated with petroleum or other hydrocarbon-associated compositions), which can be identified by characterization of biological markers or isotopes, stratigraphic positioning, or high gamma rays. The term "source" herein is understood as encompassing or referring to the known term "source rock" and "sources" represent a type formation, as defined elsewhere herein. An exemplary nonlimiting example of a source could include the "Woodford Shale Formation" found in several parts of Oklahoma. Unless contradicted, references to formations herein can be interpreted as referring to a source or source rock.

In petroleum production, the term "play" is used to indicate a region defined by a group of oil fields (each comprising many wells/sites) that generally share the same set of geological circumstances (e.g., formations present). Oklahoma, USA, for example, has many plays but two notable ones making headlines across the nation are the "SCOOP" (South Central Oklahoma Oil Province) and the "STACK" (Sooner Trend Anadarko Basin Canadian and Kingfisher Counties). The petroleum-rich STACK play is characterized by presence of Oswego, Meramec, Osage, and Woodford formations. Plays can be divided into "regions" or "areas" comprising two or more (often several) sites, potential sites, or both.

A typical "site" is a well, e.g., petroleum well, or an area of prospective petroleum drilling within an area or play. In aspects, related samples can be obtained from multiple sites within a single play. The term "geologic unit" is used to refer to any discrete geologic area from which suitable samples are obtained for use in the methods herein. For example, a geologic unit can comprise a portion of one or more formations. In certain aspects, herein, use of the term "geologic unit" can refer to or encompass a specific geologic site or any discrete geologic area from which suitable samples are obtained for use in the methods herein, such as, e.g., a specific well.

In aspects, a geologic unit, e.g., comprising one or more geologic sites, e.g., petroleum well(s), or a single geologic site, comprises many distinct locations that can be characterized based on vertical depth and lateral/lengthwise distance. Typically, samples are provided from (or collected from) more than 10 separate locations, such as at least about 20, at least about 30, at least about 40, at least about 50, at least about 65, at least about 75, or at least about 100 locations. In aspects, samples are provided from more than 100 locations, such as at least about 125, at least about 150, at least about 200, at least about 250, or more different locations in a site. The samples can be of any nature that includes an analyzable amount of rock material for the methods described herein.

In aspects, a "compound" as used herein can refer to an organic or inorganic compound. An "organic compound" encompassed by this term typically is any compound in which one or more atoms of carbon are covalently linked to atoms of other elements, most commonly hydrogen, oxygen, nitrogen, and often phosphorous or sulfur, with the exclusion of certain carbon-containing compounds that in the art are not characterized as organic compounds (e.g., certain carbides, carbonates, and cyanides). An organic compound used in the methods herein can be a hydrocarbon (containing only carbon and hydrogen) and in aspects can be a saturated hydrocarbon (often referred to as an alkane) such as, e.g., butane, pentane, hexane, heptane, octane, nonane, decane, undecane, or dodecane, but the methods herein are not necessarily limited to the use of hydrocarbons. In aspects, some, most, generally all, or all of the compounds in the comparative analysis are hydrocarbons. In aspects, the term "compound" includes one or more cycloalkanes. In aspects, an inorganic compound encompassed by the use of the term "compound" indicates compounds which can be but may not necessarily be structurally similar, compositionally similar, or both structurally and compositionally similar to the organic compounds suitable for use in the methods herein. In aspects, the inorganic compounds include a hydrogen; in some aspects the inorganic compounds lack a hydrogen.

Inorganic compounds can lack carbon, include carbon-containing compounds not characterized as organic compounds in the art, or both. Non-limiting examples of inorganic compounds suitable for use in the method(s) herein and encompassed by use of the term "compound" include carbon dioxide ($CO_2$), carbonyl sulfide (COS), carbon disulfide ($CS_2$), sulfur dioxide ($SO_2$), and hydrogen sulfide ($H_2S$). In aspects, the term "compound" encompasses such organic and inorganic compound and further encompasses what are defined as "related compound" as defined herein. Uncontradicted, in certain aspects, reference to the comparison of a compound as a step of a method described herein (e.g., the comparison of a compound measured in a first sample to the same or related compound measured in a second or additional sample) can be interpreted as the comparison of a ratio containing that compound.

The "related compounds" of the second, or at least second, sample can also be referred to as "identical or similar compounds" (IOSCs). An IOSC is a compound that is identical to the compound in the first sample, e.g., hexane (a C6 alkane) and hexane, or that is sufficiently similar to the compound of the first sample so as to still provide an indication, typically a detectibly or significantly improved indication, as to the likelihood of oil in the well, e.g., hexane and cyclohexane (a C6 cycloalkane). Such a definition is similarly applicable to IOSCs of inorganic compound(s) which are measured in the first sample.

In aspects, one, some, most, or all of the similar second (or additional) sample compounds are compounds that can be characterized as compositionally similar compound(s) (CSCs), which can include but may not necessarily include carbon compositionally similar compound(s) ("CCSC(s)," as not all compounds suitable for use within the methods herein comprise carbon, such as, e.g., $H_2S$. A compositionally similar compound (CSC) is a compound sharing the same molecular composition, such as, e.g., hydrogen and sulfur in the case of use of the compound $H_2S$. A carbon compositionally similar compound (CCSC) is a compound that has within +/−0-3 carbon atoms (carbons) of one or more referenced first sample comparator compound(s). Typically, a CCSC has within +/−0-2 carbons or +/−0-1 carbons. CCSCs can have similar or different structures than the comparator first sample compound (e.g., a first sample compound that is a linear hydrocarbon can be in aspects compared to a cyclic hydrocarbon second (or at least second) sample comparator compound having +/−0-2 carbons from the linear hydrocarbon, though this definition need not apply only to linear hydrocarbons).

In aspects, one, some, most, or all of the similar second or additional sample compounds is/are characterizable as structurally similar compounds (SSC(s)). An SSC is a compound that has both a similar (but not identical) composition, for example carbon composition content and similar structure as a referenced compound (e.g., in terms of inclusion or lack of cyclic structures, double or triple bonds, inclusion of aromatic rings, inclusion of heteroatoms, or any combination thereof). In aspects, one, some, most, or all of the SSCs are isomers of the comparator first sample compound(s). In aspects, the term "compound" includes organic compounds, inorganic compounds, and any such IOSCs, including CSCs, CCSCs or SSCs thereof.

In aspects, at least one, some, most, or all of the 2nd sample comparator compounds are structurally different from corresponding/compared first sample compounds. In aspects, structurally different compounds comprise similar carbon compositions. E.g., in aspects, methyl cyclopentane in the 1st or 2nd sample is compared to hexane in the other sample. In aspects, a 1st or 2nd sample refers to a 1st or 2nd type of sample, comprising multiple samples. E.g., in aspects, methods comprise analyzing multiple solid samples (of a solid sample type) and a liquid sample. As noted, uncontradicted, references to single and plural elements are considered interchangeable, as this particular example illustrates.

In aspects, one, some, most, substantially all, or all of the compounds analyzed in methods described herein in a second or additional sample(s) are identical to first sample compounds.

According to certain aspects, there are less than about 120, e.g., less than about 100, or less than about 80 suitable compounds for use in this invention (e.g., about 1-120, 2-120, 1-100, 2-100, 2-80, 2-60, 3-60, 3-90, 3-120, 4-80, 4-100, 4-120, 5-125, 5-100, 5-75, 5-50, 5-25, 4-40, 4-20, 3-60, or 3-30 compounds are included in an analysis). In aspects, most, generally all, or all of such compounds are hydrocarbons; however, the methods herein are not restricted to the use of mostly or entirely hydrocarbon compounds.

In aspects, a second sample (and, e.g., any additionally analyzed sample(s)) will comprise, primarily comprise, or consist of sample material(s) that are related to the first sample. A "related" second or additional sample means a sample from a source that provides compounds that significantly increase the likelihood of predicting the presence of oil in the geologic site, e.g., well, by comparison of the first sample compounds and second sample compounds. In one aspect, the second sample comprises a suitable amount of solid material, e.g., rock, obtained from the same geological unit, e.g., the same site, such as the same petroleum well as the fluid. In aspects, the at least second sample comprises solid material, e.g., rock, from a corresponding portion of a geologic unit.

In typical aspects, some, most, generally all, or all of the compounds extracted from the at least second sample are extracted by (among other things) gentle vacuum extraction, or are primarily, substantially only, essentially, or entirely extracted by gentle extraction methods. "Gentle vacuum extraction" methods are described in International Patent Application Nos. WO2019178418 ('418), U.S. Pat. No. 10,494,919 ('919), and International Patent Application PCT/US20/13261, each of which being hereby incorporated by reference herein in its respective entirety. In one aspect, a gentle extraction means application of, among other things, a vacuum with a pressure of about $1 \times 10$-2 millibars or less at room temperature applied for about 3-30, 4-24, 5-20, or 5-15 minutes. Any of the methods described in the '418 application or '919 patent as being suitable for extraction of rock volatiles can be used in such methods of this invention. Any alternative method that extracts a significantly similar amount of the compounds extracted by gentle vacuum extraction methods also or alternatively can be employed in such aspects. In aspects, compounds are extracted by application of two different pressures (two aliquot methods) as described in the '418 application or '919 patent.

The method can then further comprise comparing the amounts of the similar compounds in a second sample, and, in aspects, one or more additional sample(s), to corresponding first sample compounds. In aspects, such comparison step(s) comprise calculating one or more ratios if more than one pair of corresponding first sample and second sample (and additional sample(s) as applicable) compounds is identified and measured. Such methods are exemplified below.

In aspects, the disclosure herein describes a method for analyzing the oil production properties of an oil well-associated geologic unit. In aspects, such a well-associated geologic unit can be, e.g., a formation. In certain aspects, the method first comprises measuring the amount of at least one first compound component of a first fluid sample, in aspects such a first fluid sample is a gas and in alternative aspects such a first fluid sample is a sample substantially comprising a liquid (e.g., generally being composed of a liquid, substantially consisting of a liquid, or consisting essentially of a liquid), wherein the sample comprises either a formation fluid from a subject geologic site, e.g., well, or a corresponding portion of the geologic formation or a fluid that has been in contact with either such a formation fluid under conditions sufficient to transfer a detectable amount of the at least one compound, if present, to the fluid sample. Herein, in aspects, uncontradicted, disclosure directed specifically to a formation can be interpreted as more broadly applicable to a geologic unit. Further, the method can comprise measuring the amount of at least one compound having also been measured in the first sample in at least one second sample comprising a solid material, e.g., rock, obtained from the well or from a corresponding portion of the geologic unit, which one or more compounds is/are extracted from the second (or additional) sample(s) by subjecting the at least second sample to gentle volatiles extraction and analyzing the compounds extracted by application of the extraction. Finally, the method can comprise comparing the amount, which is typically considered as one or more ratios if more than one compound is measured, of the one or more compounds in the first sample to one or more compounds, e.g., which can be in aspects the same one or more compounds, different but somewhat similar compounds (e.g., a CSC, CCSC, SSC), or a combination thereof, in the one or more second samples to assess the oil production properties of the well.

In aspects, the disclosure herein describes methods of analyzing the oil production properties of one or more parts of a geologic site-associated geologic unit. In aspects, the geologic site is an oil well, such that the disclosure describes methods of analyzing the oil production properties of one or more parts of a well. Herein, "oil production properties" can comprise, e.g., locations or areas within a geologic site, e.g., well contributing material to a produced fluid, locations or areas within a geologic unit contributing material to a produced fluid, source location(s) of material contributing to a produced fluid, or any combination thereof. Therefore, herein, reference to "oil production properties" can, uncontradicted, be interpreted to encompass any one or more of such characteristics.

In certain aspects, the disclosure herein describes a method of analyzing the oil production properties of one or more parts of a well-associated geologic unit comprising determining the rock composition of the geologic unit comprising a subject well by obtaining a first fluid sample of a gas or of a fluid essentially comprised of a liquid, such fluid comprising either, e.g., a formation fluid from the subject well or from a corresponding portion of the geologic formation or a fluid that has been in contact with either such a formation fluid under conditions sufficient to transfer a detectable amount of the compounds, if present, to the sample and further obtaining one or more second solid samples that comprise rock material from the subject well or from a corresponding portion of the geologic unit. In some aspects the method further comprises measuring the amount of at least two organic compounds, each comprising at least four covalently bonded carbons, contained in a first sample, wherein the at least two organic compounds are compounds that: i) have the same number of carbon atoms as one another; ii) each have at least five covalently bound carbon atoms; iii) each have at least five covalently bound carbon atoms and further if each compound does not share the same number of carbon atoms, the difference in the number of carbon atoms between any two compounds is no greater than 2; iv) are not subject to interfering rock interactions with the rocks in the composition of the geologic unit in ways which are known to be significantly different from one another; or v) can be characterized in that any one or more of (i)-(iv) are true for the organic compounds. Yet further, the method can comprise measuring the amount of at least two of the same or similar (e.g., CSC, CCSC, SSC, or any combination thereof) compounds as measured for in the first sample in the one or more second solid samples, and finally comparing the amount, which is typically considered as one or more ratios if two or more compounds are measured, of the two or more compounds in the first sample to the two or more compounds of the at least second sample, wherein at least two of the two or more compounds of the at least second sample are the same or similar (e.g., CSC, CCSC, SSC, or a combination thereof) as those measured in the first sample to assess the oil production properties of the well. The method is typically limited to measuring less than about 20, less than about 15, less than about 12, and often less than about 10 compounds in the first and at least second samples. In aspects, one, some, most, or all of the compounds compared in the first and at least second sample(s) are selected based on, i.a., a low likelihood of compound loss (e.g., due to compound (e.g., hydrocarbon) interaction with rock from the geologic unit.

In aspects, use of the phrase "the same compound(s)" should be interpreted as being inclusive of two or more compounds being identical, or one or more compound(s) being a CSC, CCSC, SSC, or any combination thereof of the other(s).

In certain aspects, the disclosure herein describes a method of analyzing the oil production properties of an oil well comprising obtaining a first fluid sample substantially comprising a liquid that at least primarily comprises a formation liquid from the subject oil well or from a corresponding portion of the geologic unit, or a liquid that has been in contact with either such a formation liquid under conditions sufficient to transfer a detectable amount of the compounds, if present, to the liquid sample, and further obtaining a second one or more solid sample(s) that comprise rock material from the subject oil well or from a corresponding portion of the geologic unit. In certain aspects the first liquid sample comprises an oil-based mud, the second one or more solid sample(s) comprise(s) a rock that has been in contact with an oil-based mud (e.g., a rock sample that has been in contact with an OBM less than twenty-four hours before analysis), or the first sample comprises an oil-based mud and the second one or more solid sample(s) comprise(s) a rock that has been in contact with an oil-based mud prior to analysis (e.g., in contact with an OBM less than twenty-four hours before analysis). In some aspects the method further comprises measuring the amount of at least one compound in the first fluid sample, measuring the amount of at least one compound associated with the second one or more solid sample(s) wherein at least one compound is the same or similar (e.g., CSC, CCSC, SSC, or a combination thereof) as at least one compound measured in the first fluid sample, and using the resulting data to determine the oil production properties of the oil well by comparing the amount, which step/method often comprises one or more ratios of the first sample being compared one or more compound(s) to the amount of the one or more compound(s) in the second one or more sample(s).

According to certain specific aspects, the disclosure describes a method of evaluating the oil producing capability of at least one part of an oil well comprising collecting a first sample of a fluid essentially comprised of a liquid from the oil well or from a location that has been in contact with at least one part of the geologic unit within which the oil well has been placed under conditions permitting the transfer of a quantifiable amount of oil-associated compounds into the first liquid material, and further, collecting at least a second sample comprising rock from one or more locations in the at least one part of the well. The samples collected are, in some aspects of the method described, subjected to an analysis that identifies the approximate amount of about 2-50, 2-40, 2-30, 2-19, e.g., about 3-18, 3-12, or 3-9 compounds in the fluid, the compounds mostly, generally, or only consisting of C4-C11 hydrocarbons (hydrocarbons comprising between 4 and 11 carbon atoms), such as C4-C11 alkane and C4-C11 cycloalkane compounds. The resulting data can then, in aspects, be used to evaluate the oil producing capability of the at least one part of the well by comparing the amount of the measured compounds in the first sample to the amounts of the measured compounds in the at least second sample (which is typically considered as one or more ratios if two or more compounds are measured), wherein, in one facet, the presence of most or all of the measured compounds in both the first sample and the at least second sample is indicative of oil being associated with the at least one part of the well. In alternative embodiments, the more similar a profile obtained at a specific location is to the first sample, the more likely that position within a well is providing a higher contribution to the first sample.

In certain aspects, the disclosure herein describes a method for allocating a relative proportion of productivity to each interval of a plurality of intervals within a well, e.g., an oil well, comprising the collection of a sample of a fluid comprised substantially of a liquid that comprises either a formation liquid from the subject oil well or from a corresponding portion of the geologic unit or a liquid that has been in contact with either such a formation liquid under conditions sufficient to transfer a detectable amount of the compounds, if present, to the liquid sample; and further the collection of a series of non-liquid samples comprising rock from a plurality of locations of the well, e.g., an oil well. The method can then further comprise subjecting the liquid material to an analysis that identifies the approximate amount of about 2-120, 2-100, 2-80, 2-60, 2-40, 2-10, 3-90, 3-60, 3-30, 3-18, 3-9, 2-8, 3-8, 2-7, 3-7, 2-6, 3-6, 4-10, or about 4-8 compounds, wherein some, most, generally all, or all of such compounds are hydrocarbon compounds (also referred to as "species") in the liquid. Typically, some, most, substantially all, or all of such compounds in the first sample are C4-C11 hydrocarbons, e.g., alkane and cycloalkyl compounds. The method further comprises subjecting the series of non-liquid material samples to an analysis that identifies the approximate amount of similar chemical species (e.g., of at least 2 of the same or similar (e.g., CCSC, SSC, or both) chemical species, e.g., at least about 3, at least 4, at least 5, at least 6, at least 7, or at least about 8 of the same species, such as about 2-10 species, 3-9 species, or about 3-7 species). In aspects most, generally all, or all of such species consist of C4-C11 hydrocarbon compounds (e.g., corresponding alkane and cycloalkyl compounds). The method further can comprise determining the ratio between different structural classes of such compounds, such as between (i) the alkane and (ii) cycloalkyl compounds or the sum of total alkane and cycloalkyl compounds, the cycloalkyl compounds and alkane compounds having the same number of carbons within each of the fluid and series of non-liquid material samples (or a similar number of atoms, which may differ by e.g., one carbon, in the case of compounds having at least five carbons). In certain aspects, the ratio between isomers of the same class can be utilized, such as, in non-limiting examples, use of methylcylopentane and cyclohexane in ratio(s) (methylcyclopentane and cyclohexane both being C6 cycloalkanes), and 1,2 cis-dimethylcyclohexane versus 1,2 trans-dimethylcyclohexane (whereby both compounds are cycloalkanes as described herein but are isomers and may be considered different compounds). The method further can comprise determining the ratio between two or more groups or classes of compounds. In certain aspects the method further comprises dividing the well bore length into location intervals and combining the series of ratios calculated for each of the non-liquid material samples collected from within each of the defined intervals to establish an average or representative ratio for each of the previously defined intervals ("interval ratios"). Further, the method described can comprise assigning each interval ratio a weighting factor so as to assign each location interval within the well a weight representative of its overall spatial contribution to the total length of the well bore to establish a first set of representative bore hole interval values ("length-weighted interval ratios"). In aspects, interval assignment can be made by applying individual sample depths (e.g., such that an individual sample depth acts as the interval assignment in relation to those samples collected before and after it). In aspects, interval assignment can be made by calculating an average of samples across an interval. While possible and included as an aspect of the invention, such a physical averaging technique may, in certain aspects, not be preferable (or not performed). In certain aspects, physical averaging techniques are not applied. Further, the method can, in aspects, comprise applying a numerical method analysis to the collection of length-weighted interval ratios capable of iterating various combinations of applied weighting factors and comparing the results of such iterations to a target value, the target value being derived from the fluid sample, with the weighting factor as an adjustable variable. Further, the method can comprise identifying the combination of weighting factors, which, when applied to each interval ratio, results in a weighting of the bore intervals such that when all interval ratios are considered, the combination most closely represents the profile of the fluid sample. Finally, the method can, in aspects, comprise utilizing an identified/determined weighting to establish the relative proportion of productivity of each interval of the well to the fluid sample.

In some aspects, the disclosure herein describes methods of analyzing the oil production properties of a well, analyzing the oil production properties of an oil-associated geologic unit, analyzing the oil production properties of one or more parts of an oil well-associated geologic unit, allocating a relative proportion of productivity to each interval of a plurality of intervals within an oil well, and also or alternatively predicting the highest producing zones of yet-to-be completed oil wells. In aspects, the disclosure herein describes ascertaining the source of produced hydrocarbon fluid, e.g., liquid samples (e.g., their provenance). In aspects, for example, identifying that a plurality of oils produced from the same geologic sites, e.g., wells, had the same source, e.g., were sourced from an expulsion from the same source, e.g., the same source rock, at a similar point in time in terms of the maturation of the source rock; or, alternatively, identifying that a plurality of oils produced from the same geologic sites, e.g., wells, had differing sources, e.g., were not sourced from the same expulsion from the same source, or were not derived from a source at a similar point in time in terms of the maturation of a source rock. In aspects, the methods comprise the analysis of two different types of samples, one being a fluid and one being a non-liquid material, such as a sample comprising rock from a geologic unit, such as a petroleum drill cutting, such as a cutting delivered to the surface in an oil-based mud ("OBM"). In aspects, the methods comprise utilization of the sample analysis techniques in the SMITH Art (defined below) (e.g., application of gentle vacuum extraction, cryo-trapping of volatiles, and associated slow release through heating, and mass spectrometry quantification of compounds) to measure one or more compounds in the solid samples, the liquid sample(s), or both. In aspects, the fluid samples can primarily comprise, generally be composed of, or at least substantially consist of a formation fluid, such as a produced oil, and in other aspects includes a fluid that has been in contact with formation fluids, such as a flowback material or water. In aspects, the fluid sample can comprise a condensate. In some aspects of this and other methods of the invention fluid inclusion fluids are used in place of or in addition to formation fluid samples or formation fluid-contact samples as the liquid sample of the method. In other aspects, fluid inclusion fluids are excluded from the fluid sample, but in such methods the method can still comprise comparative analysis with fluid inclusion analytical methods, such as are described in the SMITH Art (defined below).

In aspects, the non-liquid, e.g., solid material, (second) samples can be petroleum well drill cutting(s) or petroleum well core sample(s) (e.g., one or more sidewall core(s)). In facets, the two different types of samples comprising rock material can be collected from the same geologic site, e.g., a well (and considered either parts of the second sample or two different rock-containing samples that are separately or together compared with the first sample). In aspects, the two different types of samples can be collected from different geologic sites, e.g., two different wells. In aspects, such disparate geologic sites can reside within the same geologic unit. In aspects, the compounds are organic compounds. In cases, the organic compounds are hydrocarbons. In facets, the organic compounds are mostly, generally, or only C4-C11 hydrocarbons. In aspects, the C4-C11 hydrocarbons are mostly, generally, or only alkanes or cycloalkanes. In some aspects, the C4-C11 hydrocarbons are CCSC(s), SSC(s), or both, of the organic compounds measured in the liquid sample. In other aspects, the methods comprise weighting directly measured values or calculated ratios such that when comparing such directly measured or calculated ratios between two different samples, one is weighted according to its relative spatial representation to the other.

In certain aspects, the disclosure herein describes methods of analyzing the oil production properties of a well, analyzing the oil production properties of an oil-associated geologic unit, analyzing the oil production properties of one or more parts of an oil well-associated geologic unit, allocating a relative proportion of productivity to each interval of a plurality of intervals within an oil well, and also or alternatively predicting the highest producing zones of yet-to-be completed oil wells which comprise utilization of numerical methods engines to perform iterative calculations in order to determine the relative contribution of each location or interval of a well to a fluid from, or a fluid representative of a fluid from, the well. According to certain aspects, methods herein can be applied and used to determine and implement an optimal completion strategy for a well not yet completed using known productivity information from sites within the same geological units (e.g., known productivity of the region or known productivity of a neighboring well). In aspects, produced fluid from a neighboring production site (e.g., a site within the same geological unit, e.g., a neighboring well) can be known. In aspects, the method comprises utilizing such known production fluid characteristics in combination with solid sample analysis from the yet-to-be completed well in the methods herein, such that the production zones of the not-yet-completed well can be predicted, and a plan for optimal completion of the well can be established before sampling produced fluid from that well. In aspects, methods herein can be applied when the oil production characteristics of a well. In some aspects the calculations are performed using data generated on rock samples using extraction and analysis techniques comprising gentle vacuum extraction (i.e., gentle extraction), cryogenic trapping and the associated controlled release of trapped compounds therefrom (as also described in the '919 US patent, '418 PCT application, and '261 PCT application), and mass spectrometry compound analysis (similarly described in the '919 patent, '261 application, and '418 application, all of which name Michael P. Smith of Tulsa, OK, USA, as inventor, which are also collectively referred to herein collectively as the "SMITH Art" or "SMITH Patent Documents"). In some aspects, the samples analyzed comprise samples sourced from wells drilled using oil-based mud drilling techniques.

In one aspect, the invention provides a method of using the amount of release resistant water, such as described in the '261 application, to similarly identify zones of relative production from a well, such as any of the wells described herein. In some aspects, such methods are performed independently of the other methods described herein. In some aspects, such methods are combined with the other methods described herein. Such a method typically comprises determining zones of relatively high and low release resistant water to identify expectedly high and low production zones for oil production. In one aspect, such methods comprise consideration of other real-world data, such as determined by other methods described herein, to assess the potential contributions of different zones.

In some aspects, the disclosure describes methods which, when applied to appropriate sample sets having a spatially meaningful distribution, such a spatially meaningful distribution being a distribution of samples from wells which are positioned both above and below a lateral (e.g., a lateral being fracked), are capable of establishing a two-dimensional, a three-dimensional, or both a 2-dimensional and 3-dimensional characterization ("map") (distribution, plot, etc.) of the relative contribution of various areas of a geological unit to a produced fluid.

In some aspects, the disclosure herein describes a method comprising analysis of alkanes and cycloalkanes of the C4 and higher range, e.g. C4-C11, and the comparison of absolute values of, or ratios calculated using, such chemical species, between one or more series of cuttings and a produced fluid (e.g., an oil or a liquid having been in, or in, contact with either such a formation liquid under conditions sufficient to transfer a detectable amount of the compounds, if present, to the fluid), such values either absolute or calculated ratios being weighted according to their relative spatial contribution to the length of a geologic site, e.g., a well, so as to determine which locations within an, e.g., a well, provide more or less contribution to the produced fluid composition. Careful selection and utilization of such hydrocarbons such as alkanes and cycloalkanes of the C6+ range by the methods disclosed herein, versus use of lighter hydrocarbons such as methane or ethane as disclosed by the prior art, helps to avoid the risks of data skewing as previously described. Further, the careful selection of such hydrocarbons allows for the derivation of actionable data regarding relative contribution of a plurality of well locations to a final produced fluid using far fewer datapoints than proposed by, e.g., RevoChem or similar or equivalent technologies or approaches, such as that disclosed in the, e.g., the '807 publication. In aspects, the disclosure herein describes methods which address the need for number of hydrocarbon species being measured for the types of characterization described herein to be cost effective. While the dataset resulting from analysis such as that described by RevoChem or as disclosed in the '807 publication is extensive, it is not always feasible or necessary to provide such a plethora of inputs in order to obtain reliable, actionable data. In some embodiments, the method can alternatively comprise the analysis of aromatic compounds. In some embodiments, the method can comprise differential analysis of branched hydrocarbons and linear alkane hydrocarbons, such that, for example, one of the ratios analyzed in the method can be between branched hydrocarbons and linear hydrocarbons of similar size. In other embodiments, normal alkanes (linear alkanes) and branched alkanes are grouped together in performing an analysis (such as in ratio comparisons). In some embodiments a method can incorporate analysis of hydrocarbons, e.g., saturated hydrocarbons (e.g., comparing hydrocarbons to hydrocarbons). In aspects, a method may utilize or be limited to aromatics. In aspects, the method may utilize or be limited to the use of cycloalkanes where suitable.

In some embodiments, the method comprises a step of determining if inclusion of certain compound(s) in the analysis is suitable by analyzing the rock characteristics of the geologic unit. For example, where a geologic unit comprises a high silica content or a high quartz content, such as at least about 5% quartz or more, the method can comprise a limited analysis (e.g., using few compounds, attributing less weighting given to results, or both), or exclusion of analysis aromatics in the method, as such compounds can have interactions with the rock from a geologic unit that raise a substantial risk of incorrect analysis.

In some aspects, the disclosure herein further or alternatively addresses the characterization of a potential pay zone within an oil well as described by the prior SMITH art, e.g., by incorporating the measurement of a fluid, the fluid being at least generally composed of or comprised essentially of, or stated another way, substantially consisting of, either a formation liquid or a liquid that has been in contact with a formation liquid under conditions sufficient to transfer a detectable amount of the at least one compound, if present, to the liquid sample, against which the analysis of a series of non-liquid samples (e.g., drill cuttings or core samples) can be compared. In aspects, from performing such a step, the relative contributions of a particular location or a particular zone within a well can be identified, and accordingly, likely pay zones can be identified by identifying areas with favorable contributions.

In aspects, the disclosure herein addresses the ability to incorporate oil-based mud samples (solid or liquid) into the evaluation of relative contribution of a plurality of locations within a geologic site, e.g., a well, to a produced fluid, oil-based muds being commonly employed in lateral well drilling and thus expanding beyond the prior art the ability to characterize lateral wells in addition to vertical wells. Such methods comprise the analysis of a fluid sample, e.g., a predominately liquid sample or an essentially entirely liquid sample, and a sample comprising one or more, typically many, solid material samples, comprising rock from a geologic unit, such as cuttings or core samples, and determining the presence of one or more, typically at least two or more, e.g., 2-10, 3-9, 2-8, or 3-7 compounds in each sample or sample collection, wherein the liquid sample, the solid sample(s), or both have been in contact with an oil-based mud, and comparing such compounds to determine the characteristics of the well (e.g., by comparing ratios of select compounds such as alkanes and cycloalkanes from each type of sample).

In another facet, the invention provides a method of comparatively analyzing a geologic unit comprising at least two oil wells, which comprises obtaining solid rock samples from the wells, obtaining release resistant water data for each of the wells, and comparing the release resistant water information. In one aspect, the overlap of favorable release resistant water characteristics in the two or more wells is used to identify one or more oil-rich zones. In other aspects, the relative poor performance of one or more wells in a region characterized by release resistant water analysis and relative good performance of one or more other wells in the region characterized by release resistant water analysis is used to identify favorable portions of the region for oil production. In one aspect, the wells are lateral wells, and the results are used to map favorable lateral zones in the geologic unit for petroleum production.

According to certain embodiments, the invention provides, a method of assigning a highly contributing source of produced hydrocarbon liquid samples. In aspects, the method comprises collecting a first sample of a fluid. In aspects, the fluid is essentially comprised of a fluid from a well, e.g., an oil well, or from a location known to be or have been in contact with at least one part of a geologic unit within which a well is located under conditions permitting the flow of a quantifiable amount of a number of oil-associated compounds into the first fluid material. In aspects, the method comprises collecting a sample of a second fluid establishing a second fluid sample. In aspects, the second fluid sample is collected from a location known to be or known to have been in contact with at least one part of the geologic unit within which the well has been placed under conditions permitting the flow of a quantifiable amount of a number of oil-associated compounds into the second fluid material. In aspects, the method comprises subjecting the first fluid sample to an analysis that identifies the approximate amount of 1-9 organic compound(s) in the fluid sample. In aspects, the 1-9 organic compound(s) are selected from a group of, e.g., less than about 120 possible organic compounds. In aspects, the method comprises subjecting the second fluid sample to an analysis that identifies the approximate amount of 1-9 organic compound(s) in the fluid sample. In aspects, the 1-9 organic compound(s) are selected from a group of, e.g., less than 120 possible organic compounds. In aspects, the method comprises evaluating the likelihood of the first fluid sample and second fluid sample originating from the same source. In aspects, the evaluation comprises comparing the amount of the measured compound(s) in the first fluid sample to the amounts of the measured corresponding carbon-compositionally similar and structurally similar organic compound(s) in the second fluid sample, wherein the greater presence of corresponding or structurally similar organic compounds in the second fluid sample with respect to organic compounds identified in the first sample increases the likelihood of the first fluid sample and the second fluid sample having the same source. In aspects, the evaluation comprises comparing ratio(s) of two or more measured compound(s) in the first fluid sample to the same or similar ratio(s) of the corresponding carbon-compositionally similar and structurally similar organic compound(s) in the second fluid sample, wherein the greater presence of corresponding or structurally similar organic compounds ratio(s) in the second fluid sample with respect to organic compounds ratio(s) identified in the first sample increases the likelihood of the first fluid sample and the second fluid sample originating from the same source. In aspects, the method comprises determining whether the comparison is sufficient to identify the characteristics of the first fluid material as being established by material contributed from the location at which the second sample was collected. In aspects, in the event the comparison is not sufficient to identify the characteristics of the first fluid sample as being contributed by fluid located at the location from which the second fluid sample was collected, is not sufficient to identify the characteristics of the first fluid sample as having originated from the same sources as the second fluid sample, or both, the method can comprise collecting one or more additional fluid samples from one or more location(s) that are or are known to have been in contact with at least one part of the geologic unit within which the geologic site is located, e.g., within which the well has been placed under conditions permitting the flow of a quantifiable amount of a number of oil-associated compounds into the one or more fluid samples. In aspects, the method comprises subjecting the one or more additional fluid samples to an analysis that identifies the approximate amount of 1-9 organic compound(s) in the one or more additional fluid samples, such as, e.g., 1-9 compound(s) selected from a group of less than about 120 possible organic compounds. In aspects, the method comprises evaluating the likelihood of the first fluid sample and the one or more additional samples having originated from the same source (e.g., having the same location of origin) by comparing the amount of the measured compound(s) or ratios thereof in the first fluid sample to the amounts of the measured corresponding carbon-compositionally similar and structurally similar organic compound(s) or ratios thereof in the one or more additional samples, wherein the greater presence of corresponding or structurally similar organic compounds or ratios in one or more of the one or more additional samples with respect to organic compounds or ratios identified in the first sample increases the likelihood of the first fluid sample and one or more of the one or more additional samples having originated from the same source.

According to specific alternative applications of the method(s) herein, the invention is a method for identifying carbon dioxide, or in aspects a lack thereof, in the assessment or monitoring of, e.g., carbon capture and storage reservoirs or also or alternatively in establishing the migration volume of enhanced oil recovery carbon dioxide. In aspects, the methods herein can be applied to the determination of potential leaking of CO2 from CO2 storage reservoirs. In aspects, the methods herein can be applied to the detection of CO2 injected as a component of enhanced oil recovery efforts. In such aspects, the method(s) comprise the collection of a sample of a fluid comprised substantially of a gas, e.g., carbon dioxide, and further the collection of a series of non-fluid samples comprising rock from a plurality of locations of a petroleum well. The method can then further comprise subjecting the fluid material to an analysis that identifies the approximate amount of about 2-120, 2-100, 2-80, 2-60, 2-50, 2-40, 2-20, 2-10, 2-8, 3-120, 3-90, 3-60, 3-30, 3-18, 3-9, 3-8, 2-7, 3-7, 2-6, 3-6, 4-80, 4-60, 4-40, 4-20, 4-10, or about 4-8 compounds, typically that are selected from a group of compounds suitable for the method(s) herein which, in aspects, is no greater than about 200 compounds (e.g., ≤150 compounds, ≤125 compounds, ≤110 compounds, or ≤100 compounds). In aspects, such limited number of compounds mostly, generally, substantially, or only have other characteristics described herein (e.g., being C4-C10 hydrocarbons). In aspects, the method further comprises subjecting the series of non-fluid material samples to an analysis that identifies the approximate amount of at least 2 of the same or similar chemical species (e.g., CSC, CCSC, SSC, or any combination thereof, including isotopes thereof), such as at least about 3, at least 4, at least 5, at least 6, at least 7, or at least about 8 of the same species (such as about 2-10 species, 3-9 species, or about 3-7 species). In certain aspects, in applications wherein the method is also or alternatively applied to gasses associated with a site, well, etc., applicable compounds can include but may not limited to, for example, the analysis of C12, C13, O16, and O18 (and related compounds). Compound(s) typically are analyzed in each of the series of second samples where obtained/provided. In aspects, ratio(s) between different structural classes of such compounds which may be applicable to gas-related analysis methods can include, e.g., C12 versus C13, CO2 versus CS2, and O16 versus O18 isotopic composition. In certain aspects the method further comprises dividing the site under analysis (e.g., petroleum well) bore length into location intervals and combining the series of ratios calculated for each of the non-liquid material samples collected from within each of the defined intervals to establish an average or representative ratio for each of the previously defined intervals ("interval ratios"). Further, the method described can comprise assigning each interval ratio a weighting factor so as to assign each location interval within the well a weight representative of its overall spatial contribution to the total length of the well bore to establish a first set of representative bore hole interval values ("length-weighted interval ratios"). Further, the method can comprise applying a numerical method analysis to the collection of length-weighted interval ratios capable of iterating various combinations of applied weighting factors and comparing the results of such iterations to a target value, the target value being derived from the fluid sample, with the weighting factor as an adjustable variable. Further, the method can comprise identifying the combination of weighting factors, which, when applied to each interval ratio, results in a weighting of the bore intervals such that when all interval ratios are considered, the combination most closely represents the profile of the fluid sample. Finally, the method can comprise utilizing the identified weighting to establish the relative proportion of productivity of each interval of the well to the fluid sample.

BRIEF DESCRIPTION OF THE DRAWINGS/FIGURES

FIG. 3 illustrates data discussed in Example 1.

Figure 7:
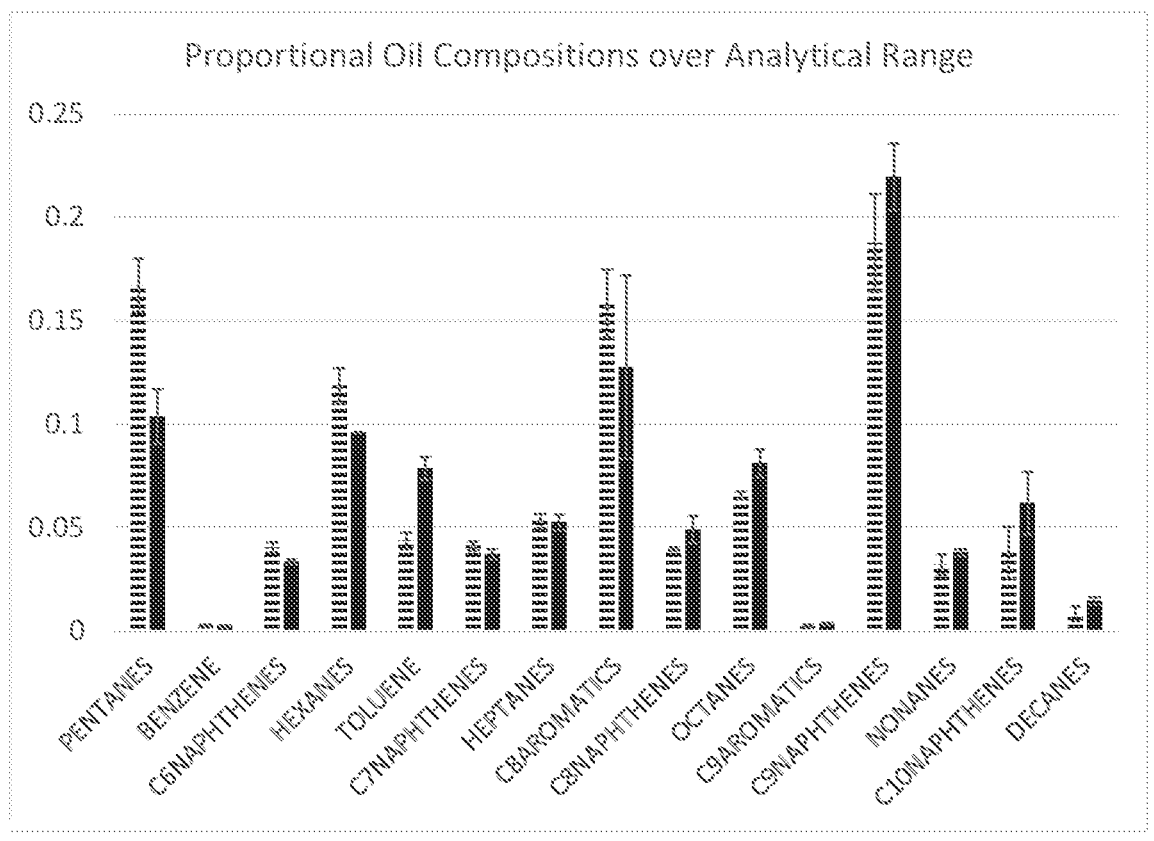
FIG. 7 is a graphical representation of data collected from two oil samples, analyzed by RVS technology, which exemplify the mole fractions of the different liquid hydrocarbons measured and indicate that the two oil samples are different in nature and thus indicative of the two oil samples having originated from different sources.
Figure 8:
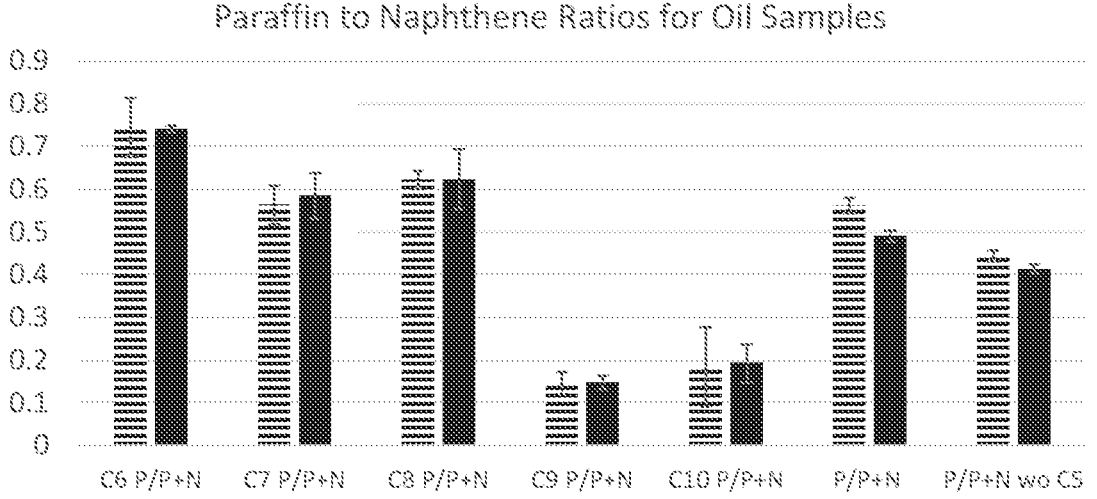

FIG. 8 is a graphical representation of the same two oil samples as shown in FIG. 7 and analyzed by RVS technology, which provides an additional representation of the data using the ratios of measured paraffins versus the sum of measured paraffins and naphthenes, which indicates that the two oil samples are quite similar in nature, are likely related, and thus indicating that the two samples likely originate from the same source.

DETAILED DESCRIPTION OF THE INVENTION

The various aspects and embodiments of the invention will be described in this section of the disclosure in detail, often with focus on a particular step of a method, type of analyte, type of sample, and the like. Those of skill in the art, however, will recognize that any such aspect of the disclosure can be combined with any other suitable aspect described in this section or any other section of the disclosure.

In one aspect, disclosed herein are methods capable of (a) analyzing the oil production properties of a well; (b) analyzing the oil production properties of an oil-associated geologic unit; (c) analyzing the oil production properties of one or more parts of an oil well-associated geologic unit; (d) analyzing the fluid characteristics of a geologic area (e.g., (1) the carbon dioxide-related characteristics of carbon capture and storage operations (e.g., leakage from carbon dioxide storage reservoirs), (2) the carbon dioxide-related characteristics of enhanced oil recovery operations, or (3) analyzing geothermal well characteristics); (e) allocating a relative proportion of productivity to each interval of a plurality of intervals within a the geologic area (e.g., within a single petroleum well); (f) predicting the highest (producing, escaping, or containing) zones of fluid in the area (e.g., in yet-to-be completed oil wells); and also or alternatively (g) evaluating or identifying the source(s) of produced fluid. In certain aspects, the method(s) of the invention herein are capable of identifying relative contribution of locations, sources, or both, of fluid across any kind of geologic unit (e.g., a site such as a well or a geologic formation). In several aspects methods are focused on the characterization of cumulative contributions of zones/intervals of an area of a petroleum well, such as along some, most, generally all, or all of the well/borehole or a part of a well. In several aspects, methods are focused on the characterization of contributions, e.g., relative contributions, of one or more source(s) of material to a produced fluid collected from a geologic site.

According to some aspects, methods of the invention can be characterized in comprising the following phases, which are discussed in detail individually herein, recognizing that such methods can be combined in any suitable manner and, where sensible, practiced in any suitable order, and whereby in certain applications not all steps may apply:

a. Solid Material, e.g., Rock, Sample Collection: Samples of solid material, e.g., rock materials, are collected by any suitable method (e.g., by collection of drill cuttings, such as Polycrystalline Diamond Compact (PDC) drill cuttings, such as cuttings delivered by an OBM. Herein, disclosure related specifically to the use of "rock materials", uncontradicted, can be interpreted to encompass disclosure other solid material sample(s) as suitable for use in the methods described herein. In aspects, a solid material can be, e.g., a rock material. In aspects, a rock material can be drill cuttings. Herein, specific reference to cuttings can be, uncontradicted, be interpreted to encompass disclosure of other rock material(s) (such as, e.g., core sample(s), or, e.g., other solid materials as suitable for use in methods described herein. The solid material, e.g., cuttings, can be hermetically sealed, usually promptly following collection, e.g., within less than about one day, less than about 4 hours, less than about 1 hour, less than about 20 minutes, less than about 10 minutes, or less than about 5 minutes, to avoid loss of compounds, such as cuttings-associated rock volatile compounds discussed in the SMITH Art.

b. Fluid Sample Collection: In many, but not necessarily all, embodiments of this invention, one or more samples of fluid also are collected from a well or a related geologic area or geologic unit (e.g., a co-located well expected to have similar properties). In one embodiment, the fluid is a formation fluid (e.g., production oil). In some embodiments, the fluid is a condensate. In another embodiment, fluid is a fluid that has been in contact with a formation fluid. In some embodiments, 2, 3, 4 or more, such as 5 or more, 10 or more, 20 or more, or, e.g., 50 or more samples of fluid are collected. In some embodiments, fluid is collected at different times during operation of a well so as to assess changes in the well. In some embodiments, the well can be an operational well or a pre-operation well. Typically, a fluid sample is optionally hermetically sealed upon collection, to avoid loss of material, typically within less than 1 day, e.g., less than 2 hours, less than 1 hour, less than 20 minutes, less than about 10 minutes, less than about 5 minutes, or less than about 2 minutes, from collection. In some embodiments, the fluid sample is from a known portion of a well that corresponds to less than the entire well. In methods in which release resistant water is used as the only or primary analyte the fluid sample collection step may sometimes be excluded. In certain embodiments, the fluid is or comprises a gas, e.g., the fluid is carbon dioxide.

c. Solid Material Sample Selection/Validation: In aspects, the inventive methods can include a step of determining the portion of solid material samples obtained from a well that should be used in the analytical method. For example, in aspects of the invention focused on the characterization of lateral wells, the focus of solid material sample analysis can, in aspects, be on those samples obtained from at least one lateral well, in some embodiments more than one lateral well.

d. Fluid Sample Validation: In some aspects, method(s) comprise the step of analyzing whether or not the fluid sample, e.g., a liquid sample, is indicative of a sufficient amount of oil in the well to perform other steps of the method.

e. Analyte Selection/Validation: The compounds to be analyzed in the analytical steps of the method are often pre-determined based on (a) analysis of the rock content of the geologic unit (such as, e.g., a formation)—e.g., in terms of whether or not the geologic unit is "tight" (which can impact certain aspects of analysis, such as whether absolute values are suitable for use), whether the geologic unit comprises a significant amount of potentially interfering rock, such as a high quartz content (thus expecting to make aromatic compounds poor choices for analysis), or both. For example, some clays, shales, and rock comprising high organic content can in aspects potentially impact aromatic distribution and may in facets impact hydrocarbon compound selection. Accordingly, in aspects, the compounds utilized in (a) method(s) can be selected based upon the presence or absence of potentially interfering rock, such that analytes which may be interfered with by a type of rock present in the applicable site, portion of a site, etc., are not selected for use in the method.

f. Election of Comparators: In aspects where a comparison of two or more compounds is performed, such as in the methods comprising the comparison of compounds in a fluid and a solid sample, either directly measured values or ratios of two or more compounds, which can be, e.g., hydrocarbon species (e.g., between about 2-120, 2-80, 2-60, 2-50, 2-40, 2-20, 2-10, 2-8, 2-7, 3-120, 3-90, 3-60, 3-30, 3-18, 3-9, 3-8, 3-7, 4-120, 4-100, 4-80, 4-60, 4-40, 4-20, 4-12, 4-10, or about 4-8 species), and are often compounds of different classes (e.g., branched and normal alkanes or acyclic alkanes and cycloalkanes) are selected. In aspects, e.g., wherein the method is applied to gas-related applications, selected compounds are or can comprise inorganic compound(s), such as, e.g., $CO_2$, $COS$, $CS_2$, $SO_2$, and $H_2S$ or related compounds. The compounds compared within each sample if a ratio method is used are often similar to each other in size (within 0-2 carbon difference of one another) but usually are different in terms of other characteristics, such as whether or not the compound has a cyclic structure versus an acyclic structure and in more particular aspects whether or not the compound is a linear acyclic compound or a branched acyclic compound. In one embodiment the difference between the compounds in a ratio analysis is between one or more paraffins and one or more naphthenes.

g. Real World Data Collection: In some cases a method includes collection of one or more aspects of "real world" data concerning the well, such as obtaining information regarding where the well is open to oil flow(s).

h. Analyte Collection and Analysis: In aspects, the methods comprise the use of one or more of a variety of methods for collecting analytes for analysis. In one method, the analytes comprise one or more, typically at least 2, at least 3, or at least 4 sets of compared compounds ("compounds") (e.g., but not limited to hydrocarbons, such as acyclic alkanes and cycloalkanes, water, or both). In one aspect, the analytes are volatile compounds released from the samples. In one aspect, the volatile compounds are volatiles released from one or both types of samples using the methods described in the SMITH Art (e.g., gentle vacuum volatiles extraction, cryogenic capture, warming release, and mass spectrometry analysis). In one aspect the method does not comprise the use of gas chromatography in such analysis.

i. Spatial Weighting: In embodiments wherein the aim of the method is to determine the relative contribution of two or more positions, intervals, portions (or, e.g., locations) of a well or other geologic site (e.g., a single reservoir compartment) to a produced fluid, the two or more samples representative of different well depths can be weighted. In aspects, such weighting is established according to their respective representation of the total well or geologic site dimension, such as, e.g., depth or length. Weighting can, in aspects, factor in real world factors such as whether or not the area is open to oil flow.

j. Mathematical Analysis: In certain embodiments, a mathematical analysis is performed to determine the required contribution at each position to produce the composition of the product. In some embodiments, a scaling factor, as calculated by the mathematical analysis for each input location, is provided for each accordingly, the scaling factor representing the relative contribution of that interval to the final produced product. In aspects, the sum of the scaling factor times the value(s), e.g., ratio(s) being considered at a given depth interval, across all depth intervals considered, results in values that reasonably reproduce (e.g., approach in an attempt to match), the same value(s), e.g., ratio(s) measured from the produced oil sample. This kind of analysis can, in aspects, result in a map of regions or locations that provide relative contributions to material, e.g., oil, production in the geologic site, e.g., well. In aspects, the mathematical analysis is performed by a pre-programmed computer. In aspects, the mathematical analysis is performed using one or more software tools designed to perform such a mathematical analysis. In aspects, computer systems for performing such analyses are a part of the invention. In aspects, machine learning can be applied to such methods, which steps/aspects are further described below.

k. Sufficiency Analysis: In aspects, the analytical information derived from any one or more step(s) of the method(s) can be analyzed for "sufficiency", wherein sufficiency is an evaluation of how likely it is that the characteristic(s) of a first sample, e.g., a first fluid, are being contributed to by any second or more other sample(s), e.g., a second, third, fourth, fifth, tenth, fiftieth, one hundredth, etc. sample(s). In aspects, the analytical information derived from any one or more step(s) of the method(s) can be analyzed with regard to their ability to identify an original source of any first sample as being the same as one or more second or additional sample(s). Specifically, in aspects, the analytical information derived from any one or more step(s) of the method(s) can be analyzed with regard to the presence of hydrocarbon liquids and whether given samples have the same source of origin (e.g., the same "provenance"). In the event the analytical information derived from the various step(s) of the method(s) is deemed insufficient, e.g., the analytical information indicates that, e.g., (a) any second or additional sample(s) collected from one or more locations does/do not explain or identify one or more locations of, e.g., a geologic site, e.g., well, contributing to the characteristic of a first sample, e.g., a first fluid sample, or (b) any second or additional sample(s) collected from one or more locations does/do not identify such sample(s) as sharing the same source location as any first sample, e.g., first fluid sample, various step(s) of the method(s) can, in aspects, be repeated for additional samples.

l. Oil Typing Application: In aspects, analytical information derived from the various step(s) of the method(s) can be used to determine the likelihood of multiple fluid samples having originated from the same source, e.g., sharing provenance. In aspects, the analytical information derived from the various step(s) of the method(s) can be used to identify if two (or more) fluid samples collected from, e.g., a single geologic site such as the same well share the same source location. In aspects, the analytical information derived from the various step(s) of the method(s) can be used to identify if two (or more) fluid samples collected from, e.g., the same geologic site were expelled from the same source rock at a similar point in time in terms of the maturation of the source rock; e.g., have the same pulse.

m. Application: In aspects, the analytical information derived from the various step(s) of the method(s) can be used to direct activities, e.g., current or future petroleum drilling operations, such as identifying, e.g., which areas of a well are worthy of completing, or for example identifying placement of new horizontal well lines, fracking, or both, or, in other contexts, informing, directing, or otherwise contributing to carbon sequestration or geothermal activities.

According to certain aspects of the invention, the method comprises use of all steps as described (a)-(l) above. According to certain alternative aspects of the invention, the method comprises a subset of the steps (a)-(l) above. In certain aspects, any of steps (a)-(l) or subsets thereof can be performed in sequential order. In certain alternative aspects, one or more steps (a)-(l), including subsets thereof, can be performed out of sequence or at substantially the same time as any other one or more steps.

In aspects, the methods described herein when applied to the allocation of spatial contribution to a produced fluid are distinguishable from that of the prior art in at least two distinct ways. In aspects the methods herein do not attempt to assign production contribution allocations by matching oil signatures; but, instead, determine production contribution based on relatively small and discrete zones, such zones typically not being more than 120 feet and being more typically closer to e.g., about 100 feet or less, 90 feet or less, 80 feet or less, 70 feet or less, 60 feet or less, or ~50 feet or less. Accordingly, heterogeneity across a well/borehole length is maintained and considered, such heterogeneity being lost in applications wherein longer intervals between sample collection are applied. Such longer intervals may be appropriate for applications wherein a larger field is under analysis, however such intervals applied to a single well will render the analysis inaccurate and/or useless. In aspects, methods herein utilize rock samples collected in intervals of no more than about 120 feet, 100 feet and typically no more than about 90, e.g., ≤~80, such as no more than about 60, or no more than about 40 feet (e.g., about 15-90 feet, about 10-100 feet, or about 20-80 feet). In aspects, collection of such dispersed samples provides for a cumulative approach to the determination of how much any single point or area contributes to a final production fluid. In aspects, the result of an analytical method of the invention is a detailed characterization of the relative contribution made by points along the length of a single well to the final produced fluid from that well or from the final fluid expected to be produced from that well, as will be described elsewhere herein.

The above-described steps and various aspects thereof will now be discussed in further detail and with particular focus.

Sample Collection

In aspects, the methods of the invention comprise collection of at least one or more solid material samples, e.g., rock samples, e.g., petroleum drill cuttings, and typically comprise the collection of a plurality of such samples, e.g., at least about 5, at least about 10, at least about 20, at least about 50, at least about 100, at least about 200, or at least about 250 samples, which typically are obtained from different parts of a site (e.g., regions of one or more petroleum wells), e.g., one or more regions that are separated by one another by at least about 15, at least about 30, and often at least about 45, at least about 50, or at least about 60 feet, in one or more directions, from, in aspects, one or more other samples or, e.g., in aspects, from substantially all other samples. According to certain aspects, the collection of at least two or more rock samples comprises collection of samples across intervals of no more than about 120 feet, such as no more than about 90 feet, no more than about 80 feet, no more than about 70 feet, no more than about 60 feet, no more than about 50 feet, no more than about 40 feet, no more than about 30 feet, no more than about 20 feet, or in some aspects no more than about 10 feet, such as for example between about 10-120 feet, about 30-120 feet, about 50-120 feet, or, e.g., between about 10-80 feet, 10-70 feet, 10-60 feet, or, e.g., between about 10-50 feet. In aspects, interval length is suitable for providing information relative to lateral heterogeneity that would otherwise be lost, such as in circumstances wherein the lateral heterogeneity changes across a span of a well and larger intervals would miss the ability to interpret the impact of such heterogeneity.

According to certain aspects of the method(s) disclosed herein, the method comprises collection of a plurality of sample types. In aspects, the method comprises the collection of at least two types of samples. In aspects, the method comprises the collection of a first fluid sample (or a collection of fluid samples, collected either at about the same time or different times, e.g., over the course of the operation of a well). In aspects, the method comprises the collection of at least one second, such as a second one or more non-liquid (solid material, or herein simply referenced as "solid") samples, comprising, e.g., rock, from a geologic unit. In aspects, the second one or more solid material samples are representative of one or more physical locations within one or more geologic site(s), e.g., well(s). Specific descriptions of each type of sample are provided elsewhere herein. In aspects, a fluid sample utilized in the method(s) herein can be collected in one time period and non-liquid (solid) sample used in the method can be collected during a different time period. In certain aspects, a fluid sample used in the method(s) herein can be collected minutes, hours, days, weeks, months, years, or even decades before or after a non-fluid (solid) sample used in the method. In aspects, non-liquid (solid) sample(s) used in the method(s) herein can be collected minutes, hours, days, weeks, months, years, or even decades before or after a liquid sample used in the method. In aspects, the fluid sample can be a liquid or a gas sample, including, e.g., a condensate sample, such selection being dependent on the aim of the analysis (e.g., production allocation to a produced whole oil or, e.g., alternatively carbon capture and storage applications). In aspects, most, generally, or all fluid samples are mostly, generally, or entirely liquid samples when analyzed.

According to the method, one or more characteristics, e.g., a directly measured value of one or more analytes, e.g., one or more compounds, such as, e.g., hydrocarbons of one or more non-fluid materials (e.g., solid material samples), are compared to the one or more characteristics of a fluid sample so as to determine, e.g., the relative contribution, or, alternatively, the absence of detectible or significant contribution, of each physical location represented by the one or more non-liquid samples.

While the number of fluids, e.g., liquid, samples is often limited to 1 sample, or just a few samples (e.g., about 1-5 samples, 2-4 samples, or about 1-3 samples), the number of solid material samples, e.g., rock samples, will often be greater than 5, such as at least about 10, at least about 20, at least about 50, at least about 100, at least about 150, at least about 200, at least about 250 or more (e.g., about 10-1000, about 15-750, about 20-500, or about 25-450 samples). Rock samples, in aspects, often comprise core samples or petroleum drill cuttings. Typically, such cuttings are sealed promptly upon collection at the well, as discussed above.

According to certain aspects the number of fluids, e.g., liquid, samples is not limited to 1 sample, or just a few samples (e.g., about 1-5 samples, 2-4 samples, or about 1-3 samples), and the number of liquid samples will often be greater than 5, such as at least about 10, at least about 20, at least about 50, at least about 100, at least about 150, at least about 200, at least about 250 or more (e.g., about 10-1000, about 15-750, about 20-500, or about 25-450 samples).

In certain aspects, the number of fluid samples is less than the number of solid material samples used in a method. In aspects, the number of fluid samples is the same as the number of solid material samples used in a method. In aspects, the number of fluid samples is greater than the number of solid material samples used in a method.

According to certain aspects, only fluid material samples are used in a method, such as, e.g., no solid material samples are analyzed as a step of certain embodiments of method(s) disclosed herein.

According to certain aspects of the present invention, one or more fluid samples can be collected from the same geologic site, e.g., well, e.g., petroleum well, as non-liquid material sample(s). According to alternative aspects of the present invention, a fluid (e.g., liquid or gas) reference sample can be collected from a different well as non-liquid material sample(s). In some embodiments, a fluid reference sample can be collected from a different well as the non-liquid material sample(s), however the two wells can have access to, e.g., being drilled within, the same geological unit, e.g., being drilled within the same geological formation; be drilled within the same drilling pad; be a part of the same play; be located within the same geological region or area, such as, e.g., within one mile of one another; have access to the same reservoir(s); have access to produced oil located ("reservoired") within the same zone; or any combination thereof. According to certain aspects, method(s) comprise the analysis of only fluid samples. In aspects, all fluid samples are collected from the same geological site, e.g., the same well, e.g., petroleum well. In aspects, at least two or more fluid samples analyzed in a method are collected from two or more geological site(s). In aspects, at least two of the two or more geological site(s) can have access to, e.g., are located within, the same geological unit, such as, e.g., the same geological formation.

Comparing the selected analytes, or, e.g., comparing ratios of selected analytes, of non-liquid sample(s) to the same or similar (e.g., related by number of carbons or by structure) analytes or ratios of analytes of the fluid is an embodiment of many, but not all, methods of this invention.

Comparing the selected analytes or ratios of analytes of the liquid sample(s) to the same or similar (e.g., related by number of carbons or by structure) analytes or ratios of analytes of a second fluid is another embodiment of many, but not all, methods of this invention.

Significant value can be derived from those methods of the invention utilized to predict the relative contribution of one area of an, e.g., well, over another either prior to drilling such a well, prior to completion of that well, or prior to a point in time in which a produced fluid from that well is available. In such scenarios, a produced fluid from a well within the same geological unit, within the same drilling pad, within about 1 mile (e.g., within about 0.75 mile, within about 1 kilometer, within about 0.5 mile, or within about 0.25 mile) of, and typically having access to the same reservoir(s) as, having access to produced oil reservoired within the same zone of, or any combination thereof, of the yet-to-be drilled well, yet-to-be completed well, or well otherwise not having a produced fluid available, can be utilized, as the profile of such a produced oil is often not likely to be significantly different. In such a case, the analytes or ratios of interest can be compared using the methods described herein between the non-liquid samples from the not-yet completed or not producing well and the fluid sample from the nearby (or otherwise related as described) producing well in order to obtain a predicted relative contribution profile of the areas of the not-yet completed, drilled, or otherwise producing well to the expected produced fluid from that well once brought online.

To further exemplify and clarify certain of the above-described aspects of the invention, the following exemplary scenario is provided:

a. Four vertical wells exist within an oil field (wells A, B, C, and D);

b. Each of the four wells penetrate multiple strata of rock within the same geological unit;

c. One of the four wells (well A) is on production (e.g., has a production fluid which can be sampled);

d. The other three wells (wells B, C, and D) have vertical boreholes drilled and are in various stages of being brought online.

In the above-described scenario, one of ordinary skill in the art, given the guidance of this disclosure, could potentially use the fluid produced from producing well A as the fluid sample in the methods described herein. Samples, e.g., drill cuttings or core samples (as will be described elsewhere herein) representative of each of wells B, C, and D along the lengths of each well can be collected. Using a method described herein, the comparison of values of the cuttings to the values of the produced fluid/gas of well A can be used to determine the predicted relative contribution locations within each of wells B, C, and D to the final expected fluid product of each of respective wells B, C, and D.

In some aspects the fluid sample can be any fluid for which the presence or absence of a contribution from a single location is desired to be determined. In aspects, the sample of fluid used in methods that comprise fluid sample analysis could be any fluid representative of a fluid for which relative contributions from differing sources are desired to be known. For example, the fluid sample(s) can be/include an oil (e.g., where contributions to the oil from a plurality of locations in a site is to be determined). In aspects, a fluid sample can be a condensate. In aspects, the fluid sample(s) can be/include carbon dioxide gas for which, e.g., leakage sites (e.g., in carbon capture and storage applications) or migration patterns (e.g., in enhanced oil recovery applications) are desired to be determined.

In an alternative example, the fluid sample can be a water sample, or a set of fluid samples can comprise a water sample or an aqueous composition sample, e.g., a contaminant water of a produced fluid, wherein one wishes to determine locations within a well contributing to that source of contaminant water. In aspects where water samples are utilized, the method of the invention can comprise analysis of compounds in addition to or other than hydrocarbons. In aspects, useful compounds for comparison can be, e.g., hydrophilic compounds such as but not limited to organic acids. In aspects, hydrocarbons can be used in the analysis of aqueous fluid (water), and either a) supplemental data, or b) established assumptions, related to the solubility of hydrocarbons may be utilized as an element of analysis.

In some aspects, a first fluid sample is comprised essentially of, or substantially consists of a liquid. As used herein, the phrase "comprised essentially of" means containing at least about 90%, or at least 95% of such material, such as for example at least 96%, at least 97%, at least 98%, at least 99%, at least 99.5%, or could even contain up to 100% of the material.

According to certain embodiments, a liquid sample comprises either a formation liquid (e.g., a production oil) or a liquid that has been in contact with a formation liquid under conditions sufficient to transfer a detectable amount of the at least one compound, if present, to the liquid sample. In some aspects, the fluid is/comprises a produced oil. In some aspects, the sample is a flowback material. In certain aspects, the fluid is/comprises water. In certain embodiments, the fluid is from a fluid inclusion. In some aspects, the fluid inclusion can be from the same samples as the second set of non-liquid samples to be further described elsewhere herein. In some embodiments, the fluid is not fluid from a fluid inclusion. In some embodiments, fluid inclusion analysis is used in combination with the other aspects of the inventive methods described herein. In certain aspects, the fluid is a condensate.

According to certain aspects of the present invention, one or more samples of fluid are collected and one, most, or all, are each hermetically sealed upon collection. In some aspects, sealing takes place within 1 hour of collection, such as within about 50 minutes, within about 40 minutes, within about 30 minutes, within about 20 minutes, within about 10 minutes, within about 5 minutes, within about 4 minutes, within about 3 minutes, within about 2 minutes, or within about 1 minute of collection, such as for example being sealed within about 20 minutes of collection, within about 18 minutes of collection, within about 16 minutes of collection, within about 14 minutes of collection, within about 12 minutes of collection, within about 10 minutes of collection, within about 8 minutes of collection, within about 6 minutes of collection or even less. Ideally, samples can be sealed as soon as possible upon collection to avoid contamination or loss of analytes of interest. Samples can be collected in any suitable container which does not alter or interfere with the analytes of interest, e.g., Nalgene containers can be a suitable collection container. In certain aspects, if the primary material collected is a gas, a container that is suitable for maintaining the gas within the container may be required.

Any suitable volume of a liquid sample can be collected for practice of the methods comprising a liquid sample analysis step. In certain aspects, at least 1 mL of sample is collected, e.g., at least about 2 mL, at least about 5 mL, at least about 10 mL, at least about 20 mL, at least about 30 mL, at least about 50 mL, at least about 75 mL, or at least about 100 mL, such as at least about 250 mL, at least about 500 mL, or at least about 1 L of sample is collected. The amount used for analytical testing is typically between 10 $\mu$L-200 $\mu$L, the amount used most commonly being driven by equipment limitation(s).

In aspects, the suitable fluid is a produced oil or gas, most typically a fluid comprising a liquid. In some respects, the fluid can be collected from a separator. In certain aspects the fluid can be collected from the same well as the non-liquid sample(s). In certain aspects, the fluid can be collected from a different well as the non-liquid samples. In some embodiments, the well from which the fluid sample is collected and the well from which the non-liquid sample(s) is/are collected are different wells within the same geological unit or otherwise related area as previously described.

In certain aspects, the suitable fluid is flowback material. Flowback material is material being returned to the surface once a well is completed however prior to bringing the well officially online. During this period, some material is returned which will not be seen later in the well production. In certain aspects, this material can be collected and used as the liquid sample in the methods described herein.

A common use of conventional production logs (e.g., use of spin wheel technology and other associated sensors) is to determine if unwanted water is entering the borehole and if so, from what location. In some aspects the fluid sample predominately comprises, at least substantially consists of, or entirely consists of water, e.g., a contaminated water. In certain aspects, the sample of water can be water collected from a separator used in oil production in a well. In aspects, the methods of the present invention could be applied to determining where within a well an influx of water is coming from. In such a scenario, analytes within the water are compared to the analytes within non-liquid samples representative of multiple locations within a well. The selected hydrocarbon profile can be analyzed on the water sample, measured on the non-liquid samples, and an analysis applied as described elsewhere herein to determine the relative contribution of different areas of the well to the profile of the contaminant water, thus providing insight into which locations within the well are contributing most to, and likely the highest sources of, the contaminant water.

In some aspects the fluid sample is extracted from a fluid inclusion or more typically multiple fluid inclusions, which can be accessed through crushing of cuttings or other methods, described in the art cited in the SMITH art. In certain embodiments the fluid inclusion(s) from which the suitable fluid or gas is extracted is/are fluid inclusions within drill cuttings samples. In certain aspects, such drill cuttings samples can be drill cuttings used as the non-liquid samples used within the method as further discussed herein. As noted elsewhere, the fluid typically is not a fluid inclusion-based fluid, but, optionally, fluid-based inclusion methods described in the SMITH art and patent documents cited therein can be combined with the methods of this disclosure.

In some aspects, the suitable fluid is a condensate. In some aspects such a condensate comprises both a liquid and a gas, but in some aspects at least primarily comprises a liquid at analysis. In aspects, the method is applied wherein some, most, generally all, substantially all, or all of the compounds (or some, most, generally all, substantially all, or all amounts of some, most, or all thereof) in the liquid (e.g., oil) analyzed in the method are attributable to condensate(s). Condensates are recognized in the art as hydrocarbons that are in a liquid phase under surface conditions, generally thought of as standard temperature and pressure (STP), i.e., room temperature at 1 atm, however reside in the subsurface in a gas phase. In aspects, some most, generally all, substantially all, or all of the compounds (or some, most, generally all, substantially all, or all amounts of some, most, or all thereof) compounds analyzed in a liquid are from non-condensate deposits that contribute to the liquid that is analyzed in the method. In aspects, some most, generally all, substantially all, or all of the compounds (or some, most, generally all, substantially all, or all amounts of some, most, or all thereof) analyzed in a liquid are from both condensate and non-condensate deposits that contribute to the liquid that is analyzed in the method.

Some embodiments of the present invention comprise the collection of one or more non-fluid, e.g., non-liquid (solid material/solid) sample(s), typically comprising rock from a geologic unit (e.g., formation) associated with the well or from a corresponding portion of the geologic unit (e.g., a nearby well having similar geologic properties). Such non-fluid samples typically are one or more samples collected at different locations in space, such as for example at different depths across the length of a vertical well or horizontal locations along a horizontal well, such as the type of samples described in the SMITH Art.

In one aspect, the one or more collected non-fluid samples is/are comprised of a rock material from a geologic unit. In certain aspects, the rock material is rock material collected from different depths or locations along a bore hole. In some aspects, the non-fluid samples are or comprise drill cuttings. According to alternative aspects, the non-fluid samples are or comprise core samples. In certain aspects, the samples are or comprise one or more sidewall core(s). In one aspect, the non-fluid samples are drill cuttings sealed at the well (e.g., within about 1 hour or less, such as within about 30 minutes, within about 20 minutes, within about 15 minutes, within about 10 minutes, or within about 5 minutes of the cutting reaching the surface). In one aspect, the cuttings are not washed prior to analysis, dried prior to analysis, or are not washed and dried prior to analysis.

Samples of non-fluid (or non-liquid; herein, reference to "non-liquid" samples can, uncontradicted, but interpreted to encompass disclosure of "non-fluid" samples) samples typically are collected and hermetically sealed upon collection. In some aspects, sealing takes place within 1 hour of collection, such as within about 50 minutes, within about 40 minutes, within about 30 minutes, within about 20 minutes, within about 10 minutes, without about 5 minutes, within about 4 minutes, within about 3 minutes, within about 2 minutes, or within about 1 minute of collection, such as for example being sealed within about 20 minutes of collection, within about 18 minutes of collection, within about 16 minutes of collection, within about 14 minutes of collection, within about 12 minutes of collection, within about 10 minutes of collection, within about 8 minutes of collection, within about 6 minutes of collection or even less. In aspects, samples are sealed as soon as possible upon collection to avoid contamination or loss of analytes of interest.

In aspects, samples can be collected in any suitable container which does not alter or interfere with the analytes of interest. One exemplary example of such a suitable container can be, e.g., Nalgene® container(s).

Samples can be collected by any suitable methods. In aspects where the non-liquid samples are core samples, appropriate core collection techniques known in the art can be utilized to obtain the samples.

In general, any suitable volume of sample can be collected for performing methods. In certain aspects, at least 1 mL of a solid sample is collected ("mL" being used in reference to an amount of a substance filling a cubic centimeter's space and comprising solid material, e.g., a drilling mud comprising drill cuttings), for example at least about 2 mL, at least about 5 mL, at least about 10 mL, at least about 20 mL, at least about 30 mL, at least about 50 mL, at least about 75 mL, or at least about 100 mL, such as at least about 250 mL, at least about 500 mL, or at least about 1 L of sample is collected. The amount used for analytical testing is typically between 10 µL-1000 µL, such as about 25-750 µL, e.g., about 100-600 µL, about 150-600 µL, or about 200-600 µL, e.g., approximately 400 µL. In aspects such an amount of material can be described by weight, such as, for example at least about 1 g or at least about 250 g of material, such as between about 1 g-about 200 g, between about 1 g-about 150 g, between about 1 g-about 100 g, between about 1 g-about 50 g. between about 1 g-about 25 g, or between about, e.g., 1 g-20 g, 1 g-15 g, 1 g-10 g, 1 g-5 g, or 1 g-2 g. In aspects, such an amount of material can be less than one gram, such as, e.g., 1 µg, e.g., between about 1 µg-about 950 µg, 1 µg-750 µg, 1 µg-500 µg, 1 µg-250 µg, 1 µg-200 µg, 1 µg-150 µg, 1 µg-100 µg, 1 µg-50 µg, 1 µg-25 µg, 1 µg-20 µg, 1 µg-15 µg, 1 µg-10 µg, or, e.g., between about 1 µg-5 µg. In aspects, the amount of solid material can be less than 1 µg.

According to certain aspects, cuttings can be the source of fluid inclusions, the fluid from which can be extracted and used as the fluid sample, as a fluid sample, or as part of a fluid sample, for a fluid analysis step of a method of the invention, as described elsewhere herein. In other aspects, the fluid sample is not derived from a fluid inclusion. In aspects, the fluid sample is not derived from a fluid inclusion but method(s) still comprise performing fluid inclusion analysis of cuttings along with the analysis of cuttings through the methods of the SMITH Art or otherwise.

In certain embodiments, non-fluid samples, such as cuttings, are collected from water-based drilling muds. In certain alternative aspects, cuttings are collected from oil-based drilling muds or cuttings comprise cuttings that have been in contact with OBMs. Oil based mud systems, where oil is used as the solvent instead of water, have become increasingly popular in production, especially in unconventional plays. In some settings/technologies, use of samples from wells drilled using oil-based muds is not viable, as the oil in the mud system adds its own hydrocarbon signatures that obscure the fingerprint attempting to be analyzed. In one aspect, analytes selected for analysis are organic compounds, e.g., hydrocarbons, of 11 carbons or less, such as for example 10 carbons or less or 9 carbons or less, and the interference with OBM components is minimized. In one such aspect, the dominant hydrocarbon species in the OBM analyzed are in the C12-16 range, such as are found in a diesel-based OBM.

Analyte Collection and Analysis

In aspects, collected samples are analyzed using a suitable technology to determine the amounts of target compounds, such as release resistant water or target compounds such as hydrocarbons (e.g., acyclic alkanes and cycloalkanes, such as between about 2-100, 2-60, 2-20, 2-10, 3-90, 3-45, 3-30, 3-18, or 3-9 target C4-C11 hydrocarbons) or, in certain specific aspects, C12 and C13, and also or alternatively in specific aspects inorganic compounds such as but not limited to $CO_2$, COS, $CS_2$, $SO_2$, $H_2S$, O16, and/or O18, including related compounds (e.g., isotopes) thereof. Such a suitable technology can be any technology capable of quantifying an amount of the target compounds.

According to aspects, the methods described herein comprise submitting solid sample(s) to the analyte extraction and measurement methods described in the SMITH Art, such as by subjecting solid material samples (e.g., rock samples such as cuttings or core material) collected at a plurality of well depths, e.g., at two or more well depths (e.g., 2, 5, 10, 20, 50, or 100 or more well depths) to such an analysis. In other aspects, the method further comprises collection of one or more fluid samples, and subjecting the fluid samples to any suitable analytical method to determine the amount of one or more components thereof, such as one or more compounds contained therein. In aspects, a fluid sample is also subjected to the analyte extraction, capture, and measurement methods of the SMITH Art.

According to certain embodiments, analytes are volatile compounds extracted from solid samples or fluid, e.g., liquid, samples by application of "gentle vacuum." In one aspect, gentle vacuum conditions mean application of a pressure of less than 200 millibars, such as a first phase about 100 millibars, or for between about 1 and 100 millibars, such as for example between about 5 and 90 millibars, or for example between about 10 and 80 millibars, or between about 20 and 70 millibars, or between about 30 and 60 millibars, or for example between about 40 and 50 millibars. Such a first phase can, in some aspects, be followed by another one or more phases of a different pressure, such as a pressure less than 100 millibars, such as for example less than about 100 millibars, less than about 90 millibars, less than about 80 millibars, less than about 70 millibars, less than about 60 millibars, less than about 50 millibars, less than about 40 millibars, less than about 30 millibars, less than about 20 millibars, less than about 10 millibars, less than about 5 millibars, or even less than 1 millibar, such as less than about 0.5 millibars, less than about 0.1 millibars, less than about 0.01 millibars, less than about 0.001 millibars, or even less than about 0.0001 millibars, the extraction extracting volatile gas and fluid species. In some embodiments, such extraction is followed by cryogenic trapping of selected compounds and the subsequent controlled, slow release thereof. In some aspects, quantification of compounds is optimally carried out by mass spectrometry. In certain specific aspects, quantification excludes use of gas chromatography. In certain aspects, the methods described herein can utilize technique(s) for extraction which is/are equivalent to gentle vacuum techniques such that the technique preserves one or more volatiles which are identifiable by, can be identified using, gentle vacuum extraction techniques.

In some cases, where release resistant water is an analyte, the method can comprise removal of extraneous water from solid samples and application of a gentle vacuum force that is capable of extracting release resistant water, such as is described in the SMITH Art.

In certain aspects, technologies other than, or in addition to, mass spectrometry can be utilized to measure compounds of interest (analytes). In some aspects, any technologies capable of measuring the target analytes of interest as described here without compromising other target analytes of interest would also be suitable.

In certain embodiments, use of gas chromatography (GC); GC-mass spectrophotometry (MS); Fourier-transform ion cyclotron resonance (FTICR)-MS; thin layer chromatography (TLC); 2D TLC; capillary electrophoresis (CE); high performance liquid chromatography (HPLC); Fourier-transform infrared (FTIR) spectrophotometry; x-ray fluorescence (XRF); atomic absorption spectrometry (AAS); inductively coupled plasma (ICP)-MS; ion chromatography (IC); nuclear magnetic resonance (NMR); two-dimensional gas chromatography and time-of-flight mass spectrometry (GC×GC-TOFMS); saturate, aromatic, resin, and asphaltene (SARA); carbon, hydrogen, nitrogen, sulfur and oxygen content (CHNOS); elemental analysis; GC/infrared (IR)-MS, or any combinations thereof are excluded from the analytical methods used in analyte analysis. In certain facets, one or more technologies or instruments suitable for aiding in the analysis of one or more analytes can be combined with one or more such technologies/instruments described above to improve upon the analysis platform. For example, in aspects, with regard to mass spectrometry-related analyses, MS-MS techniques can be utilized wherein a parent mass is selected, a collision, fragmentation, or separation stage is established, e.g., such as but not limited to an ion mobility technique, with sample then fed into an additional MS for more specific identification. In aspects, MS-MS-MS configurations can be suitable for similar, equivalent, or advanced analysis.

Analytes Selection and Comparator Selection for Comparative Analyses

In some embodiments the method will comprise a step of selecting the analytes, validating pre-selected analytes, or rejecting certain analytes from the analysis based on one or more factors. According to certain embodiments, the selection of compounds is based on the type of geologic unit, formation, area, or any combination thereof, and the composition of the rock therein. Thus, in one aspect, the invention described herein incorporates a characterization of the geologic unit from which samples are collected in addition to the application of the various steps of the methods described herein. For example, in one aspect the method comprises determining the silica content of the geologic unit and determining the analytes based on such information. In one aspect, for example, the presence of a significant quartz content of a geologic unit (e.g., at least about 5%, at least about 10%, at least about 15%, at least about 25%, or at least about 33% quartz content) can mean that aromatic compounds, compounds containing heteroatoms (as opposed to hydrocarbon compounds), or both are excluded from analysis/comparison. In one aspect, the method comprises assessing whether the geologic unit is characterizable as a geologic unit (tight formation/tight material), which similarly can exclude the use of such certain compounds or can be used to determine if direct analysis of measurements vs. ratios can be used in comparative analytical methods. In certain embodiments such a characterization can be performed as an additional early step of the methods described herein. In an alternative embodiment, such a characterization can be obtained separately from the application of the specific sample collection and analysis steps described herein.

The type of geologic unit can, in some aspects, contribute to at least two decision points related to the application of the methods described herein.

In some aspects, the type of geologic unit can determine whether directly measured compound values can be used as opposed to the alternative option of using ratios of compounds in the analysis. In certain aspects, directly measured compound values are used in an analysis despite the characterization of the type of geologic unit. In certain aspects, ratios of two or more compound values are used in an analysis despite the characterization of the type of geologic unit. In certain aspects, directly measured compound values are used in geologic units having only particular type characterization(s). In certain aspects, ratios of two or more compound values are used in geologic units having only particular type characterization(s). In certain aspects, in scenarios where the characterization of the type of geologic unit is deemed to be relevant to the selection of comparators, a ratio of (a) a first single, directly measured compound to a second, single, directly measured compound; (b) a first sum of two or more directly measured compounds to a second sum of two or more directly measured compounds; (c) a total of a first group of directly measured compounds to a total of a second group of directly measured compounds; (d) a total for a first complete class of directly measured compounds to a total of a second complete class of directly measured compounds; or (e) any combination thereof is used in an analysis (such as, e.g., ratios exemplified in Example 5, wherein paraffins are compared to the sum of paraffins and naphthenes, or, e.g., paraffins are compared to the sum of paraffins and naphthenes while excluding C5 pentanes). Similarly, in aspects in scenarios where the characterization of the type of geologic unit is deemed not to be relevant to the selection of comparators, one or more of ratios (a)-(e) are used in an analysis.

For example, in tight conventional formations or, for example very specifically, "resource plays", where fluid is removed directly from a resource as opposed to removing it from the ground after it has migrated to a new location from its original source, direct quantitative compositional matching (e.g., direct measurement of compounds and comparison of the same) can in some cases be possible, as the quantitative amount of each compound should not be significantly altered. In other examples, be they conventional or unconventional plays, the geological material may hold fluids in a way that allows some species to have their absolute concentrations compromised. In aspects where absolute concentrations may be compromised, the geologic material may be able to maintain a representative composition relative to other compounds and thus in such cases, relative ratios of two components can be incorporated into the method. In certain aspects, relative ratios can be a more appropriate analysis in scenarios where absolute concentrations of one or more compounds may be compromised. As an example, if one has two compounds in which their respective quantities is at risk of being modified due to the type of resource from which they are sampled, however the two compounds are similar enough such that their respective quantities are expected to be impacted in a similar enough way such that their quantities relative to one another, that is their ratio, should be detectibly or significantly unaltered, a ratio can be used in place of an analysis using their direct measurements.

In some aspects, the type of geologic unit will determine which compounds may be most appropriate to use in analysis. While much is known about the interaction of various hydrocarbons and the affect different types of rock have on them, the analysis of which two or more compounds are likely to be affected by the rock of a particular resource from which they are sampled can be multifactorial, nuanced, and challenging. Much literature in the field describes such interactions and those skilled in the art are familiar with the challenges such interactions can present.

As one example, it is known that rock from a geologic unit high in quartz would not be suitable for the use of aromatics in such an analysis, as the aromatic hydrocarbons would be significantly affected by the presence of quartz, such as rock having about 20% quartz content or higher, such as approximately 18%, approximately 16%, approximately 14%, approximately 12%, approximately 10% or in some cases is may be that rock having a quartz content of approximately 8%, approximately 6%, or approximately 4% or higher may make the use of aromatic compounds unsuitable for the methods described herein. In certain aspects, rock having a quartz content less than about 6%, less than about 5%, less than about 4%, less than about 3%, or less than about 2% content of quartz may make the use of aromatic compounds in the methods presented herein acceptable for use as the impact such a presence of quartz may have on analysis of aromatic compounds may be such that it does not significantly impact the results of the analysis and the utility thereof.

Beyond the characterization of the geologic unit and the rock of which it is comprised, the specific characteristics of a compound impacting how it fractionates can also be relevant to the selection of the most appropriate compounds for analysis, such characteristics being described elsewhere herein. According to certain embodiments, two or more compounds are selected for analysis which are substantially similar in nature both in the way that they interact with various types of rock but also in the way two or more compounds fractionate. The way two or more compounds fractionate can impact their relative direct measurements relative to one another and hence can skew a ratio of the two so as to make use of such a ratio unsuitable for the method. In some aspects, two or more compounds should be chosen which are not different enough so as to cause one to have its absolute amount to be altered to a degree significantly different than that of another.

According to certain aspects, the number of carbons, the size of the compounds, a compound's boiling point, the solubility of the compound in water, the polarizability of the compound and the like are exemplary characteristics which can each, alone or in combination, impact the way one compound fractionates or interacts with a particular type of rock, either alone or relative to any other.

In some aspects, for example, use of compounds to establish a ratio applied within the methods described herein should be selected which have a boiling point which does not differ by more than about 20 degrees Celsius ($^\circ$ C.) in boiling point, such as for example not differing by more than about 18$^\circ$ C., more than about 16$^\circ$ C., more than about 15$^\circ$ C., more than about 12$^\circ$ C., more than about 10$^\circ$ C., or even more suitably by more than about 8$^\circ$ C., by more than about 7$^\circ$ C., more than about 6$^\circ$ C., or more than about 5$^\circ$ C.

In some aspects of the present invention, certain interactions a selected compound could have with a rock should be avoided. In certain aspects, any compound selected for use within a ratio used in the methods described herein can be interactions such as but not limited to pi-stacking, dipole-dipole (also sometimes described as polar-to-polar interactions), ionic, and hydrogen bonding interactions which result in a modification of the measured quantity of the compound of preferably not more than about 20%, preferably not more than about 18%, preferably not more than about 15%, preferably not more than about 12.5%, preferably not more than about 10%, preferably not more than about 7.5% or even less, such as preferably not more than about 5%, preferably not more than about 3%, preferably not more than about 2%, or even more preferably, interactions which do not result in a detectable impact on the amount of the compound. In aspects, a subset of any compounds selected, or all compounds selected, should avoid having any one or more of such interfering interactions to the appreciable extents described.

In aspects, a limited set of data points (e.g., fewer inputs) is used in method(s) for simplicity and focus (as compared to the prior art). In certain aspects, a limited set of data points facilitates the generation of actionable data in less time and at a lower expense than competing technologies such as, e.g., that previously described in the '807 publication and as is described by RevoChem. In certain aspects, about 2-20 compounds, such as between about 2-16 compounds, e.g., about 2-10 compounds (e.g., between about 2-8, 3-8, 2-7, 3-7, 4-8, or between about 4-7 compounds) are selected from a group of less than about 150, such as less than about 125, less than about 100, less than about 80, or less than about 60 compounds are utilized in the analytical methods of the invention. According to certain embodiments, the selection of compounds can be made with that aim of decreasing the risk of loss of one more than another as a function of interfacing with rock from a geologic unit or sample preparation during the analysis process. In aspects, the alkanes and cycloalkanes of C6 hydrocarbons, C7 hydrocarbons, and C8 hydrocarbons are included in an analysis. The relative weak London dispersion forces of alkanes result in gaseous substances for short carbon chains, volatile liquids with densities around 0.7 g/mL for moderate carbon chains, and solids for long carbon chains. Such differences in physical states can occur because of a direct relationship between the size and shape of molecules and the strength of the intermolecular forces (IMFs). In certain aspects, as discussed elsewhere herein, analytes are selected which are not impacted by the presence of oil-based muds, such that the methods herein can be applied to operations in which oil-based muds are utilized.

According to embodiments, one or more ratios of two or more compounds of two (or more) different classes are determined as a way of characterizing a non-fluid sample, a fluid sample, or both fluid and non-solid samples, and in some embodiments the method comprises comparison of at least one ratio of such compounds of two different classes from the non-fluid sample(s) and the fluid sample(s). In one embodiment, one class is an acyclic compound, and the second class is a cyclic compound. In one embodiment, one class is a branched compound, such as a branched hydrocarbon, and the second compound is a normal (non-branched/linear) hydrocarbon. Skilled persons will be able to identify other similar different classes of compounds that can provide useful comparative ratios within a single sample source (e.g., non-fluid sample(s) or the fluid sample(s)).

The compounds compared within/from each solid (non-fluid) and fluid (e.g., liquid) sample, and, further compared across solid and fluid samples (e.g., as compounds or ratios of compounds present in solid samples compared to compounds or ratios of compounds present in a fluid sample) will typically be similar to one another, if not identical, in methods comprising the comparison of such amounts of compounds or ratios of compounds between the two samples. For example, a comparative analytical method can comprise determining the amount of compound A, which is an acyclic hydrocarbon, such as an alkane, and compound B, which is a cyclic hydrocarbon, such as a cycloalkane, in solid samples and comparing that ratio to a similar ratio of similar compounds in the liquid sample(s).

According to certain aspects, two or more compounds that are more similar in nature than different can be selected for comparative use in the methods described herein (e.g., in at least one part of a ratio as measured in the solid sample(s) and the fluid sample(s) of a comparative method). Thus, for example, where compound A/compound B ratio is determined in the solid samples, as described in the preceding paragraph, the fluid sample(s) can be analyzed for the amount of compound A'/compound B', wherein compound A' is of a similar nature as compound A (in this case both being acyclic hydrocarbons) and having −2/−1 to +1/+2 carbon atoms to compound A, especially where both compound A and compound A' comprise more than five carbon atoms, and compound B' is similarly of the same or related class as compound B and similarly within −1/−2 to +1/+2 carbons in carbon composition, preferably where compound B and compound B' both comprise at least five carbon atoms. In some aspects, similarity of compounds is determined on experimental analysis, based on previously published and available literature within the art, based on select characteristics such as those described herein, or any combination of any or all thereof. Alkanes and cycloalkanes of the same or close carbon number (e.g., within 1 carbon, or for example within 2 carbons in the case of larger hydrocarbons), while having different properties, are far more similar in properties than, for example, methane and ethane and thus, in comparing their ratio at a given position, assuming that there are not processes leading to significant variations in fractionalization, the use of alkanes and cycloalkanes of C6-C8 hydrocarbons in the methods described herein reduce the risk of compound interference (and thus, ratio errors) due to rock properties, making for suitable compounds in many common scenarios.

Water can slowly change the composition of a collected sample. E.g., more soluble chemicals can go into water phase more quickly. This is a characteristic which can affect lighter hydrocarbons to a greater extent than heavier ones, as lighter hydrocarbons are more soluble in water than heavier hydrocarbons. Hence, in certain embodiments, analytes to be measured and used for comparing fluid samples to non-liquid samples are chosen based on the known or predicted level of water contamination of a sample so as to minimize the impact of the presence of water in the sample on any absolute amount or ratio of analytes measured.

In circumstances where samples are not known to be high in water content, samples can be analyzed within any reasonable period of time so long as they are properly protected from contamination or loss. For example, collected fluid/gas samples can, in some aspects, be tested within about 6 months, such as within about 5 months, within about 4 months, within about 3 months, within about 2 months, or even for example within a shorter period of time such as within about 1 month, within about 3 weeks, within about 2 weeks, or within about 1 week, such as for example within about 6 days, within about 5 days, within about 4 days, within about 3 days, within about 2 days, or within about 1 day of collection, or even less, such as within about 18 hours, within about 12 hours, within about 6 hours, within about 2 hours, or even less, such as within approximately 1 hour of collection, as in, for example, within between about 1 day-about 6 months, within about 1 day-about 5 months, within about 1 day-about 4 months, within about 1 day-about 3 months, within about 1 day-about 2 months, or within about 1 day-about 1 month, such as for example within about 1 hour to within about 3 weeks. In certain aspects, if it is known that samples comprise a higher-than-normal amount of water (e.g., the sample has a high water cut), testing the sample within a shorter period of time is preferable so as to reduce the impact of water solubility on the target analyte content. In such cases it can be preferable to analyze the sample within about 3 months of collection, such as for example within about 2 months of collection, within about 1 month of collection, within about 3 weeks of collection, within about 2 weeks of collection, or within about 1 week of collection, such as within about 6 days of collection, within about 5 days of collection, within about 4 days of collection, within about 3 days of collection, within about 2 days of collection, within about 1 day of collection, or within a matter of hours of collection, such as within about 18 hours, within about 12 hours, within about 6 hours, within about 2 hours, or even less, such as within approximately 1 hour of collection.

Analysis of non-fluid samples by the method can be tested within a similar period of time, but as noted, typically such samples are also typically hermetically sealed promptly upon collection (e.g., within about 40 minutes or less, within about 12 minutes or less, within about 5 minutes or less, or within about 3 minutes or less).

According to certain embodiments, methods described herein can be used to aid in decision making prior to well completion. In such cases, the analysis timeframe for sample analysis can be impacted by the timing for well completion as much as or more than the stability of the samples. For example, in many cases, in completing a horizontal well, a matter of days may be the window of time within which data from the methods described herein could be used to aid in decision making on how to complete the well. In such cases, the utility of the present method is particularly highlighted as the methods provided herein can be completed quickly, e.g., within a matter of hours. Other technologies which theoretically could be applied during this pre-completion period in order to produce insights on how to proceed with well completion can take much longer and hence are often not suitable for such a purpose.

In Example 1 provided herein, the ratios of the alkanes to cycloalkanes (alkane/(alkane+cycloalkane)) for species consisting of the same number of carbon atoms were used. In Example 1, the ratios of 6, 7, and 8 carbon alkanes and cycloalkanes were used, though this process could be extended to higher carbon number hydrocarbons, or other classes of molecules.

In some aspects, in using the extraction and quantification methods disclosed in the SMITH Art, the analysis can be limited to comparison of non-aromatic linear and cyclic organic compounds. In certain embodiments, and in particular scenarios, this analysis may not be suitable for use with certain hydrocarbons such as aromatics. Aromatic hydrocarbons have previously been shown to have a set of interactions with geological material different than that of alkanes or cycloalkanes in that the conjugated pi bond systems interact with silica containing minerals. Such interactions have been observed in experimental work known to inventor Christopher Smith. However, in alternative embodiments, for example, in a reservoir with minimal silica content, such as for example a carbonate reservoir, it may be possible to consider aromatic species for use within the methods of the present invention. As noted previously, in aspects, the method comprises analyzing whether there are high quartz content materials in the second sample and, in such cases, excluding measure/comparison of aromatic species or assigning a lower weight to the comparison of aromatic species comparisons. In aspects where such materials are detected, aromatic species are not compared in the method.

In certain embodiments, use of heteroatom molecules (hydrocarbon molecules where at least one atom has been substituted for a non-hydrogen or carbon atom), are excluded from the analyses utilized in the methods described herein. Heteroatom molecules are known to undergo interactions with the surfaces of silica containing minerals which can make them unsuitable candidates in some cases, as the level of their presence, or alternatively the lack thereof, can be skewed by their interaction with the rock material with which they interface.

In certain aspects direct measurement of, or ratios comprising relative amounts of, chlorine, bromide, strontium, water deuterium, water oxygen, sulfur, iron, and the like are excluded from consideration within the methods described herein. Further, according to certain embodiments, the direct measure of, or ratios comprising relative amounts of, sulfur or hydrogen sulfide are excluded. In some aspects, the direct measure of or ratios comprising aromatics are excluded from the analysis described herein. In alternative aspects, methods herein comprise the comparison of aromatics, such as, e.g., aromatics in liquid samples to aromatics of non-liquid samples. In certain aspects, 1 aromatic compound is compared to the sum of 1, 2, or 3 aromatic compounds. In aspects, the comparison can be between the same or similar aromatic compounds, e.g., those compounds sharing carbon composition-similarity or structural-similarity.

In aspects, either directly measured values or ratios of two or more hydrocarbon species can be selected to relate the reservoir composition in non-fluid samples to the fluid sample, or in a second or further additional fluid sample(s) to a first fluid sample. If ratios are selected, such ratios can be calculated for each analyzed sample (fluid or non-fluid).

Mathematical Analysis & Spatial Weighting

In some embodiments the method of the invention comprises performing one or more mathematical analyses that help to identify applicable allocation or specific location characteristics as discussed herein, such as, e.g., the portions of a well that are contributing oil or that will contribute oil to oil production. Typically, in performing the mathematical analysis step of the methods described herein, a description of the geologic site, e.g., well, or more specifically a well bore, is constructed utilizing the measured values of compound(s) determined at different positions within the well by way of the solid samples (in some embodiments such information is also or alternatively obtainable, at least relatively, from liquid samples, wherein the region from which liquid sample(s) are obtained is known). In some aspects, positions of a well (zones) are selected based on knowledge of the completion design or available samples (e.g., available sampled positions). This will be further described by way of example elsewhere herein.

In some embodiments according to certain scenarios, interpolation of the composition at a given position from neighboring sampling positions may be required and can be implemented. That is, across a span of a well, samples may not be available for every desired location. In aspects, under ideal circumstances, evenly spaced, accurately timed sample collection is conducted such that samples are collected across evenly spaced intervals representative of the full length of the well. However, in actuality, it is often the case that gaps exist within a series of sample collection, or also or alternatively samples are collected in an uneven manner across the length of a well. In aspects it can be important to know how each location within the well contributes, and accordingly it can be important to appropriately establish representative sample values across the length of the well. Because of the variation in sample collection, it may be necessary to "fill in the blanks" in short gaps in sample collection using the data collected just before, and just after, that spatial gap. This gap-filling step can be done by, for example, averaging the values before and after a gap. In aspects, establishment of appropriate representative intervals can be accomplished based on the availability of samples as well as the length of the well and the required specificity of result data. It is important, however, to recognize that if sample data fed analyzed is representative only of every, for example, 50 feet of a 300 foot well, it is unreasonable and inappropriate to expect a resolution any greater than that.

To exemplify such an interpolation, the following scenario is provided: If a 1000 foot (ft) span of a well is sampled at 50 ft intervals, and the sample at position 350 feet is missing, one can interpolate the value of the sample at 350 feet based on the characteristics of surrounding samples. Alternatively, if a practitioner determines that a gap in samples is large enough that an interpolation approach is inappropriate or unwanted, in aspects the weight of the contribution assigned to the two neighboring samples could be increased to account for the missing data point(s) in the gap. An appropriate analysis can also take into consideration that it is possible for "edge cases" to exist, where an/the interval may be shorter than desired and the weighting contribution from this interval would need to be suitably decreased to reconcile a model of a method.

Mathematical Analysis: Application of Numerical Method Engine (NME)/Weighting Factor/Executing the NME According to certain aspects, an analysis is performed that seeks to determine the required contribution at each position of a site/location samples to produce the composition of the product (e.g., the composition of the fluid). In aspects, the output of such an analysis is a description of the relative contribution of each analyzed location within the well to the composition of a produced fluid. In scenarios whereby fluid from a geologic site is different from the geologic site from which solid (non-fluid) samples are collected is utilized in the method, the output of such an analysis is a description of the relative contribution of each analyzed location within the well to the composition of the fluid expected to be produced from the well. In aspects, the analysis performed as part of the method a) proposes a contribution value to each position; b) calculates what such a proposal would yield in terms of a product in comparison to that of the known fluid; c) modifies the contribution values of one or more positions; d) recalculates what such a proposal would yield in terms of a product in comparison to that of the known fluid; e) continues to repeat steps (c)-(d), typically until the analysis is unable to obtain proposed contribution values from each position that yields a closer description of the known fluid. In aspects, such an analysis can, as will be described, be performed programmatically, e.g., by a computer and computer software, manually, or both. In aspects, such an analysis can be accomplished by a method that comprises use of a numerical method engine ("NME"). A numerical method engine can be used to generate and execute such an analysis. In some places herein, use of the term "numerical method" may be used to refer to such an analysis. A numerical method is a mathematical tool designed to solve numerical problems and there are many suitable numerical method engines which can be employed for aiding in generating and executing numerical methods. One example of a suitable numerical method engine is available via the programming aspect of EXCEL, where utilization of EXCEL's Visual Basic for Applications (VBA) functionality known as "Solver" allows a user to employ a wide variety of numerical methods such as those which can be used in the methods described herein, with results fed back to the user in spreadsheet form. Such results can be graphically presented for ease of interpretation. In aspects, programs such as MatLab, SpotFire or other tools, software programs, applications and the like having similar or equivalent mathematical functionality can similarly be utilized in the methods herein. E.g., in aspects the invention provides methods comprising use of a computer having physical, reproducible, and transferrable computer readable media comprising instructions for carrying out such mathematical functions and processor(s) that read and apply such data to obtain output, which can include control of devices/interfaces (e.g., display of data/messages, relaying alerts, sending email/text messages, or controlling other analytical devices, fluid production devices (e.g., oil well devices), or some combination thereof.

In aspects, such data analysis and data processing can be directed by a human using software applications described herein. In aspects, such data analysis and data processing can be performed in an automated fashion using a computer, whereby one or more computers (a) receive data; (b) process data; (c) present data in processed form with little to no input from a human being. In aspects, such computer(s) can be in communication with analytical instrument(s) performing the analysis of the compound(s) described herein, and the computer(s) can receive data directly from such instrument(s) and automatically process such data in order to provide analyzed results in a semi-automated or automated manner.

In aspects, methods other than numerical methods or numerical method engines can be utilized. One can appreciate that use of numerical methods/numerical method engine to programmatically iterate values into variables of a defined equation can be preferable for reasons such as processing speed, accuracy, and the like. In aspects, specific equations, e.g., complex algebraic equations, may be developed which could be capable of solving individual position contribution(s), the use of which applied in a system of equations approach. The application of such an approach, while complex, is not outside of the realm of possibility and hence can be an aspect of the invention.

In some aspects, the mathematical model, that is the analysis, consists of each of the selected, more than one, compositional parameters (either ratios or directly measured values, as appropriate) times a scaling factor. In aspects, an initial scaling factor is applied to provide the mathematical model a scenario from which to start. In aspects, the initial scaling factor can be any initial scaling factor, a scaling factor applied to each ratio or directly measured value, or, alternatively, to values representing intervals and/or interpolated values representing interval, as a starting point for the analysis. In aspects, the sum of scaling factors applied to each compositional parameter (e.g., representative ratio) totals a pre-defined total value, such as 1 or 100% representing the total length of a well (though other arbitrary numbers can be applied under applicable circumstances), such that, for example, each compositional parameter (e.g., ratio representing an interval) is scaled to represent a fraction of the total. In certain aspects, even non-sensical random numbers can be applied as initial scaling factors, as such scenarios can in some aspects be helpful in testing the mathematical model to see if the same result can be obtained using such different starting factors (e.g., the same convergence point can be reached). "Convergence" in mathematics in simplistic terms is the property of approaching a limit more and more closely as a variable is changed. A "convergence point" as used here is the point at which regardless of what initial scaling factors are provided, the mathematical model continuously provides or approaches the same summed composition across all ratios of analyzed solid samples (or their representative values used in analyses) that best matches the combination of ratios from a fluid. In aspects, the mathematical model starts with a scaling factor representing the relative contribution of an interval to the final produced product; e.g., is initially established as a representative of that interval's spatial contribution to the total well length being considered, but such a scaling factor can be set as a variable during the analysis such that the best fit profile for each position's relative contribution to the final product is established.

In aspects, an initial scaling factor is derived from the partitioning of a site from which samples are collected into zones or intervals, whereby such zones or intervals may or may not be evenly assigned (e.g., uniform). In aspects, each zone/interval can be assigned a numerical value representative of that zone/interval's spatial contribution to the total well length being considered and used to adjust the ratio or directly measured value such that a ratio or directly measured value is over- or under-valued in terms of its (potential) relative contribution. In aspects, a data set (e.g., data from all samples used in an analysis and the intervals associated therewith) can comprise a single initial scaling factor applied to all assigned intervals. In aspects, a data set can comprise intervals whereby one or more intervals has a different initial scaling factor assigned than that of any other one or more intervals. In such aspects, two or more intervals can share the same initial scaling factor. In aspects, two or more intervals (of a data set) can have different initial scaling factors applied to them.

The term "interval" refers to a span of distance over a geographically defined area. In aspects the term "interval" can refer to a segment of a geographic unit. In aspects, the term "interval" refers to a distance between points of sample collection; e.g., a sampling interval can be 60 feet, whereby samples are collected every about 60 feet across a well depth/length. In aspects, the term "interval" can be used interchangeably with the term "zone", such a use referring to a unit of length used to divide or partition a site (e.g., divide the full span of a well), such that a span of a well, for example, is divided into 5, 10, 15, 20, 25, 30, 35, 40, 45, 50, or more intervals. In aspects, the shorter the interval of sample collection, the shorter the intervals into which the span of a site (e.g., well) can be divided. In aspects, each interval of a site having the same length is assigned an equal weighting in the analysis of the method(s) herein. In aspects, an interval having a length which is, e.g., less than others of the analysis, is assigned an initial scaling factor such that its difference in size (e.g., length, distance) is not under- or over-valued.

If the knowledge of the well completion and the interpolated positions cannot be easily reconciled, then the applied initial scaling factor can be adjusted to account for the difference. For example, if the well is "modeled", or established as being described by, utilizing 60 ft intervals, and the completed section of the well was 250 ft, there would be five intervals: 4 intervals of 60 feet each, and one interval of 10 feet. In aspects, that 10-foot section can have an initial scaling factor appropriately adjusted to reflect that the interval was ⅙ of the standard 60-foot interval. In aspects, interval length can be selected based on sampling intervals while keeping in mind the available resolution of the measurement. This initial scaling factor will be less than one and will remain less than one even after the application of analyses in which iterations of the scaling factors are applied and ultimately selected as described herein. The summation of the compositional signatures at each position after completing of the analysis described herein can in aspects result in a value similar to that of the measured end product.

According to aspects, a method comprises the establishment of the initial scaling factor as described, and using the initial scaling factor, a mathematical model is executed to identify the best fit profile, allowing the scaling factor to be variable. The result of the analysis can be a mathematically determined "best fit" profile, allocating a contribution level of each position and its representative compositional parameter (e.g., ratio) to the produced fluid. For the purpose of data quality and confidence in the determined result, the starting (initial) scaling factor(s) can be adjusted, and the mathematical model executed again. The goal of such a second execution is to determine if providing different starting points allows the model to identify a profile of allocation that provides a better fit to the produced fluid. This process can be repeated multiple times, each time starting with a different scaling factor or set of scaling factors, until confidence is reached that the best fit profile has been obtained. In aspects, the methods herein comprise running the mathematical model at least about 2, at least about 3, at least about 4, at least about 5, at least about 6, at least about 7, at least about 8, at least about 9, or at least about 10 times or even more. In aspects, the results of such analysis can be compared to one another to determine the optimal profile which results in the residual sum of squares from comparing the ratio values obtained from the produced oil sample (liquid sample) versus the total ratios (sum of scaling factor*ratio at a given interval) of the non-liquid (solid) samples approaching or equaling zero. This is described further elsewhere herein. In aspects all such analysis can be automated, e.g., performed, analyzed, re-executed, re-analyzed, etc. using computer(s) and software with little human intervention. This is described elsewhere herein. In aspects, a computer can comprise executable code directing the (a) establishment of initial scaling factor(s); (b) execution of the mathematical model; (c) recording of the residual sum of squares value; (d) assignment of new scaling factors; re-execution of the mathematical model; (e) recording of the second residual sum of squares; comparison of the residual sum of squares; (f) determination of which profile provides the lowest residual sum of squares; (g) recording or maintaining the lowest residual sum of squares and the associated profile identified; and (h) repeating steps (d)-(g) until a stopping point is reached, such a stopping point being human intervention or, for example, pre-programmed stopping points such as but not limited to (i) a point at which a pre-determined number of comparative iterations has been performed or (ii) a point at which a predetermined number of profiles is identified (consecutively or non-consecutively) which differ from one another by no more than a predetermined amount, e.g., by less than 3%, less than 2%, ≤1%, ≤0.5%, less than ~0.1%, or less than ~0.05%, or less than ~0.01% from one another.

In aspects, automated methods can comprise an element of human oversight. The nature of mathematical models is such that in certain scenarios, a mathematical model can identify a best-fit profile which, in considering the real-world scenario, does not make sense or is not feasible. (e.g., the mathematical model identifies a single location across the span of a well contributing 100% to the production fluid). In these scenarios, a human check for non-sensical results can be helpful. In aspects, machine learning can be applied in such scenarios. In aspects, machine learning (e.g., artificial intelligence (AI)) can be applied to any of the analytical processes described herein, such that over time a computer, software, or system can learn such things as (a) how to establish initial scaling factors; (b) how to provide alternative scaling factors; (c) how to evaluate results of an executed mathematical model; (d) how to determine how many times to execute a mathematical model with different starting scaling factors; (e) how to compare the residual sum of squares from multiple analyses to determine the best fit profile, and the like, using a machine learning model/process adapted from known methods. In aspects, computer(s) and computer software, including machine learning applications, can also or alternatively be applied earlier in the method such as participating in the selection of the appropriate compound(s) for analysis or the appropriate ratio(s) to utilize in the methods herein. Machine learning models suitable for such applications can be based on neural network method approaches to find patterns in data based on neural network training of the applicable model(s). Other machine learning models and approaches are known, and any suitable combination of model and architecture can be applied.

The iterative analysis of possible position or interval weights which best contribute to an overall profile closest to that of the fluid sample, can be executed with the initial scaling factor at each position being set as an adjustable variable. In aspects of the analysis, many iterations of each initial scaling factor are tested to see which combination of final scaling factors, as assigned to each interval (or in alternative embodiments to each specific sample indicating a specific location), best yields a summed composition across all ratios that best matches the combination of ratios from the production fluid, such data then being indicative of the relative contributions of different intervals of the well to a produced fluid. The term "profile" is sometimes used herein to describe the summed composition across all ratios that (ultimately, e.g., multiple iterations of profiles may be identified as part of identifying a final profile) best matches the combination of ratios from the production fluid. The use of the term "profile" used herein in this context should not be construed as describing a "matching" of the produced fluid composition to similar points along, e.g., a span of a well as determined by the analysis of non-fluid (e.g., solid) samples or fluid samples, as it is the contributions along the span of a well, and how they contribute in sum to the total, that is relevant to the methods described herein. In aspects of the analysis, many iterations of different starting scaling factors are tested to determine which combination of final scaling factors, as assigned to each interval (or in alternative embodiments to each specific sample indicating a specific location), best yields a profile closest to that of the fluid, such data then being indicative of the relative contributions of different intervals of the well to a produced fluid. In aspects, the aim of such sets of iterations is to identify a convergence to a point at which no better profile can be identified, and the best profile identified is obtained using multiple initial scaling factors. In aspects, the repeated iterations with differing initial scaling factors is utilized as a data quality or data validation step.

In certain aspects, a mathematical model can generate non-sensical results. Accordingly, in aspects, as described elsewhere herein, human consideration or also or alternatively an AI/machine learn method can be applied to address circumstances wherein mathematical model-generated results are evaluated for real-world applicability and accepted or rejected accordingly.

In aspects, an analysis performed by methods hereof can be subjected to further focusing, refinement or investigation/modulation. In one aspect, variables at each position can be focused by setting the different summed compositional parameters in opposition to each other, e.g., considering the residuals of the summed modeled parameter versus the directly measured parameter from the fluid (e.g., the "end product"). The use of the term "residual" as used here is the comparison of, that is, the difference between, each individual ratio modeled versus that measured in the fluid. To avoid bias in the analysis towards larger ratio values, the residuals can be divided by the ratio of the fluid values. This normalizes the residuals. The normalized residuals can in turn be squared and these squared residuals summed. The analysis can then, in specific embodiments, iterate though possibilities seeking the combination of variables which results in a sum of the squared residuals value which approaches 0. Similar approaches for multivariable models are known, and a numerical method engine can be useful for such calculations (though, as discussed, other methods may be applied). In a further aspect, the analysis can be focused/refined by restriction, such as for example when locations within the well where the well is completed with screens is known, the analysis can be restricted to the analysis of intervals only within such accessible areas, since those are the only areas of the well which could contribute to the fluid. Further optimization can be accomplished by placing a constraint on the scaling factor, e.g., the sum the scaling factor variables at all positions equaling approximately 1.

For the purpose of illustration, descriptions of the analytical method sometimes only comprise use of hydrocarbon compounds. However as has been described herein, method(s) of the invention are not limited to such compounds. As previously stated, compound(s) can be selected according to the aims of the analysis.

In aspects, as has been previously described, the use of alkane and cycloalkane compounds (e.g., C6, C7, and C8 alkane and cycloalkane compounds) are appropriate for accomplishing the goals of the methods described herein. In aspects, an analysis can be established, that can be described or abbreviated as: $P/(N+P)$ $Cn_i$ where "P" represents alkanes, "N" represents cycloalkanes, and "$Cn_i$" represents the number ("n") of carbons ("C") at a depth position ("i"), having a scaling factor ("SF") at each well depth ("i"). In aspects, such ratios are established and applied in the performance of the method(s) herein to determine relative productivity contribution to a produced fluid being made from each location within, e.g., a well.

In certain embodiments, the $P/(N+P)$ ratios are generated from the directly measured values of the hermetically sealed samples. The $P/(N+P)$ ratios for the different Cn values are not directly summed. Equation 1 shown below in Table 1, is an exemplary basic model at a given position or representative interval in the borehole of the well. Equation 2 of Table 1 demonstrates how the different positions can be combined to produce the "modeled product", that is the value obtained by considering all positions together, abbreviated "mp". Equation 3 of Table 1 demonstrates the condition the model is optimized against, where the model product can be equivalent to the "end product", abbreviated "ep", which is based on direct a direct measurement of the produced fluid. Equation 4 represents a constraint that can be applied to the analysis, e.g., applied to the model, to further optimize the fit in order to obtain a more accurate result, and represents that the sum of contributions from the scaling factor can be approximately 1. Again, in this model SF at i position is variable that is being optimized via numerical methods attempting to achieve the condition illustrated in Equation 3. Table 1 provides exemplary modeling equations with a brief translation to aid in understanding.

TABLE 1

Modeling Equations

| # | Modeling Equations & Simple Description |
|---|---|
| 1 | $SF_i*[P/(P + N) C6_i, P/(P + N) C7_i, P/(P + N) C8_i]$<br>(scaling factor) × [(alkane/alkane + cycloalkane<br>ratio for C6), (alkane/akane + cycloakane ratio for C7),<br>(alkane/alkane + cycloalkane ratio for C8)], . . . at each position |
| 2 | $\Sigma\ SF_i*[P/(P + N) C6_i, P/(P + N) C7_i, P/(P + N) C8_i] =$<br>$[P/(P + N) C6_{mp}, P/(P + N) C7_{mp}, P/(P + N) C8_{mp}]$<br>Sum of (1) = modeled product value of the ratios of C6, C7, C8 |
| 3 | $[P/(P + N) C6_{mp}, P/(P + N) C7_{mp}, P/(P + N) C8_{mp}] -$<br>$[P/(P + N) C6_{ep}, P/(P + N) C7_{ep}, P/(P + N) C8_{ep}] = 0$<br>modeled product value of the ratios C6, C7, C8 can be set to match<br>or be optimized against end product (actual measurement of fluid/gas) |
| 4 | $\Sigma SF_i \approx 1$<br>constraint that can befit to the model |

In aspects, each modeled product value can be directly compared to the end product value. Such values are characterizable as residuals. In aspects, the residuals can be normalized against the starting end product value (divided by the end product value) to prevent overweighting by the consideration of how relatively large the residual is. In aspects, these normalized residuals are squared and subsequently summed. The mathematical model performs iterations in attempts to reach a "0" optimal residual sum of squares, or the closest it can get thereto.

In practice, use of, and related inputs to, a numerical method engine can be summarized as follows:

Preparation (Prior to Analysis)

a. Data collection: a table of data is collected comprising:

i. the actual data points from sample collection and analysis including:

1. well depth at which the sample was collected;

2. hydrocarbon species results (directly measured values) for both the fluid (e.g., produced fluid) (e.g., whole oil) and the non-liquid samples representative of a plurality of well depths; and 3. calculations of ratios of interest using the hydrocarbon species results of (a.2); for example, if the hydrocarbon species of interest are C6-C8 alkanes and cycloalkanes, the following ratios as exemplified above can be calculated and included in the table:

a. C6 alkane/(alkane+cycloalkanes);

b. C7 alkane/(alkane+cycloalkanes); and c. C8 alkane/(alkane+cycloalkanes); and ii. data useful for restricting the model, such as identification of the positions of the well which are open and accessible (e.g., where the casing has been opened and the well has been completed with screens) versus where blanks within the well exist (sealed casings) and the well is inaccessible. Only those areas of the well where the casing has been opened with screens are relevant to this method and therefore the analysis can be restricted or constrained by such areas accordingly.

b. Establishment of well zones:

i. length of the well is divided into sections and each section assigned a representative value to be used in the model using the average of the sample data falling within that zone; and ii. each zone assigned an initial scaling factor based on the amount of spatial representation that zone has to the entire well; such as, for example:

1. if the span of the well being considered is 100 feet, the length can be divided into 10, 10 ft zones;

a. each zone is given an initial scaling factor of 0.1, as each zone represents one tenth of the span being considered;

2. if the span of the well being considered is 100 feet, the length can be divided into 5, 20 ft zones;

a. each zone is given an initial scaling factor of 0.2, as each zone represents one fifth of the full length of the well; and 3. if the span of the well being considered is 100 feet, the length can be divided into 12, 8-foot zones, however:

a. if this is the scenario, one is left with one additional zone which is 4 feet long, or half of a normal zone; and b. the 12, 8-foot zones would be given an initial scaling factor of $1/13^{th}$ of the total well (about 0.08), and the final 4-foot zone would be given an initial scaling factor of ½ the normal scaling factor (about 0.04).

c. Calculation of scaled values:

i. the averaged values from step b.i are then multiplied by the scaling factor of the zone to obtain a scaled or weighted value.

Analysis d. Execution of the NME:

i. the values from c.i can then be fed into the analysis, along with model constraint data from a.ii (and any other available or applicable constraint data) with the scaling factor assigned as a variable such that the aim of the analysis is to solve for a set of scaling factors, e.g., a scaling factor for each zone, which results in a relative contribution well profile across the length of the well which, when all contributions are taken together, best matches the composition of the known fluid (e.g., a produced fluid, the fluid serving as the sample for which a sourcing profile analysis is desired).

ii. The initial scaling factors can be modified, and the execution of the NME repeated, with, again, the aim of the analysis being to find a best fit profile and then to optimize the assigned scaling factors, by allowing the scaling factor to be variable, such that the best fit relative contribution well profile across the length of the well is identified.

iii. Step d.ii. can be repeated any number of times to ensure data confidence, confidence reached when the same profile is identified yielding the lowest residual sum of squares value using different starting scaling factors; that is, until a better fit profile cannot be identified.

These steps are exemplary, and methods can comprise most, generally, or all of such steps, with the modification of variables to account for the applicable data.

Results & Interpretation

As described, a scaling factor, as calculated by the analysis for each input location and provided for each accordingly represents the relative contribution of that interval to the final produced product. In certain embodiments, these factors, when applied to a series of samples, can be used to identify the relative contribution of that represented interval, to the fluid; that is, what percentage of the fluid was contributed by the interval of the well.

In certain aspects, if the fluid were water, one could use the factors generated to determine which locations within a span of a well are making higher or lower contributions to the contaminant water; that is, what percentage of the water is coming from each interval.

In certain aspects, if only a single non-fluid sample is collected, the analysis element of the method is not required or applicable; one could simply say that the profile of the single sample is like-or-unlike that of the fluid.

According to certain aspects, application of the method(s) herein identifies the relative, e.g., the percent, contribution of each location/interval within a well to a produced fluid. In aspects, such a well can be positioned within, e.g., access, a single reservoir/compartment, and in aspects the methods herein identify the contribution being made at and/or by each location within the reservoir/compartment, accessible by the well, to a produced fluid. In aspects, the application of the methods herein to a single well can identify the presence of multiple compartments; that is, multiple compartments accessed by the well, in that the method is capable of detecting samples having distinctly different compound content or compound ratios representative of contribution to the well from multiple reservoir/compartments. In further aspects, the application of the methods herein within a single well can identify boundaries of one or more compartments within a well, such as for example identifying areas of a well wherein production levels significantly change, e.g., a transition point is notable whereby areas of little to no contribution is being made to a produced fluid are identified.

In aspects, the invention described herein does not comprise the Monte Carlo Iteration. In aspects, the method does not comprise any similar or equivalent analysis or method to the Monte Carlo Iteration.

Technology Applications

To provide context for the applicability of certain methods described herein, Table 2 is provided to summarize where and how such certain methods can find utility. Exemplary questions which the methods described herein are well suited to address have been provided, however such a list of examples should not be interpreted as limiting/limited.

According to certain aspects of the invention, the methods described herein can be used to characterize the production of a completed well. In further aspects of the invention, the methods described herein can be used to predict the production characteristics of a yet-to-be completed well, such that the method is capable of providing a prediction of the locations within a yet-to-be completed well which will likely contribute the most to the produced liquid or gas from that yet-to-be completed well. In certain cases, such a prediction can save significant operational costs in that such predictions can drive decision making related to completion design, such as, for example, in conventional plays, informing which areas of a well best for pipe placement and which are not; where a casing might be opened for access to a flow of fluid gas if present; or for example in unconventional plays, where one might set stages for explosives and how such explosives are used.

In some aspects of the exemplary scenarios described below, the methods of the present invention can be applied to characterize online production systems. In some aspects of the exemplary scenarios described below, the methods of the present invention can be applied to predict the characterization of wells yet-to-be-completed, yet-to-be-drilled, or yet-to-be-otherwise brought online.

As stated previously, in certain embodiments this technology can be applied to lateral wells in stacked plays. Stacked plays comprise fluids of differing compositions which can be reserved in reservoirs within different rock formations vertically, e.g., the different rock formations are "stacked" one above/below another. In such scenarios, knowledge of the not only lateral compositional changes across the lateral reservoir, from multiple laterals, can be important for determining relative contribution of specific well locations to a final produced fluid, but the changes across the vertical composition can be important as well. For example, in a simple case wherein there are only two formations representing different reservoirs, samples obtained from two laterals that were parallel and displaced vertically such that one is in the upper reservoir formation, and one is in the lower reservoir formation, in addition to the vertical well, could be very informative about relative sourcing of contributions being made to an analyzed fluid, e.g., a produced fluid such as a fluid essentially comprising an oil. In some embodiments, such vertical compositions can be included in the model, along with the horizontal compositions, in cases where the fluids in these different formations are in communication by systems such as natural fracture networks, artificially induced fracture networks, or a combination of such networks, with the bore hole from which a fluid, e.g., a produced fluid comprising an oil, is extracted. In certain aspects, such an analysis provides an opportunity to create a multidimensional map of an area and to provide actionable data of where relative contributions are coming from.

In aspects, the method(s) described herein can be applied to carbon capture storage, such as, for the example, the detection of leaks from such storage. In aspects, the method(s) described herein can be applied to the establishment of the migration volume of enhanced oil recovery carbon dioxide (e.g., migration of injected $CO_2$ can be detected in cuttings from new wells drilled following injection). In aspects, the method(s) described herein can be applied to geothermal wells such that method(s) find relevance in the mapping of geothermal reservoirs.

TABLE 2

| Exemplary Applications of Results of Analytical Methods of the Invention | | |
| --- | --- | --- |
| Scenario | Scenario Description | Exemplary Questions Method Can Address |
| 1 | Characterization of vertical wells in communication with several layers of rock; opened holes to multiple layers of rock | * Where contribution across multiple penetrated reservoirs is coming from; * Which reservoirs are being depleted; |
| 2 | Characterization of a heterogeneous lateral well; a lateral well which passes through multiple geological features, e.g., multiple faults | *Differences in the production across geological features; * Feature(s) effectively acting as its/their own reservoir having its own properties contributing to production in different ways; * Products being contributed by each feature vary in quality; |
| 3 | Characterization of a fracked unconventional reservoir wherein a vertical pilot exists along with landed laterals | * Vertical heterogeneity of the vertical pilot; * Product produced from what layer of rock as the fracture network is expanded and the vertical well is made available to liquid/gas from other layers of rock by means of cracks in the rock formed by fracking; * Other reservoirs of interest having potentially become available by fracking (estimation of what features/reservoirs the vertical well is now in communication with post-fracking); |

TABLE 2-continued

Exemplary Applications of Results of
Analytical Methods of the Invention

| Scenario | Scenario Description | Exemplary Questions Method Can Address |
|---|---|---|
| 4 | Vertical pilots in stacked reservoirs present comprising multiple landed laterals resulting in spatially distinct boreholes both in a vertical direction and a lateral direction | * Homo/heterogeneity of the area being drilled in both vertical and/lateral directions; * Lateral locations, in a lateral direction, contributing to the vertical well production; |
| 5 | Operational, online well monitoring | * How chemistry of a collected product is changing over time; * How performance of a well is changing over time; * Which sections of a well are becoming more or less productive; |
| 6 | Characterization of dry wells | * Should additional exploration/ drilling be considered due to cuttings from such a well sharing characteristics with that of nearby productive wells |
| 7 | Carbon capture storage assessment or monitoring | * If sequestered/stored carbon dioxide is leaking and if so, at what locations; |
| 8 | Enhanced oil recovery operations | * Migration characteristics of enhanced oil recovery $CO_2$ (e.g., volume) |
| 9 | Geothermal wells | * Mapping of geothermal reservoirs |

The invention thus provides methods that correspond to any of the above-described methods in Table 2. For example, the method provides a method of determining the performance of a well over time that comprises obtaining fluid samples over about two, three, four, five, seven, ten, twelve, or more time points (e.g., about 2-100, 2-60, 2-48, 2-36, 2-30, 2-24, 2-20, 2-18, or about 2-12 time points) and comparing the analytes of such fluid samples with corresponding analytes (e.g., a corresponding ratio of similar compounds to a ratio of compounds measured in the fluid sample) to determine changes in the oil well over the monitored period of time.

In some aspects the methods described herein could be used to determine if a well had access to (e.g., was receiving contributions from) a known reservoir. For example, in certain embodiments, samples from one or more known reservoirs, each reservoir in some aspects having a detectably different profile as identified by the types of analyses described herein, could each be used as the fluid samples with the profile generated on a series of non-fluid samples using the analysis as described herein to determine whether or not the well from which non-fluid samples were drawn was receiving a significant contribution from such a known reservoir. In some embodiments, the area of the well receiving a contribution from such a reservoir can have a similar profile or same profile as that of the known reservoir.

According to certain embodiments, the invention described herein can be combined with other technologies such as that described in, for example but not limited to, the methods, devices, and technologies described in U.S. patent application Ser. Nos. 15/908,760, 16/019,529, and patent publication number WO2018111945 and in other patent documents in the SMITH Art.

According to embodiments, analytical methods described herein can be used to generate standards or standard profiles for producing and non-producing wells. According to embodiments, the results of any of the analytical methods described herein can be compared with such standards as a step in assessing the oil production properties of an oil well.

Comparative Analysis of Release Resistant Water

In some respects, the invention is characterized as a method of utilizing comparative analysis of a plurality of data sets to identify locations within a well, within a geological unit, within a drilling pad, within a region, or also or alternatively within an otherwise defined and related geographical area of petroleum exploration or production to identify locations expected to be higher producing than others.

In one aspect, the invention provides a method of comparatively analyzing a geologic unit comprising at least two oil wells, which comprises obtaining solid rock samples from the at least two wells, obtaining release resistant water data for each of the wells, and comparing the release resistant water information. In aspects, the release resistant water data can be obtained using techniques described in PCT/US20/13261. In aspects, two or more wells reside within the same geological unit, within a drilling pad, within a region, or also or alternatively within an otherwise defined and related geographical area of petroleum exploration or production. In aspects, two or more wells reside within a defined geographical region wherein the exact characteristics of the region are not well established or known, such that one or more attributes of a geological unit accessed by the wells is unknown and the results of the comparative analysis of samples from the at least two wells provide insights as to the attributes and characteristics of the region, e.g., zones of higher/lower production.

Upon the completion of release resistant water analysis, in one aspect, release resistant water data may be characterized generally as "favorable" (or, e.g., more likely producing than "non-favorable") or "non-favorable" (or, e.g., less likely producing than "favorable"). In aspects, such data can be associated with zones within a single well or the well as a whole. In aspects, data for a first well can be compared to data for an at least second well. In certain aspects, the overlap of favorable release resistant water characteristics in the two or more wells is used to identify one or more oil-rich zones. In other aspects, the relative poor performance of one or more wells in a region characterized by release resistant water analysis, and relative good performance of one or more other wells in the region characterized by release resistant water analysis, is used to identify favorable portions of the region for oil production. In one aspect, the wells are lateral wells, and the results are used to map favorable lateral zones in the geologic unit for petroleum production. In certain aspects, analysis of release resistant water data from specific zones within one well can be compared to that of the same zones within at least a second well, wherein overlap of favorable release resistant water characteristics in the two or more wells is used to identify one or more oil-rich zones. In one aspect, the wells are lateral wells, and the zone comparison analysis is used to map favorable vertical zones in the geologic unit.

In aspects, comparative liquid/solid saturated hydrocarbon ratio analysis utilizing methods described herein can be combined with comparative release resistant water analysis utilizing methods described herein to provide an enhanced data set for consideration in determining areas of expected productivity or also or alternatively zones of relatively higher productivity than others. In aspects, the results of one comparative analysis can be used to confirm or validate another comparative analysis. In aspects, comparative analysis of liquid/solid saturated hydrocarbon ratio analysis and comparative analysis of release resistant water data, alone or together, can be utilized to confirm areas of high or low productivity, can be utilized to predict areas of high or low productivity, or can be utilized at least in part to direct drilling operations to maximize production.

Sufficiency Analysis

In aspects, analytical information derived from the various step(s) of the method(s) can be used to evaluate the oil producing contribution of any one or more additional location(s) of the geologic unit represented by the location from which one or more additional samples are collected. In aspects, such an evaluation can be accomplished by comparing the amount(s) of the measured compound(s) in a first fluid material sample to the amount(s) of the measured corresponding carbon-compositionally similar and structurally similar organic compound(s) in each of any one or more additional samples. In aspects, such an evaluation can be accomplished by comparing one or more ratios of one or more measured compound(s) in a first fluid material sample to the same or similar ratios of the same or carbon-compositionally similar and structurally similar compounds in each of any one or more additional samples. In aspects, an increased presence of corresponding or structurally similar organic compounds, or ratios thereof, in one or more of the additional samples with respect to organic compounds, or ratios thereof, identified in the first sample indicates a higher likelihood of the location from which such one or more second/additional sample(s) was collected contributing to the characteristics of the first fluid material. In aspects, determining whether the comparison is sufficient to identify the characteristics of the first fluid material as being established by material contributed from the location at which the second or further additional sample(s) was collected is a component of method(s) herein.

In aspects, in the event that a comparison of compound(s) or ratio(s) of a second or any additional sample(s) to a first sample(s) is not sufficient to identify the characteristics of a first sample, e.g., a first fluid material sample, as being established by material contributed from the location at which the second (or additional) sample was collected, the method can comprise collecting at least one additional sample comprising solid material from at least one additional location of the geologic unit. In aspects, the evaluation of sufficiency of a second sample (e.g., a single sample collected in addition to a first fluid sample) determines whether or not one or more additional steps of a method will be, can be, or should be performed. In aspects, collecting at least one additional, at least two additional, at least four additional, at least 8 additional, at least 16 additional, at least 32 additional, at least 64 additional, at least 128 additional, at least 256 additional, at least 500 additional, or at least 1000 additional samples are collected based upon the evaluation of sufficiency of a second sample to identify the characteristics of a first sample, e.g., a first fluid material sample, as being established by material contributed from the location at which the second (or additional) sample was collected.

In aspects, analytical information derived from one or more step(s) of the method(s) can be used to evaluate the likelihood of the first fluid sample and one or more additional samples having the source location, or, e.g., as having the same location of origin, by comparing the amount of the measured compound(s) or ratio(s) thereof in a first fluid sample to the amounts of the measured corresponding carbon-compositionally similar and structurally similar organic compound(s) or ratio(s) thereof in the one or more additional samples. In aspects, the greater the presence of corresponding or structurally similar organic compounds or ratios thereof in one or more of the one or more additional samples with respect to organic compounds or ratios thereof identified in the first sample increases the likelihood of the first fluid sample and the one or more of the one or more additional samples having originated from the same source (or, in aspects, as the samples having the same source location. In aspects, determining whether the comparison is sufficient to identify the characteristics of a first fluid sample as being contributed by fluid located at or deriving from a location represented by second (or additional) fluid sample(s) is an element of the method(s) of the invention. In aspects, the result of such a sufficiency determination can lead to the determination of whether or not performance of one or more additional steps of a method can be, should be, or are performed.

In aspects, in the event the comparison is deemed not to be sufficient (e.g., is deemed insufficient) to identify the characteristics of a first fluid sample as being contributed by fluid located at or sourced from the location from which a second fluid sample was collected or sourced from, the method can comprise collecting at least one additional sample comprising fluid material from at least one additional location of the geologic unit. In aspects, the method comprises collecting at least two additional samples, at least four additional samples, at least 8 additional samples, at least 16 additional samples, at least 32 additional samples, at least 64 additional samples, at least 128 additional samples, at least 256 additional samples, at least 500 additional samples, or at least 1000 additional samples when such an insufficiency determination is made.

In aspects, a method disclosed herein can comprise two or more steps of sufficiency analysis, such that the method is iterative. In aspects, if a first insufficiency evaluation as described in this section is made, additional one or more samples can be evaluated. If upon evaluation of such one or more samples yields further insufficiency determinations, still additional one or more samples can be evaluated. In aspects, such an iterative process can be continued until such a sufficiency evaluation is determined to be sufficient to identify the characteristic(s) of a first fluid sample as being contributed by fluid located at or sourced from the location from which a second or additional fluid sample was collected or sourced from. In aspects, such an iterative process can also be applied to methods described herein wherein the first sample is a fluid sample, second and any one or more additional samples are non-fluid samples, and the aim of the method is to determine (a) the likely contribution of any location represented by a second or additional non-fluid sample to the characteristic(s) of a fluid sample, (b) the relative contribution of various sampled locations to the characteristics of a fluid sample, or both (a) and (b).

Oil Typing Applications

In aspects, analytical information derived from any one or more step(s) of the method(s) can be used to determine the source location, sometimes referred to here or in the art as "provenance", of one or more fluid samples. In aspects, analytical information derived from one or more step(s) of the method(s) can be used to identify whether two or more samples, e.g., fluid samples, are likely to share the same source location. In aspects, analytical information derived from one or more step(s) of the method(s) can be used to identify whether two or more fluids collected from the same geologic site, e.g., well, e.g., petroleum well, are likely to have been derived from the same pulse; that is, the likelihood that such two or more fluids were expelled from the same source rock at a similar point in time in terms of the maturation of the source rock.

In aspects, the invention provides a method of identifying relative contributions of spatially distributed locations within a geologic site to a produced material (e.g., to a produced oil). In aspects, a location providing a high likelihood of contribution to a produced material, e.g., produced oil, is referred to as a "highly contributing location of origin" for such a produced material, or a highly contributing source location. In aspects, the invention provides a method of assigning one or more locations of a studied area/site as having a high likelihood of contribution to a produced material. In certain aspects, such a location providing a high likelihood of contribution to a produced material is referred to as a "provenance" of the produced material.

In aspects, methods herein facilitate the evaluation of or provide for the determination of whether or not two or more oils produced from the same well(s) have the same source location, e.g., pulse—e.g., that the two or more oils produced from the same well(s) were expelled from the same source rock at a similar point in time in terms of the maturation of the source rock. In aspects, one or more ratio(s) compounds used in methods described herein do not respond to the oil in the source rock that produced them, but, rather, to the stage in thermal maturation that the source rock was at the time when the oil departed the source rock. In aspects, the use of ratio(s) in comparative steps of method(s) described herein is capable of distinguishing that two or more fluids share a source location. In aspects, the use of ratio(s) in comparative steps of method(s) described herein is capable of distinguishing that two or more fluids share a source location when at least one other evaluation, e.g., comparison, of the same two or more fluids indicate that the fluids have different source locations. In aspects, the use of ratio(s) in comparative steps of method(s) described herein is capable of distinguishing that two or more fluids share a source location when a complete comparison of directly measured compound(s) indicates that the fluids have different source locations. In aspects, it is the density distribution, e.g., phase relationships of compounds that provides comparative insight. In aspects, for example, a sample derived from a first region with greater quantities of gas than a second region will have a greater quantity of certain compounds, e.g., pentanes (as, e.g., pentanes are typically significantly more gas soluble than other liquid hydrocarbons). A comparison between such a sample and a second sample from a different region, because of its higher amount of pentanes, may instruct one to conclude that the two samples do not share the same source location. However, an analysis of ratios of specific compounds can, in certain aspects, distinguish that the two samples in fact do share the same source location. This is further described in Examples provided herein.

In aspects, comparative liquid/liquid saturated hydrocarbon ratio analysis utilizing methods described herein can be utilized to provide an enhanced data set for consideration in determining provenance of samples. In aspects, the results of one comparative analysis can be used to confirm or validate another comparative analysis. In aspects, comparative analysis of liquid/liquid saturated hydrocarbon ratio analysis can be utilized to confirm areas having the same provenance and, further, areas of high or low productivity, can be utilized to predict areas of high or low productivity, or can be utilized at least in part to direct drilling operations to maximize production.

EXAMPLES & DETAILED DESCRIPTION OF THE FIGURES

The following exemplary applications of particular methods of the invention are provided to better illustrate and illuminate the invention, but such examples should not be interpreted as limiting the scope of the invention in any manner. Some of the examples described herein in present tense are prophetic examples that have not yet been put to practice.

Example 1

An analysis of a conventional, unconsolidated sand reservoir in a major oil province was conducted using samples obtained from a lateral well accessing the reservoir. This well served both an exploration and development role as it was the first well targeting this reservoir but was also designed to be produced. Analysis of the samples comprised determining the relative productivity of well intervals to the whole oil product of the well.

A sample of a whole oil after the well was brought under production along with drill cuttings samples collected and hermetically sealed while the well was being drilled were used for the analysis. Cuttings were collected at intervals ranging between approximately 30 to 120 ft. Approximately 85 drill cuttings samples representing depths of the well spanning approximately 5400 ft to approximately 11460 ft were provided for analysis. All samples were hermetically sealed within approximately 3 minutes of collection. Cuttings samples were stored in hermetically sealed sample containers under ambient (room temperature) conditions and submitted for analysis within two weeks after collection. The whole oil sample was stored under ambient conditions in a sealed Nalgene bottle for approximately 6 weeks, though the exact length of time in storage before being submitted for analysis was not recorded. Along with the samples, information about the completion scheme of the well was also provided (e.g., a description of which portions of the borehole contained casing with screens to allow an influx of oil from the reservoir). Screens were placed from 5680 ft to 9120 ft and from 9390 ft to 9700 ft.

Because the reservoir was a sand reservoir, it was determined that the use of ratios of C6, C7, and C8 alkanes and cycloalkanes would be appropriate for analysis. Use of ratios were chosen as more appropriate than use of direct measurements of the analytes as the characteristics of the sample rock did not lend itself to holding a representative composition of oil in terms of absolute abundance, however the relative abundance C6, C7, and C8 alkanes to cycloalkanes was determined to be valid as alkanes and cycloalkanes have very similar molecular properties and were unlikely to undergo distinct interactions with the rock relative to one another or experience unique fractionation process(es). The likelihood of significant skewing of ratios of such species within such a reservoir was deemed to be low.

All samples provided (whole oil sample and all cuttings samples) were submitted to an analysis method comprising a gentle vacuum and cryogenic trap separation technique followed by quantification via mass spectrophotometry, a method described in the SMITH Art. C6 alkane, C6 cycloalkane, C7 alkane, C7 cycloalkane, C8 alkane, and C8 cycloalkane values for all samples were obtained. The method utilized for quantification did not distinguish between normal and branched forms of the analytes, the results being representative of a total of all forms of each analyte. Results of the analysis were compiled in Microsoft EXCEL.

The following three ratios were calculated for each sample using the compiled results: C6 alkane/(C6 alkane+C6 cycloalkane); C7 alkane/(C7 alkane+C7 cycloalkane); C8 alkane/(C8 alkane+C8 cycloalkane).

Because of the variety of sampling intervals collected due to operational concerns, the well was modeled, that is, the well was divided, as a series of 60 ft intervals with the composition at the center of each interval being taken as representative of the interval (in this Example there are two intervals which were shorter than 60 ft given that 60 ft did not neatly divide the screened sections into whole numbers). Interpolation of neighboring samples was used to generate the values at the center of the interval. Each interval value was then assigned an initial scaling factor representative of that interval's spatial contribution to the total well length being considered. In this case, the span of well that was considered was approximately 3750 feet, therefore each 60-foot interval was assigned an initial scaling factor of approximately 0.0156, each interval being representative of close to 1/64th of the total well length which was completed with screens.

All ratios were then multiplied by the scaling factor and the results prepared for analysis using a numerical method engine (description to follow). Each modeled end product value was directly compared to the end product value to establish residuals. The residuals were normalized against the starting end product value to prevent overweighting. The normalized residuals were squared and subsequently summed (providing a residual sum of squares). The scaling factor was set as an adjustable variable at each interval. The numerical method was provided three constraints to aid in analysis. The first constraint was the identification of the known well depths which had been completed with screens as noted above. The second constraint was that the sum of contributions from the scaling factor can be approximately 1. The final constraint was that the residual sum of squares from comparing the ratio values obtained from the produced oil sample (liquid sample) versus the total ratios (sum of scaling factor*ratio at a given interval) of the non-liquid (solid) samples can equal 0. It was understood that this is a state (residual sum of squares actually equaling zero) may likely rarely be actually achieved. It can be clear that this is established as a constraint to provide a target for the analytical method. The aim of the analysis was and is for the numerical method to provide values resulting in the residual sum of squares which approach zero to the greatest extent possible, to a point at which a minimum residual sum of squares value is achieved. That is, the aim of the analysis is for the numerical method to provide a set of values whereby the numerical method cannot iterate a different set of values achieving a state closer to this requirement. Such a set of values represents the contribution of each position of the well to the final produced fluid. In a scenario where a related fluid was utilized in the analysis (such a scenario described as an aspect herein), such a set of values can be representative of the expected contribution of each position of the well to the expected final produced fluid from that well.

The numerical method engine utilized in this analysis is the engine available in the programming aspect of Microsoft EXCEL utilizing Visual Basic for Applications (VBA); the functionality is known as "Solver". This engine was executed and allowed to iterate to identify the best set of scaling factors which, when applied to each ratio, best approximated the provided ratio profile of the whole oil (liquid) sample. More precisely, the numerical method engine iterated to identify the combination of variables which resulted in a sum of the squared residuals value, each squared residual being generated by the comparison of each individual ratio modeled versus that measured in the whole oil, and the sum being the contribution from each ratio comparison taken in total, which was closest to zero.

Residuals were also normalized by the ratio value measured from the whole oil (liquid sample) to remove bias as a function of which set of ratios have the larger absolute value.

Data as described and the results of the EXAMPLE 1 analysis are herein provided by use of incorporated figures.

Figure 1:
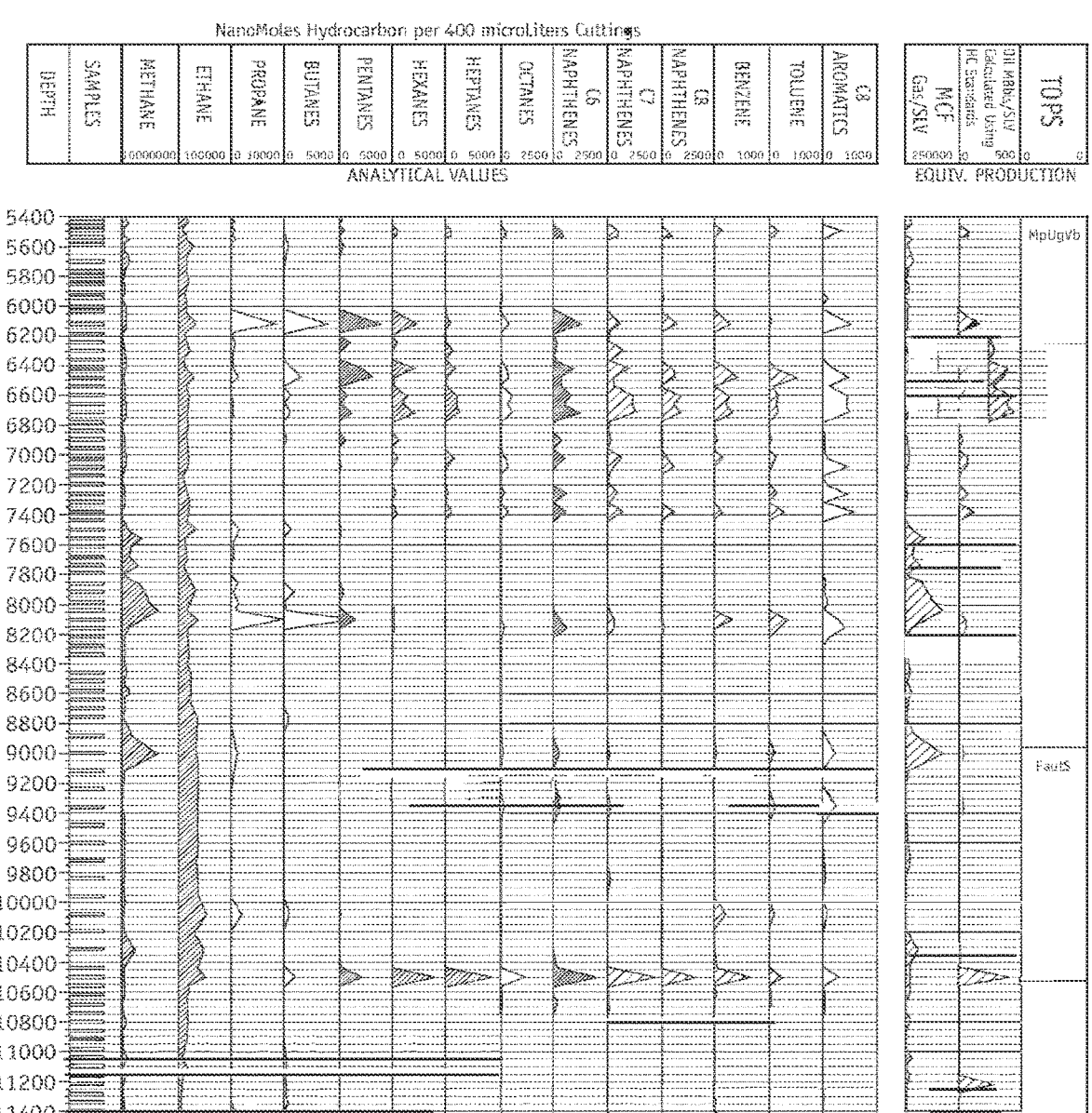
FIG. 1 is a hydrocarbon log from the analysis of sealed at well cuttings showing measured values of various hydrocarbons over the length of a drilled well. Data in FIG. 1 and the other Figures are discussed below.

FIG. 1 is the hydrocarbon log from the analysis of the sealed at the well drill cuttings provided for the analysis provided in this Example. The log provides the detected absolute concentration at each well position of a variety of different chemistries from the C1-C8 hydrocarbons. Hydrocarbons up to C10 were measured, however this data (e.g., C9 & C10 data) is not shown.

Figure 2:
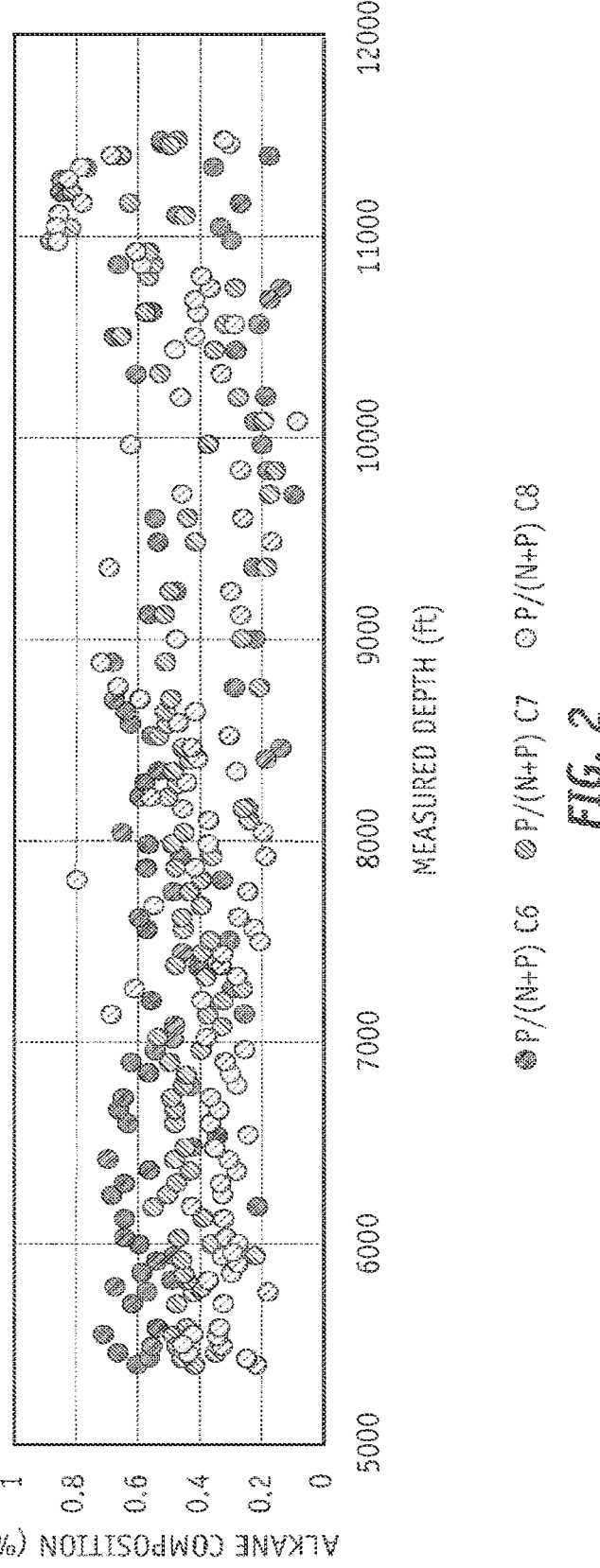
FIG. 2 is a graphical representation showing specific calculated ratios using the hydrocarbon log data from FIG. 1.

FIG. 2 presents the calculated alkane/(alkane+cycloalkane) ratio for each cuttings sample collected across the length of the borehole, presented in graphical form. These ratios, as described previously, were calculated from the directly measured values of alkanes and cycloalkanes shown in FIG. 1. FIG. 2 shows the ratio values for the C6, C7, and C8 species.

Figure 3:
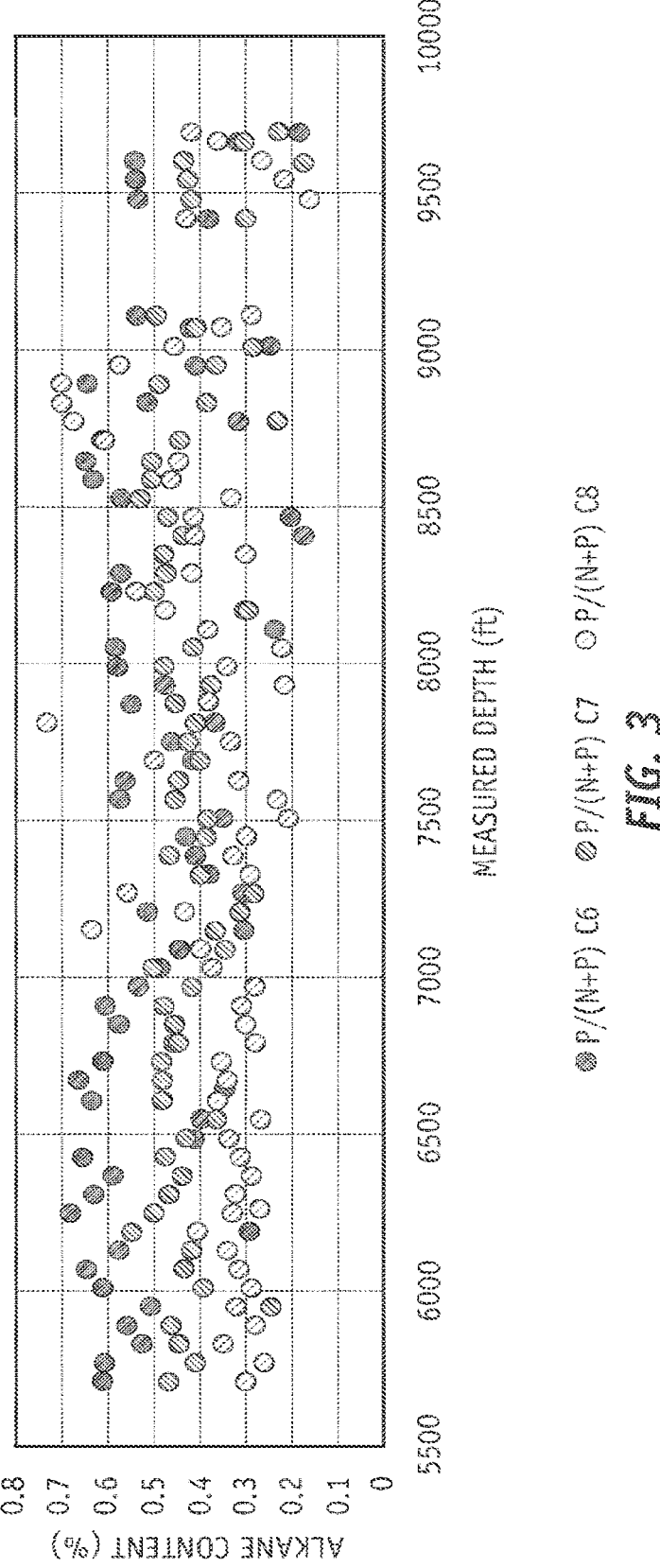
FIG. 3 is an interpolated version of the same graphical representation as FIG. 2, however only showing intervals of the well where the borehole was completed.

FIG. 3 is an interpolated version of the same graphical representation as FIG. 2, however only showing intervals of the well where the borehole was completed with screens. FIG. 3 shows the ratios of FIG. 2 at 60-ft intervals across the portion of the borehole completed with screens.

Figure 4:
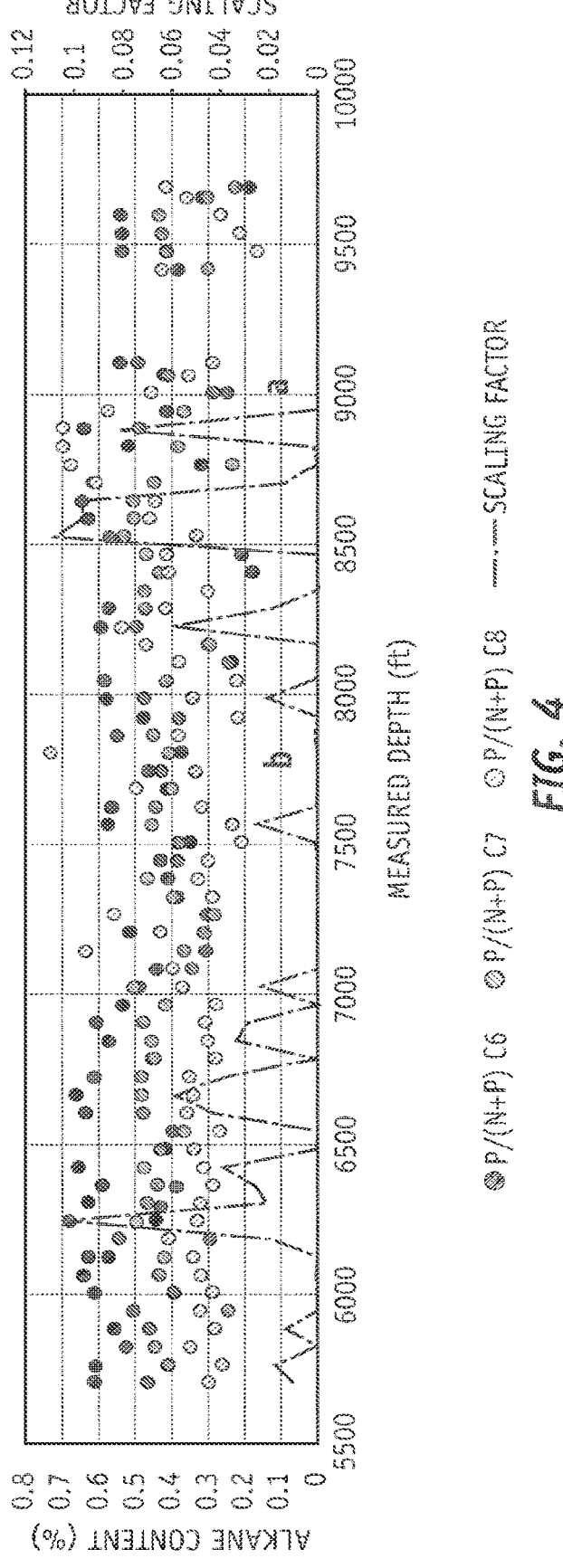
FIG. 4 is an expanded version of FIG. 3A with a scaling factor as determined by a numerical method engine overlaid.

FIG. 4 provides the identified scaling factor (identified by the line on the graph), optimized at 63 positions along the open portion(s) (e.g., completed with screens) of the borehole, overlaid on FIG. 3. The identified scaling factor at each position represents the relative contribution each interpolated interval must make to result in a sum of the squared residuals value closest to zero while also imposing the model constraint that the sum of contributions from the scaling factor can be approximately 1. Peaks in the scaling factor represent positions within the well having a higher contribution; valleys indicate positions within the well having a lower contribution.

FIG. 4 illustrates the ability of the method described to detect geographical factors influencing relative productivity, the scaling factor responding to independently known factors that the model is unaware of. There is minimal to no significant contribution past point the point labeled as "a" in FIG. 4, as demonstrated by the scaling factor line at 0 after that point. It is known that the borehole crosses a fault block at the depth indicated by "a". Multiple analyses not included here suggest this fault block is likely to be only minimally productive; oil here shows evidence of being highly biodegraded which may result in an unproductive tar phase which could also cause problems with the production of the resource. Further, no significant contributions are observed at the point indicated by "b" in FIG. 4, again as demonstrated by the scaling factor line at zero at that point. This position is known to correlate with a measured decrease in mechanical strength and an increase in gamma ray response, suggesting either a silt stone or possibly a mud stone, both rock types that would be minimally productive compared to the unconsolidated sand formation that makes up the majority of the reservoir.

The analysis provided in this example yielded actionable data for field management. The model revealed that all contribution in this well is coming from the first fault block in localized positions and that the second fault block is not significantly contributing significantly. Given the identification of a non-contributing fault block, action could be taken to attempt to generate contribution or alternatively to abandon that fault block.

Example 2

An analysis of a conventional, unconsolidated sand reservoir in a major oil province is conducted using samples obtained from a lateral well accessing the reservoir. This well serves both an exploration and development role as it is the first well targeting this reservoir but is designed to be produced.

Analysis of the samples comprises determining the relative productivity of well intervals to the whole oil product of the well.

A sample of a whole oil after the well is brought under production along with drill cuttings samples collected and hermetically sealed while the well was being drilled are used for the analysis. Cuttings are collected at intervals ranging between approximately 30 to 120 ft. Approximately 85 drill cuttings samples representing depths of the well spanning approximately 5400 ft to approximately 11460 ft are provided for analysis. All samples are hermetically sealed within approximately 3 minutes of collection. Cuttings samples are stored in hermetically sealed sample containers under ambient (room temperature) conditions and submitted for analysis within two weeks after collection. The whole oil sample is stored under ambient conditions in a sealed container for approximately 6 weeks. Along with the samples, information about the completion scheme of the well is provided (e.g., a description of which portions of the borehole contained casing with screens to allow an influx of oil from the reservoir). According to the completion scheme, screens are placed from 5680 ft to 9120 ft and from 9390 ft to 9700 ft.

Because the reservoir is a sand reservoir, it is determined that the use of ratios of C6, C7, and C8 alkanes and cycloalkanes is appropriate for analysis. Use of ratios are chosen as more appropriate than use of direct measurements of the analytes as the characteristics of the sample rock do not lend itself to holding a representative composition of oil in terms of absolute abundance, however the relative abundance C6, C7, and C8 alkanes to cycloalkanes is determined to be valid as alkanes and cycloalkanes have very similar molecular properties and would be unlikely to undergo distinct interactions with the rock relative to one another or experience unique fractionation process(es), hence the likelihood of significant skewing of the ratios of such species within such a reservoir is deemed to be low.

All samples provided (whole oil sample and all cuttings samples) are submitted to an analysis method comprising a gentle vacuum and cryogenic trap separation technique followed by quantification via mass spectrophotometry, a method described in the SMITH Art. C6 alkane, C6 cycloalkane, C7 alkane, C7 cycloalkane, C8 alkane, and C8 cycloalkane values for all samples are obtained. The method utilized for quantification does not distinguish between normal and branched forms of the analytes, the results being representative of a total of all forms of each analyte. Results of the analysis are compiled in Microsoft EXCEL.

The following three ratios are calculated for each sample using the compiled results: C6 alkane/(C6 alkane+C6 cycloalkane); C7 alkane/(C7 alkane+C7 cycloalkane); C9 alkane/(C8 alkane+C8 cycloalkane).

Because of the variety of sampling intervals collected due to operational concerns, the well is modeled, that is, the well is divided, as a series of 60 ft intervals with the composition at the center of each interval being taken as representative of the interval (in this Example there are two intervals which are shorter than 60 ft given that 60 ft do not neatly divide the screened sections into whole numbers). Interpolation of neighboring samples is used to generate the values at the center of the interval. Each interval value is then assigned a scaling factor representative of that interval's spatial contribution to the total well length being considered. In this case, the span of well being considered is approximately 3750 feet, therefore each 60-foot interval is assigned a scaling factor of approximately 0.0156, each interval being representative of close to $1/64$th of the total well length which is completed with screens.

All ratios are then multiplied by the scaling factor and the results are analyzed using a numerical method engine. The numerical method engine utilized in this analysis is the engine available in the programming aspect of Microsoft EXCEL utilizing Visual Basic for Applications (VBA); the functionality is known as "Solver". The scaling factor is set as an adjustable variable at each interval. The numerical method is provided three constraints to aid in analysis. The first constraint is the identification of the known well depths which are completed with screens as noted above. The second constraint is that the sum of contributions from the scaling factor can be approximately 1. The final constraint is that the residual sum of squares from comparing the ratio values obtained from the produced oil sample versus the total ratios (sum of scaling factor*ratio at a given interval) can equal or approximate 0.

The numerical method engine is then executed and allowed to iterate to identify the best set of scaling factors which, when applied to each ratio, best approximates the provided ratio profile of the whole oil sample. More precisely, the numerical method engine iterates to identify the combination of variables which result in a sum of the squared residuals value, each squared residual being generated by the comparison of each individual ratio modeled versus that measured in the whole oil, and the sum being the contribution from each ratio comparison taken in total, which is closest to zero. Residuals are also normalized by the ratio value measured from the whole oil to remove bias as a function of which set of ratios have the larger absolute value.

The set of scaling factors at each position resulting in a sum of squared residuals value closest to zero, under the model constraint that the sum of the contributions from the scaling factor can be approximately 1 indicates that the first $1/3$ of the well is predicted to be productive, the second $1/3$ of the well is predicted to be non-productive (alternatively stated, the second $1/3$ of the well is not expected to contribute significantly to a produced oil from this well), and the final $1/3$ of the well is also predicted to be non-productive; that is, only the first $1/3$ of the well is predicted to contribute to a produced oil from this well.

The analysis provides actionable data for field management. The model reveals that all contribution in this well is predicted to come from the first one-third of the well and the lower $2/3$ of the well is predicted to not contribute at all. A decision is made to not complete the lower $2/3$ of the well and to only complete the first $1/3$ of the well.

Example 3

An analysis of a conventional, unconsolidated sand reservoir in a major oil province is conducted using samples obtained from lateral well accessing the reservoir. This well serves both an exploration and development role as it is the first well targeting this reservoir but is designed to be produced.

Analysis of the samples comprises determining the relative productivity of well intervals to the whole oil product of the well.

A sample of a whole oil after the well is brought under production along with drill cuttings samples collected and hermetically sealed while the well was being drilled are used for the analysis. Cuttings are collected at intervals ranging between approximately 30 to 120 ft. Approximately 85 drill cuttings samples representing depths of the well spanning approximately 5400 ft to approximately 11460 ft are provided for analysis. All samples are hermetically sealed within approximately 3 minutes of collection. Cuttings samples are stored in hermetically sealed sample containers under ambient (room temperature) conditions and submitted for analysis within two weeks after collection. The whole oil sample is stored under ambient conditions in a sealed container for approximately 6 weeks. Along with the samples, information about the completion scheme of the well is provided (e.g., a description of which portions of the borehole contained casing with screens to allow an influx of oil from the reservoir). According to the completion scheme, screens are placed from 5680 ft to 9120 ft and from 9390 ft to 9700 ft.

Because the reservoir is a sand reservoir, it is determined that the use of ratios of C6, C7, and C8 alkanes and cycloalkanes is appropriate for analysis. Use of ratios are chosen as more appropriate than use of direct measurements of the analytes as the characteristics of the sample rock do not lend itself to holding a representative composition of oil in terms of absolute abundance, however the relative abundance C6, C7, and C8 alkanes to cycloalkanes is determined to be valid as alkanes and cycloalkanes have very similar molecular properties and would be unlikely to undergo distinct interactions with the rock relative to one another or experience unique fractionation process(es), hence the likelihood of significant skewing of the ratios of such species within such a reservoir is deemed to be low.

All samples provided (whole oil sample and all cuttings samples) are submitted to an analysis method comprising a gentle vacuum and cryogenic trap separation technique followed by quantification via mass spectrophotometry, a method described in patent publication number WO2018111945. C6 alkane, C6 cycloalkane, C7 alkane, C7 cycloalkane, C8 alkane, and C8 cycloalkane values for all samples are obtained. The method utilized for quantification does not distinguish between normal and branched forms of the analytes, the results being representative of a total of all forms of each analyte. Results of the analysis are compiled in EXCEL.

The following three ratios are calculated for each sample using the compiled results: C6 alkane/(C6 alkane+C6 cycloalkane); C7 alkane/(C7 alkane+C7 cycloalkane); C9 alkane/(C8 alkane+C8 cycloalkane).

Because of the variety of sampling intervals collected due to operational concerns, the well is modeled, that is, the well is divided, as a series of 60 ft intervals with the composition at the center of each interval being taken as representative of the interval (in this Example there are two intervals which are shorter than 60 ft given that 60 ft do not neatly divide the screened sections into whole numbers). Interpolation of neighboring samples is used to generate the values at the center of the interval. Each interval value is then assigned a scaling factor representative of that interval's spatial contribution to the total well length being considered. In this case, the span of well being considered is approximately 3750 feet, therefore each 60-foot interval is assigned a scaling factor of approximately 0.0156, each interval being representative of close to 1/64th of the total well length which is completed with screens.

All ratios are then multiplied by the scaling factor and the results are analyzed using a numerical method engine. The numerical method engine utilized in this analysis is the engine available in the programming aspect of Microsoft EXCEL utilizing Visual Basic for Applications (VBA); the functionality is known as "Solver". The scaling factor is set as an adjustable variable at each interval. The numerical method is provided three constraints to aid in analysis. The first constraint is the identification of the known well depths which are completed with screens as noted above. The second constraint is that the sum of contributions from the scaling factor can be approximately 1. The final constraint is that the residual sum of squares from comparing the ratio values obtained from the produced oil sample versus the total ratios (sum of scaling factor*ratio at a given interval) can equal 0.

The numerical method engine is then executed and allowed to iterate to identify the best set of scaling factors which, when applied to each ratio, best approximates the provided ratio profile of the whole oil sample. More precisely, the numerical method engine iterates to identify the combination of variables which result in a sum of the squared residuals value, each squared residual being generated by the comparison of each individual ratio modeled versus that measured in the whole oil, and the sum being the contribution from each ratio comparison taken in total, which is closest to zero. Residuals are also normalized by the ratio value measured from the whole oil to remove bias as a function of which set of ratios have the larger absolute value.

The set of scaling factors at each position resulting in a sum of squared residuals value closest to zero, under the model constraint that the sum of the contributions from the scaling factor can be approximately 1 indicates that the first 1/3 of the well is predicted to be productive, the second 1/3 of the well is predicted to be non-productive (alternatively stated, the second 1/3 of the well is not expected to contribute significantly to a produced oil from this well), and the final 1/3 of the well is predicted to be productive; that is, only the first 1/3 and the last 1/3 of the well is predicted to contribute to a produced oil from this well.

The analysis provides actionable data for field management. The model reveals that all contribution in this well is predicted to come from only 2/3 of the well with the middle 1/3 expected to be non-productive. A decision is made to case middle 1/3 of the well and to not subject that section of the well to fracking, while pursuing the productivity capable of the upper and lower thirds of the well.

Example 4

This Example demonstrates how the principles of comparative analytical methods can be applied to release resistant water measurements obtained from solid samples (petroleum drill cuttings).

Drill cuttings from two lateral wells located in the same geologic unit and in relatively close proximity to each other were collected and subjected to the release resistant water methods described in the SMITH Art, particularly those described in PCT/US20/13261, published as WO 2020/146859. The results of these analyses for the two wells are presented in FIGS. 5 and 6, respectively. The Y axis in each of these Figures reflects a scale of the relative amount of release resistant water released from the tested cuttings and the X-axis reflects a scale of distance that reflects the area from which cuttings were collected for analysis.

Figure 5:
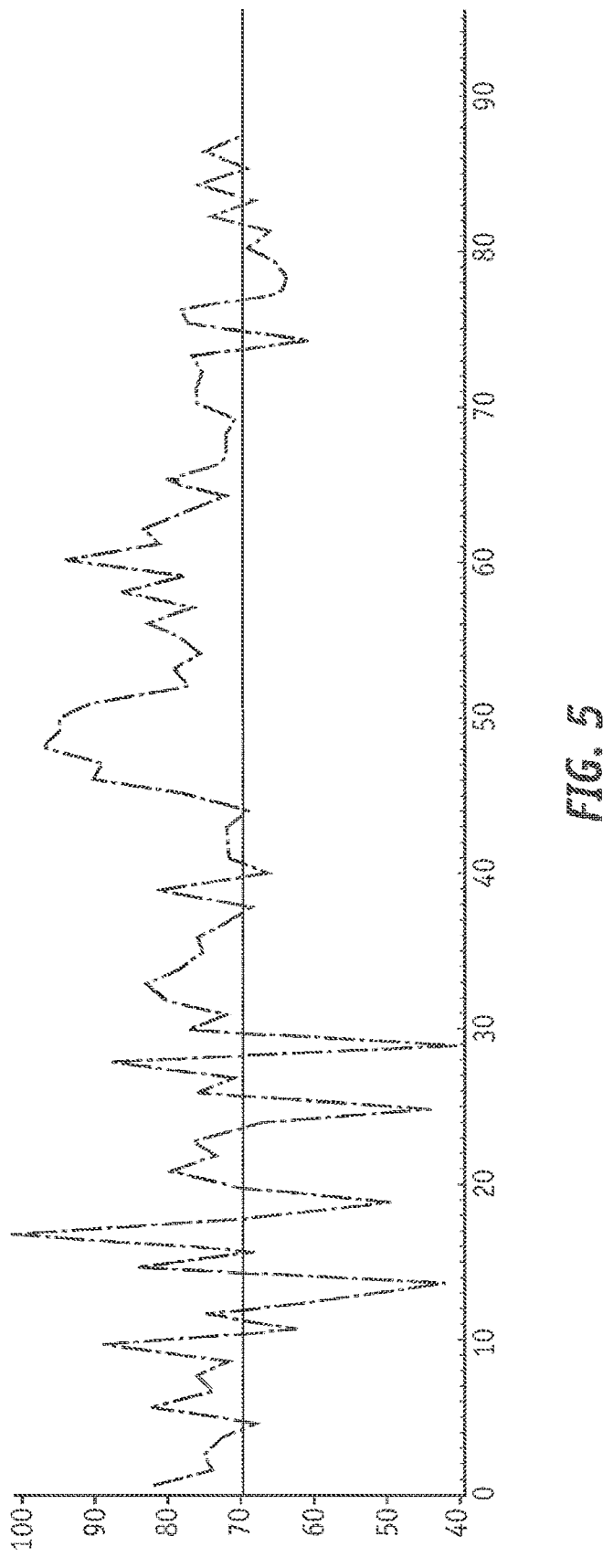
FIG. 5 is a graphical representation of release-resistant water data obtained from cuttings in a first of two lateral wells (the Y-axis representing a relative scale of release-resistant water measurements and the X-axis representing a scale of even distances across the well).
Figure 6:
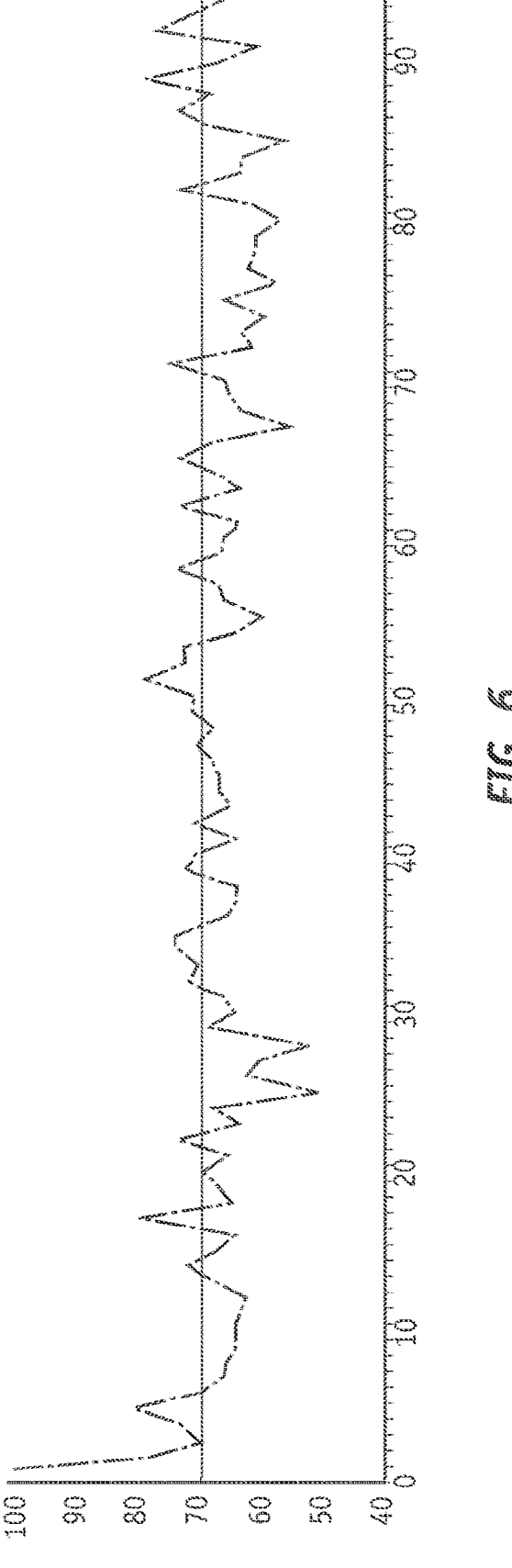
FIG. 6 is a graphical representation of release-resistant water obtained from cuttings in a second of the two lateral wells, at a different depth from but same formation as, the well analyzed in FIG. 5.

FIG. 5 reflects that the 1st well had good oil production characteristics, as determined by release resistant water analysis. FIG. 6 reflects that the 2nd well had poorer oil production properties. Similar to other comparative methods used herein, such a comparative analysis obtained by release resistant water analysis of cuttings can be used to assess lateral zones within a well that are likely to be more productive. It also can be the case that other data points, such as vertical zones of high productivity contained in such lateral wells, also could be identified by such methods. Such methods can be combined with the other methods described herein to generate even more comprehensive comparative analytical methods for pay zone mapping.

Example 5

This Example reflects how, in addition to the principles using the ratios of the various hydrocarbon compounds present in rock samples compared to a produced fluids sample (e.g., a produced hydrocarbon liquids sample) to understand where contributions along the length of the borehole were made, aspects of the invention allow for these same or similar ratios to be used to assign provenance, e.g., source locations, of produced hydrocarbon liquids samples. That is, for example, this Example reflects how aspects of the invention can further be used to identify whether or not two oils produced from the same wells had the same source; e.g., were produced from the same pulse, or, e.g., expelled from the same source rock at a similar point in time in terms of the maturation of the source rock.

FIG. 7 and FIG. 8 reflect data collected from a first oil sample, represented in the graphs of FIG. 7 and FIG. 8 as dashed-bars, and a second oil sample, represented on the graphs of FIG. 7 and FIG. 8 as solid bars.

Each of the first and second oil samples was analyzed by placing a known small volume of oil (1-2 micro litters) into a RVS consumable kit which was analyzed by the RVS instrumentation. This process was repeated three times for each oil sample.

FIG. 7 illustrates the mole fractions of the liquid hydrocarbons measured in the analysis. A comparison of the mold fractions of liquid hydrocarbons measured in oil sample 1 to those in oil sample 2 provides the impression that the two oil samples are quite different, as significant differences are identifiable in the comparison of, e.g., pentanes, hexanes, toluene, 8 naphthenes, and, e.g., octanes. From such an analysis, one might conclude that the two oils had different source locations, or, e.g., a different provenance.

FIG. 8 illustrates data from the analysis of the same two oil samples as in FIG. 7, however the analysis comprised the use of ratios. Here, analysis comprised the comparison of paraffin to naphthene ratios (paraffins versus the sum of paraffins and naphthenes). Data for the following specific ratios are presented C6 P/P+N, C7 P/P+N, C8 P/P+N, C9 P/P+N, C10 P/P+N, P/P+N, P/P+N without ("wo") C5. Here, the use of ratios of paraffins versus the sum of paraffins and naphthenes indicated, especially if the C5 pentanes are removed (far right bars), that the two oils are, in fact, quite similar and are likely related and derive from the same source location (e.g., share the same provenance).

The differences observed in FIG. 7 come from the first (dashed-bar) oil sample having a higher gas content than the second (solid bar) oil sample. This resulted in the increased prevalence of lighter liquid hydrocarbon species in the first oil sample compared to the second.

One of ordinary skill in the art would recognize thermal maturation to involve source rocks, which are organic rich rocks that eventually having their organic components broken down to produce liquid and gas hydrocarbons under a combination of high pressure and temperature conditions from the source rocks being buried. As time passes, temperature increases, and pressure increases, the type of hydrocarbon liquids and gases produced change to increasingly lighter compounds. This continues until there is nothing more complex produced than methane, such that nothing more complex than methane remains as a resource being held within or expelled from the source rock.

This Example exemplifies and reflects that ratios used for oil typing are capable of responding to both the nature of the source rock, for example having more terrestrial versus marine organic content inputs, as well as the thermal maturity of the source rock at the time the hydrocarbon liquids were expelled. In this Example, the ratios were not responding to the source rock that produced them, but, rather, the stage in thermal maturation that the source rock was at when the oil left the source rock. The application of the ratios in this Example provided insight which would otherwise have been missed; a comparison of directly measured compounds in the samples, as shown in FIG. 7, would suggest that the two oil samples came from different sources. However, in fact, what is being observed are effects due to the density distribution/phase relationships. One of these samples came from a region with greater quantities of gas and thus had greater quantities of pentanes present. Pentanes are known to typically be significantly more gas soluble than other liquid hydrocarbons. The ratio analysis in this Example, shown in FIG. 8, indicates that the two oils likely share the same provenance/source location. This finding was consistent with other analyses on these oils provided by separately conducted compositional analysis studies which showed the oils were genetically related (such data not included here).

Exemplary Aspects of the Invention

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may make reference to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2).

Lists of aspects describing specific exemplary embodiments of the invention are sometimes employed for aiding the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in combination with one another as unique embodiment(s) of the invention, according to the presentation provided of such aspects unless such an aspect within such a referenced range is either contradictory or non-sensical. If contradicted, reference to the contradictory aspect should be excluded.

In aspects, the invention provides a method for analyzing the oil production properties of an oil well comprising:

a. measuring an amount of at least one first organic compound component in a first sample fluid substantially comprising a liquid, wherein the sample comprises either a formation liquid or a liquid that has been in contact with a formation liquid under conditions sufficient to transfer a detectable amount of the at least one compound, if present, to the liquid sample;

b. measuring an amount of at least one organic compound having also been measured in the first sample; at least one organic compound carbon compositionally similar (CCSC) to a compound having been measured in the first sample; at least one organic compound structurally similar (SSC) to a compound having been measured in the first sample; or any combination thereof, in at least one second sample comprising a rock obtained from the well or a from a corresponding portion of the geologic unit, wherein the at least one compound of the second sample is extracted from the second sample by subjecting the second sample to gentle vacuum pressure (e.g., a negative pressure of about $1 \times 10^{-2}$ millibars or less applied at about room temperature for about 3-30 minutes); and c. comparing the amount of the at least one organic compound in the first sample to the amount of the at least one same or similar (e.g., CCSC, SSC, or both) organic compound in the second sample to assess the oil production properties of the oil well (aspect 1).

In aspects, the invention provides the method of aspect 1, wherein two or more organic compounds are measured in both the first and second samples (aspect 2).

In aspects, the invention provides the method of any one or both of aspects 1 or 2, wherein the amount of the organic compounds is measured in at least two second rock samples (aspect 3).

In aspects, the invention provides the method of any one or more of aspects 1-3, wherein the first sample and the second sample(s) are collected from the same well (aspect 4).

In aspects, the invention provides the method of any one or more of aspects 1-3, wherein the first sample and the second sample(s) are collected from different wells (aspect 5).

In aspects, the invention provides the method of any one or more of aspects 1-5, wherein the organic compound(s) is/are (a) hydrocarbon(s) (aspect 6).

In aspects, the invention provides the method of aspect 6, wherein the organic compound(s) is/are (a) C4-C11 hydrocarbon(s) (aspect 7).

In aspects, the invention provides the method of aspect 7, wherein the organic compound(s) is/are (a) C5-C10 hydrocarbon(s) (aspect 8).

In aspects, the invention provides the method of aspect 8, wherein the organic compound(s) is/are (a) C6-C9 hydrocarbon(s) (aspect 9).

In aspects, the invention provides the method of aspect 9, wherein the organic compound(s) is/are (a) C6-C8 hydrocarbon(s) (aspect 10).

In aspects, the invention provides the method of any one or more of aspects 6-10, wherein the hydrocarbon(s) comprise, primarily comprise, or consist of alkane or cycloalkyl compounds (aspect 11).

In aspects, the invention provides the method of any one or more of aspects 1-11, wherein the well is divided into representative zones prior to scaling (aspect 12).

In aspects, the invention provides the method of any one or more of aspects 1-11, wherein in comparing the amount of the at least one organic compound in the first sample to the amount of the at least one same or similar (e.g., CCSC, SSC, or both) organic compound in the second sample, each sample is scaled according to its spatial contribution to the overall length of the well from which samples were collected (aspect 13).

In aspects, the invention provides the method of any one or more of aspects 1-13, wherein the well is divided into intervals, each interval being assigned an average organic compound value for each organic compound measured based on the second (rock) samples collected and measured within that interval (aspect 14).

In aspects, the invention provides the method of any one or more of aspects 1-14, wherein one or more ratio(s) are calculated comprising two or more measured organic compounds and the one or more ratios are used in the comparison of the first sample with one or more second samples (aspect 15).

In aspects, the invention provides the method of any one or more of aspects 1-15, wherein in comparing the one or more ratio(s) of compounds measured from the first sample to a ratio of the compounds or substantially similar compounds obtained from the one or more second sample(s), the ratio of each sample or each interval is optionally scaled according to its spatial contribution to the overall length of the well from which samples were collected (aspect 16).

In aspects, the invention provides the method of any one or both of aspects 15-16, wherein the one or more ratio(s) comprises alkane/(alkane+cycloalkane) (aspect 17).

In aspects, the invention provides the method of any one or more of aspects 3-17, wherein in the assessment of the oil production properties of the oil well comprises a determination of the relative contribution of each single location, as represented by a single sample, or each interval, as represented by an averaged set of samples, of the well (aspect 18).

In aspects, the invention provides the method of aspect 18, wherein in determining the relative contributions of each single location or each interval only those locations of the well open to an influx of fluid, if present are considered (aspect 19).

In aspects, the invention provides the method of any one or more of aspects 1-19, wherein the fluid is a produced oil (aspect 20).

In aspects, the invention provides the method of any one or more of aspects 1-19, wherein the fluid is a flowback material (aspect 21).

In aspects, the invention provides the method of any one or more of aspects 1-19, wherein the fluid is water (aspect 22).

The method of any one or more of aspects 12-19, wherein the fluid comprises fluid obtained from fluid inclusions (aspect 23).

In aspects, the invention provides the method of any one or more of aspects 1-19, wherein the fluid is a condensate (aspect 24).

In aspects, the invention provides the method of any one or more of aspects 1-24, wherein the at least one second sample comprises (a) drill cutting(s) or a core sample (aspect 25).

In aspects, the invention provides a method for analyzing the oil production properties of an oil well-associated geologic unit comprising:

a. measuring the amount of at least one first organic compound component of a first fluid sample substantially comprising a liquid, wherein the sample comprises either a formation liquid from a subject oil well or a corresponding portion of the geologic unit or a liquid that has been in contact with either such a formation liquid under conditions sufficient to transfer a detectable amount of the at least one compound, if present, to the liquid sample;

b. measuring the amount of at least one organic compound having also been measured in the first sample in at least one second sample comprising a rock obtained from the well or a from a corresponding portion of the geologic unit, which one or more compounds is/are extracted from the second sample by subjecting the second sample to gentle vacuum extraction, and analyzing the compounds extracted by application of the extraction; and c. comparing the amount of the one or more organic compounds in the first sample to the same or similar (e.g., CCSC, SSC, or both) one or more organic compounds in the one or more second samples to assess the oil production properties of the oil well (aspect 26).

In aspects, the invention provides the method of aspect 26, wherein two or more organic compounds are measured in both the first and second samples (aspect 27).

In aspects, the invention provides the method of any one or both of aspect 26 or aspect 27, wherein the amount of the organic compounds is measured in at least two second rock samples (aspect 28).

In aspects, the invention provides the method of any one or more of aspects 26-28, wherein the first sample and the second sample(s) are collected from the same well (aspect 29).

In aspects, the invention provides the method of any one or more of aspects 26-28, wherein the first sample and the second sample(s) are collected from different wells (aspect 30).

In aspects, the invention provides the method of any one or more of aspects 26-30, wherein the organic compound(s) comprise, primarily comprise, or at least substantially consist of one or more hydrocarbon(s) (aspect 31).

In aspects, the invention provides the method of aspect 31, wherein the organic compound(s) is/are (a) C4-C11 hydrocarbon(s) (aspect 32).

In aspects, the invention provides the method of aspect 32, wherein the organic compound(s) is/are (a) C5-C10 hydrocarbon(s) (aspect 33).

In aspects, the invention provides the method of aspect 33, wherein the organic compound(s) is/are (a) C6-C9 hydrocarbon(s) (aspect 34).

In aspects, the invention provides the method of aspect 34, wherein the organic compound(s) is/are (a) C6-C8 hydrocarbon(s) (aspect 35).

In aspects, the invention provides the method of any one or more of aspects 31-35, wherein the hydrocarbon(s) is/are alkane or cycloalkyl compounds (aspect 36).

In aspects, the invention provides the method of any one or more of aspects 26-36, wherein the well is divided into representative zones prior to scaling (aspect 37).

In aspects, the invention provides the method of any one or more of aspects 26-37, wherein in comparing the amount of the at least one organic compound in the first sample to the amount of the at least one same or similar (e.g., CCSC, SSC, or both) organic compound in the second sample, each sample is scaled according to its spatial contribution to the overall length of the well from which samples were collected (aspect 38).

In aspects, the invention provides the method of any one or more of aspects 26-38, wherein the well is divided into intervals, each interval being assigned an average organic compound value for each organic compound measured based on the second (rock) samples collected and measured within that interval (aspect 39).

In aspects, the invention provides the method of any one or more of aspects 26-39, wherein one or more ratio(s) are calculated comprising two or more measured organic compounds and the one or more ratios are used in the comparison of the first sample with one or more second samples (aspect 40).

In aspects, the invention provides the method of any one or more of aspects 26-40, wherein in comparing the one or more ratio(s) from the first sample to that of the one or more second sample(s), the ratio of each sample or each interval is scaled according to its spatial contribution to the overall length of the well from which samples were collected (aspect 41).

In aspects, the invention provides the method of aspect 40-41, wherein the one or more ratio(s) comprises a ration of an alkane/(alkane+cycloalkane) or alkane/cycloalkane (aspect 42).

In aspects, the invention provides the method of any one or more of aspects 28-42, wherein in the assessment of the oil production properties of the oil well comprises a determination of the relative contribution of each single location, as represented by a single sample, or each interval, as represented by an averaged set of samples, of the well (aspect 43).

In aspects, the invention provides the method of aspect 43, wherein in determining the relative contributions of each single location or each interval is determined by incorporating the constraints of the completion design of the well, only considering those locations of the well open to an influx of fluid, if present (aspect 44).

In aspects, the invention provides the method of any one or more of aspects 26-44, wherein the fluid is a produced oil (aspect 45).

In aspects, the invention provides the method of any one or more of aspects 26-44, wherein the fluid is a flowback material (aspect 46).

In aspects, the invention provides the method of any one or more of aspects 26-44, wherein the fluid is water (aspect 47).

In aspects, the invention provides the method of any one or more of aspects 26-44, wherein the fluid is a fluid inclusion (aspect 48).

In aspects, the invention provides the method of any one or more of aspects 26-44, wherein the fluid is a condensate (aspect 49).

In aspects, the invention provides the method of any one or more of aspects 26-49, wherein the at least one second sample comprises (a) drill cutting(s) or a core sample (aspect 50).

In aspects, the invention provides a method of analyzing the oil production properties of one or more parts of an oil well-associated geologic unit comprising:

a. determining the rock composition of the geologic unit comprising a subject oil well;

b. obtaining a first fluid sample essentially comprised of a liquid, such liquid comprising either a formation liquid from the subject oil well or from a corresponding portion of the geologic unit or a liquid that has been in contact with either such a formation liquid under conditions sufficient to transfer a detectable amount of the compounds, if present, to the sample;

c. obtaining one or more second solid samples that comprise rock material from the subject oil well or from a corresponding portion of the geologic unit;

d. measuring the amount of at least two organic compounds, each comprising at least four covalently bonded carbons, contained in a first sample, wherein the at least two organic compounds are compounds that: i) have the same number of carbon atoms as one another; ii) each have at least five covalently bound carbon atoms; iii) each have at least five covalently bound carbon atoms and further if each compound does not share the same number of carbon atoms, the difference in the number of carbon atoms between any two compounds is no greater than 2; iv) are not subject to interfering rock interactions with the rocks in the composition of the geologic unit in ways which are known to be significantly different from one another; or v) any one or more of (i)-(iv) are true;

e. measuring the amount of at least two of the same or similar (e.g., CCSC, SSC, or both) organic compounds as measured in the first sample in the one or more second solid samples; and f. comparing the amount of the two or more organic compounds in the first sample to the same or similar (e.g., CCSC, SSC, or both) two or more organic compounds in the one or more second samples to assess the oil production properties of the oil well (aspect 51).

In aspects, the invention provides the method of aspect 51, wherein two or more organic compounds are measured in both the first and second samples (aspect 52).

In aspects, the invention provides the method of any one or both of aspects 51 or 52, wherein the amount of the organic compounds is measured in at least two second rock samples (aspect 53).

In aspects, the invention provides the method of any one or more of aspects 51-53, wherein the first sample and the second sample(s) are collected from the same well (aspect 54).

In aspects, the invention provides the method of any one or more of aspects 51-53, wherein the first sample and the second sample(s) are collected from different wells (aspect 55).

In aspects, the invention provides the method of any one or more of aspects 51-55, wherein the organic compound(s) is/are (a) hydrocarbon(s) (aspect 56).

In aspects, the invention provides the method of aspect 56, wherein the organic compound(s) is/are (a) C4-C11 hydrocarbon(s) (aspect 57).

In aspects, the invention provides the method of aspect 57, wherein the organic compound(s) is/are (a) C5-C10 hydrocarbon(s) (aspect 58).

In aspects, the invention provides the method of aspect 58, wherein the organic compound(s) is/are (a) C6-C9 hydrocarbon(s) (aspect 59).

In aspects, the invention provides the method of aspect 59, wherein the organic compound(s) is/are (a) C6-C8 hydrocarbon(s) (aspect 60).

In aspects, the invention provides the method of any one or more of aspects 56-60, wherein the hydrocarbon(s) is/are alkane or cycloalkyl compounds (aspect 61).

In aspects, the invention provides the method of any one or more of aspects 51-61, wherein the well is divided into representative zones prior to scaling (aspect 62).

In aspects, the invention provides the method of any one or more of aspects 51-62, wherein in comparing the amount of the at least one organic compound in the first sample to the amount of the at least one same or similar (e.g., CCSC, SSC, or both) organic compound in the second sample, each sample is scaled according to its spatial contribution to the overall length of the well from which samples were collected (aspect 63).

In aspects, the invention provides the method of any one or more of aspects 51-63, wherein the well is divided into intervals, each interval being assigned an average organic compound value for each organic compound measured based on the second (rock) samples collected and measured within that interval (aspect 64).

In aspects, the invention provides the method of any one or more of aspects 51-64, wherein one or more ratio(s) are calculated comprising two or more measured organic compounds and the one or more ratios are used in the comparison of the first sample with one or more second samples (aspect 65).

In aspects, the invention provides the method of any one or more of aspects 51-65, wherein in comparing the one or more ratio(s) from the first sample to that of the one or more second sample(s), the ratio of each sample or each interval is scaled according to its spatial contribution to the overall length of the well from which samples were collected (aspect 66).

In aspects, the invention provides the method of aspect 65-66, wherein the one or more ratio(s) comprises one or more alkane/(alkane+cycloalkane) ratios or ratios of alkane/cycloalkane (aspect 67).

In aspects, the invention provides the method of any one or more of aspects 63-67, wherein in the assessment of the oil production properties of the oil well comprises a determination of the relative contribution of each single location, as represented by a single sample, or each interval, as represented by an averaged set of samples, of the well (aspect 68).

In aspects, the invention provides the method of aspect 68, wherein in determining the relative contributions of each single location or each interval is determined by incorporating the constraints of the completion design of the well, only considering those locations of the well open to an influx of fluid, if present (aspect 69).

In aspects, the invention provides the method of any one or more of aspects 51-69, wherein the fluid is a produced oil (aspect 70).

In aspects, the invention provides the method of any one or more of aspects 51-69, wherein the fluid is a flowback material (aspect 71).

In aspects, the invention provides the method of any one or more of aspects 51-69, wherein the fluid is water (aspect 72).

In aspects, the invention provides the method of any one or more of aspects 51-69, wherein the fluid is from a fluid inclusion (aspect 73).

In aspects, the invention provides the method of any one or more of aspects 51-69, wherein the fluid is a condensate (aspect 74).

In aspects, the invention provides the method of any one or more of aspects 51-74, wherein the at least one second sample comprises (a) drill cutting(s) or a core sample (aspect 75).

In aspects, the invention provides a method of analyzing the oil production properties of an oil well comprising:

a. obtaining (1) a first fluid sample substantially comprising a liquid that comprises either a formation liquid from the subject oil well or from a corresponding portion of the geologic unit, or a liquid that has been in contact with either such a formation liquid under conditions sufficient to transfer a detectable amount of the compounds, if present, to the liquid sample, and (2) a second one or more solid sample(s) that comprise rock material from the subject oil well or from a corresponding portion of the geologic unit, wherein i) the first liquid sample comprises an oil-based mud;

ii) the second one or more solid sample(s) comprise(s) a rock that has been in contact with an oil-based mud less than twenty-four hours before analysis; or iii) the first sample comprises an oil-based mud and the second one or more solid sample(s) comprise(s) a rock that has been in contact with an oil-based mud less than twenty-four hours before analysis; and b) measuring the amount of at least one organic compound in the first fluid sample;

c) measuring the amount of the same or similar (e.g., CCSC, SSC, or both) at least one organic compound associated with the second one or more solid sample(s); and d) determining the oil production properties of the oil well by comparing the amount of the first sample one or more organic compound(s) to the amount of the one or more organic compound(s) in the second one or more sample(s) (aspect 76).

In aspects, the invention provides the method of aspect 76, wherein two or more organic compounds are measured in both the first and second samples (aspect 77).

In aspects, the invention provides the method of any one or both of aspects 76 or 77, wherein the amount of the organic compounds is measured in at least two second rock samples (aspect 78).

In aspects, the invention provides the method of any one or more of aspects 76-78, wherein the first sample and the second sample(s) are collected from the same well (aspect 79).

In aspects, the invention provides the method of any one or more of aspects 76-78, wherein the first sample and the second sample(s) are collected from different wells (aspect 80).

In aspects, the invention provides the method of any one or more of aspects 76-80, wherein the organic compound(s) is/are (a) hydrocarbon(s) (aspect 81).

In aspects, the invention provides the method of aspect 81, wherein the organic compound(s) is/are (a) C4-C11 hydrocarbon(s) (aspect 82).

In aspects, the invention provides the method of aspect 82, wherein the organic compound(s) is/are (a) C5-C10 hydrocarbon(s) (aspect 83).

In aspects, the invention provides the method of aspect 83, wherein the organic compound(s) is/are (a) C6-C9 hydrocarbon(s) (aspect 84).

In aspects, the invention provides the method of aspect 84, wherein the organic compound(s) is/are (a) C6-C8 hydrocarbon(s) (aspect 85).

In aspects, the invention provides the method of any one or more of aspects 81-85, wherein the hydrocarbon(s) is/are alkane or cycloalkyl compounds (aspect 86).

In aspects, the invention provides the method of any one or more of aspects 76-86, wherein the well is divided into representative zones prior to scaling (aspect 87).

In aspects, the invention provides the method of any one or more of aspects 76-87, wherein in comparing the amount of the at least one organic compound in the first sample to the amount of the at least one same or similar (e.g., CCSC, SSC, or both) organic compound in the second sample, each sample is scaled according to its spatial contribution to the overall length of the well from which samples were collected (aspect 88).

In aspects, the invention provides the method of any one or more of aspects 76-88, wherein the well is divided into intervals, each interval being assigned an average organic compound value for each organic compound measured based on the second (rock) samples collected and measured within that interval (aspect 89).

In aspects, the invention provides the method of any one or more of aspects 76-89, wherein one or more ratio(s) are calculated comprising two or more measured organic compounds and the one or more ratios are used in the comparison of the first sample with one or more second samples (aspect 90).

In aspects, the invention provides the method of any one or more of aspects 76-90, wherein in comparing the one or more ratio(s) from the first sample to that of the one or more second sample(s), the ratio of each sample or each interval is scaled according to its spatial contribution to the overall length of the well from which samples were collected (aspect 91).

In aspects, the invention provides the method of aspect 90-91, wherein the one or more ratio(s) comprises alkane/(alkane+cycloalkane) (aspect 92).

In aspects, the invention provides the method of any one or more of aspects 88-92, wherein in the assessment of the oil production properties of the oil well comprises a determination of the relative contribution of each single location, as represented by a single sample, or each interval, as represented by an averaged set of samples, of the well (aspect 93).

In aspects, the invention provides the method of aspect 93, wherein in determining the relative contributions of each single location or each interval is determined by incorporating the constraints of the completion design of the well, only considering those locations of the well open to an influx of fluid, if present (aspect 94).

In aspects, the invention provides the method of any one or more of aspects 76-94, wherein the fluid is a produced oil (aspect 95).

In aspects, the invention provides the method of any one or more of aspects 76-94, wherein the fluid is a flowback material (aspect 96).

In aspects, the invention provides the method of any one or more of aspects 76-94, wherein the fluid is water (aspect 97).

In aspects, the invention provides the method of any one or more of aspects 76-94, wherein the fluid is fluid from a fluid inclusion (aspect 98).

In aspects, the invention provides the method of any one or more of aspects 76-94, wherein the fluid is a condensate (aspect 99).

In aspects, the invention provides the method of any one or more of aspects 76-99, wherein the at least one second sample comprises (a) drill cutting(s) or a core sample (aspect 100).

In aspects, the invention provides a method of analyzing the oil production properties of one or more parts of an oil well-associated geologic unit comprising:

a. obtaining one or more characteristics of a subject oil well that influence oil production and the location of such characteristics;

b. obtaining a first fluid sample substantially comprising a liquid that comprises either a formation liquid from the subject oil well or from a corresponding portion of the geologic unit or a liquid that has been in contact with either such a formation liquid under conditions sufficient to transfer a detectable amount of the compounds, if present, to the liquid sample;

c. obtaining a plurality of solid samples that comprise rock material from different zones of the subject oil well or from a corresponding portion of the geologic unit;

d. measuring the amount of at least two organic compounds contained in a first fluid sample;

e. optionally measuring the amount of at least two of the same or similar (e.g., CCSC, SSC, or both) organic compounds as measured in a first fluid sample associated with the one or more second solid samples;

f. evaluating the relationship between the amount of the first sample organic compounds and second sample organic compounds to identify zones of the oil well that are expected to contribute to oil production;

g. applying a scaling factor to the evaluation of step (e) based on the location and nature of the characteristics to provide a modified map of zones of oil production capability in the subject well (aspect 101).

In aspects, the invention provides the method of aspect 101, wherein two or more organic compounds are measured in both the first and second samples (aspect 102).

In aspects, the invention provides the method of any one or both of aspects 101 or 102, wherein the amount of the organic compounds is measured in at least two second rock samples (aspect 103).

In aspects, the invention provides the method of any one or more of aspects 101-103, wherein the first sample and the second sample(s) are collected from the same well (aspect 104).

In aspects, the invention provides the method of any one or more of aspects 101-103, wherein the first sample and the second sample(s) are collected from different wells (aspect 105).

In aspects, the invention provides the method of any one or more of aspects 101-105, wherein the organic compound(s) is/are (a) hydrocarbon(s) (aspect 106).

In aspects, the invention provides the method of aspect 106, wherein the organic compound(s) is/are (a) C4-C11 hydrocarbon (aspect 107).

In aspects, the invention provides the method of aspect 107, wherein the organic compound(s) is/are (a) C5-C10 hydrocarbon (aspect 108).

In aspects, the invention provides the method of aspect 108, wherein the organic compound(s) is/are (a) C6-C9 hydrocarbon (aspect 109).

In aspects, the invention provides the method of aspect 109, wherein the organic compound(s) is/are (a) C6-C8 hydrocarbon (aspect 110).

In aspects, the invention provides the method of any one or more of aspects 106-110, wherein the hydrocarbon(s) is/are alkane or cycloalkyl compounds (aspect 111).

In aspects, the invention provides the method of any one or more of aspects 101-111, wherein the well is divided into representative zones prior to scaling (aspect 112).

In aspects, the invention provides the method of any one or more of aspects 101-112, wherein in comparing the amount of the at least one organic compound in the first sample to the amount of the at least one same or similar (e.g., CCSC, SSC, or both) organic compound in the second sample, each sample is scaled according to its spatial contribution to the overall length of the well from which samples were collected (aspect 113).

In aspects, the invention provides the method of any one or more of aspects 101-113, wherein the well is divided into intervals, each interval being assigned an average organic compound value for each organic compound measured based on the second (rock) samples collected and measured within that interval (aspect 114).

In aspects, the invention provides the method of any one or more of aspects 101-114, wherein one or more ratio(s) are calculated comprising two or more measured organic compounds and the one or more ratios are used in the comparison of the first sample with one or more second samples (aspect 115).

In aspects, the invention provides the method of any one or more of aspects 101-115, wherein in comparing the one or more ratio(s) from the first sample to that of the one or more second sample(s), the ratio of each sample or each interval is scaled according to its spatial contribution to the overall length of the well from which samples were collected (aspect 116).

In aspects, the invention provides the method of aspect 115-116, wherein the one or more ratio(s) comprises a ratio of alkane/(alkane+cycloalkane) compounds or alkane/cycloalkane compounds (aspect 117).

In aspects, the invention provides the method of any one or more of aspects 113-117, wherein in the assessment of the oil production properties of the oil well comprises a determination of the relative contribution of each single location, as represented by a single sample, or each interval, as represented by an averaged set of samples, of the well (aspect 118).

In aspects, the invention provides the method of aspect 118, wherein in determining the relative contributions of each single location or each interval is determined by incorporating the constraints of the completion design of the well, only considering those locations of the well open to an influx of fluid, if present (aspect 119).

In aspects, the invention provides the method of any one or more of aspects 101-119, wherein the fluid is a produced oil (aspect 120).

In aspects, the invention provides the method of any one or more of aspects 101-119, wherein the fluid is a flowback material (aspect 121).

In aspects, the invention provides the method of any one or more of aspects 101-119, wherein the fluid is water (aspect 122).

In aspects, the invention provides the method of any one or more of aspects 101-119, wherein the fluid is from a fluid inclusion (aspect 123).

In aspects, the invention provides the method of any one or more of aspects 101-119, wherein the fluid is a condensate (aspect 124).

In aspects, the invention provides the method of any one or more of aspects 101-124, wherein the at least one second sample comprises (a) drill cutting(s) or a core sample (aspect 125).

In aspects, the invention provides a method of evaluating the oil producing capability of at least one part of an oil well comprising:

a. collecting a first sample of a fluid essentially comprised of a liquid from the oil well or from a location that has been in contact with at least one part of the geologic unit within which the oil well has been placed under conditions permitting the transfer of a quantifiable amount of oil-associated compounds into the first liquid material;

b. collecting a second sample comprising rock from one or more locations in at least one part of the well;

c. subjecting the first fluid sample to an analysis that identifies the approximate amount of about 3-9 compounds in the fluid, the 3-9 compounds consisting of C4-C11 alkane and cycloalkyl compounds;

d. subjecting the second sample to an analysis that identifies the approximate amount of at least 2 of the same 3-9 chemical species as identified in the fluid sample; and e. evaluating the oil producing capability of the at least one part by evaluating the amount of the measured compounds in the first sample to the amounts of the measured compounds in the second sample, wherein the presence of most or all of the measured compounds in both the first sample and the second sample is indicative of oil being associated with at least one part of the well (aspect 126).

In aspects, the invention provides a method for allocating a relative proportion of productivity to each geographically defined segment of a plurality of geographically defined segments within an oil well comprising:

a. collecting a sample of a fluid comprised substantially of a liquid that comprises either a formation liquid from the subject oil well or from a corresponding portion of larger geologic unit, or a liquid that has been in contact with either such a formation liquid under conditions sufficient to transfer a detectable amount of the compounds, if present, to the liquid sample;

b. collecting a series of non-liquid samples comprising rock from a plurality of locations of the oil well;

c. subjecting the liquid material to an analysis that identifies the approximate amount of about 3-9 hydrocarbon species in the liquid consisting of C4-C11 alkane and cycloalkyl compounds;

d. subjecting the series of non-liquid material samples to an analysis that identifies the approximate amount of at least 2 of the same or similar 3-9 chemical species consisting of C4-C11 alkane and cycloalkyl compounds in each of the series of second samples;

e. determining the ratio between (i) the alkane and (ii) the sum of total alkane and cycloalkyl compounds having the same or similar number of carbons within each of the fluid and series of non-liquid material samples;

f. dividing the well bore length into location intervals;

g. combining the series of ratios calculated in (e) for each of the non-liquid material samples collected from within each of the defined intervals established in (f) so as to establish an average ratio for each of the defined intervals in (f) ("interval ratios");

h. assigning each interval ratio established in (g) a scaling factor so as to assign each location interval within the well a scaled representative of its overall spatial contribution to the total length of the well bore to establish a first set of representative bore hole interval values ("length-weighted interval ratios");

i. applying a numerical method analysis to the collection of length-weighted interval ratios from (h) capable of iterating various combinations of applied scaling factors and comparing the results of such iterations to a target value, the target value being derived from the fluid sample, with the scaling factor as an adjustable variable;

j. identifying the combination of scaling factors, which, when applied to each interval ratio, results in a scaling of the bore intervals such that when all interval ratios are considered, the combination most closely represents the profile of the fluid sample;

k. utilizing the scaling of (j) to establish the relative proportion of productivity of each interval of the well to the fluid sample (aspect 127).

In aspects, the invention provides a method for allocating a relative proportion of productivity to each interval of a plurality of intervals within an oil well comprising:

a. collecting a sample of a fluid essentially comprised of a liquid from the oil well or from a location that has been in contact with at least one part of the geologic unit within which the oil well has been placed under conditions permitting the transfer of a quantifiable amount of oil-associated compounds into the first liquid material;

b. collecting a series of non-liquid material samples comprising rock from a plurality of locations of the oil well;

c. subjecting the fluid sample to an analysis that identifies the approximate amount of about 3-9 chemical species in the liquid consisting of C4-C11 alkane and cycloalkyl compounds;

d. subjecting the series of non-liquid samples to an analysis that identifies the approximate amount of at least 2 of the same or similar 3-9 chemical species consisting of C4-C11 alkane and cycloalkyl compounds in each of the series of second samples;

e. determining the ratio between (i) the total alkane and (ii) the sum of total alkane and cycloalkyl compounds having the same or similar carbon number within each of the fluid and series of non-liquid material samples;

f. assigning a scaling factor to each sample ratio calculated in (e) for the series of non-liquid material samples representative of each sample's relative representation of the overall length of the well, such a scaling factor calculated by dividing the total number of samples by the total length of the well;

g. applying a numerical method analysis to the collection of length-scaled sample ratios from (f) capable of iterating various combinations of applied scaling factors and comparing the results of such iterations to a target value, the target value being derived from the fluid sample; with the scaling factor as an adjustable variable;

h. identifying the combination of scaling factors, which, when applied to each sample ratio, results in a scaling of the bore locations such that when all sample ratios are considered, the combination most closely represents the profile of the first material;

i. utilizing the scaling of (h) to establish the relative proportion of productivity of each location of the well from which each sample was taken to the fluid sample (aspect 128).

In aspects, the invention provides the method of aspect 128, wherein after determining the ratio between (i) the alkane and (ii) the sum of total alkane and cycloalkyl compounds having the same or similar carbon number within each of the fluid and series of non-liquid material samples:

a. the well bore length is divided into location intervals;

b. the ratios calculated for the non-liquid samples in (e) from within each location interval are averaged so as to create a representative interval ratio;

c. a scaling factor is applied to each interval ratio representative of the intervals' overall spatial contribution to the total length of the well bore so as to create a first set of representative bore hole interval values ("length-scaled zone ratios");

d. the numerical method described in step (g) is applied to the length-scaled interval ratios with the scaling factor for each set as an adjustable variable;

e. identifying the combination of scaling factors, which, when applied to each interval ratio, results in a scaling of the bore intervals such that when all interval ratios are summed, the combination most closely represents the profile of the fluid sample; and f. utilizing the scaling of (e) to establish the relative proportion of productivity of each location of the well from which each sample was taken to the fluid sample (aspect 129).

In aspects, the invention provides the method of any one or more of aspects 127-129, wherein the method is predictive of the relative proportion of productivity of a plurality of intervals of a yet-to-be completed well (aspect 130).

In aspects, the invention provides the method of any one or more of aspects 127-129, wherein the method is predictive of the relative proportion of productivity of a plurality of zones of a completed well (aspect 131).

In aspects, the invention provides the method of any one or more of aspects 126-131, wherein in place of evaluating the ratio of measured compounds in the liquid sample to the rock sample, direct measurements of each of the compounds are evaluated (aspect 132).

In aspects, the invention provides the method of any one or more of aspects 126-132, wherein in applying the numerical method analysis, the analysis is restricted by limiting the analysis according to one or more known characteristics of the well (aspect 133).

In aspects, the invention provides the method of aspect 133, wherein a known characteristic of the well is one or more locations within the well that are known to be accessible to a flow of oil if a flow of oil is present (aspect 134).

In aspects, the invention provides the method of any one or more of aspects 126-134, wherein the fluid sample and the series of non-liquid samples are collected from the same well (aspect 135).

In aspects, the invention provides the method of any one or more of aspects 126-134, wherein the fluid sample and the series of non-liquid samples are collected from different wells capable of accessing the same reservoir(s) from which the fluid sample is sourced (aspect 136).

In aspects, the invention provides the method of any one or more of aspects 126-136, wherein the fluid comprises an oil fraction (aspect 137).

In aspects, the invention provides the method of any one or more of aspects 126-136, wherein the fluid is extracted from an oil inclusion or oil-containing geologic unit (aspect 138).

In aspects, the invention provides the method of any one or more of aspects 126-136, wherein the fluid is flowback material (aspect 139).

In aspects, the invention provides the method of any one or more of aspects 126-136, wherein the fluid is a condensate (aspect 140).

In aspects, the invention provides the method of any one or more of aspects 126-136, wherein the fluid is water (aspect 141).

In aspects, the invention provides the method of aspect 141, wherein the resulting relative proportion of productivity of each individual location or each interval to the water indicates which locations of the well bore make the highest contribution(s) to the source of water (aspect 142).

In aspects, the invention provides the method of any one or more of aspects 126-140, wherein the method is predictive of the productivity of different intervals of a planned well yet-to-be drilled (aspect 143).

In aspects, the invention provides the method of any one or more of aspects 126-143, wherein the series of non-liquid material samples are drill cuttings or core samples (aspect 144).

In aspects, the invention provides the method of any one or more of aspects 126-144, wherein the measurement of selected hydrocarbons on each of the liquid material and the series of non-liquid material samples comprises (a) gentle vacuum extraction at approximately room temperature, (b) cryogenic compound capture and separation through gradual warming, or both (a) and (b) and mass spectrometry (aspect 145).

In aspects, the invention provides the method of aspect 145, wherein the hydrocarbons are hydrocarbons comprising between 4 and 11 carbons (aspect 146).

In aspects, the invention provides the method of aspect 146, wherein the hydrocarbons are hydrocarbons having between 4 and 10 carbons (aspect 147).

In aspects, the invention provides the method of aspect 147, wherein the hydrocarbons are hydrocarbons having between 6 and 10 carbons (aspect 148).

In aspects, the invention provides the method of aspect 148, wherein the hydrocarbons are hydrocarbons having between 6 and 8 carbons (aspect 149).

In aspects, the invention provides the method of any one or more of aspects 146-149, wherein instead of alkanes and cycloalkanes, the specific species of hydrocarbons are selected from the group comprising non-aromatic linear and cyclic organic compounds (aspect 150).

In aspects, the invention provides the method of any one or more of aspects 126-150, wherein (a) at least one of the fluids analyzed as a first sample is an oil-based mud, (b) the second non-liquid sample comprises a plurality of well cuttings from a well in contact with an oil-based mud, or (c) at least one of the fluids is an oil-based mud and the second sample comprises a plurality of well cuttings that have been in contact with an oil-based mud (aspect 151).

In aspects, the invention provides the method of any one or more of aspects 126-151, wherein the method comprises repeating the method on two or more wells from a region and comparatively evaluating the results of each well so as to characterize the petroleum producing characteristics of the region (aspect 152).

In aspects, the invention provides a method of predicting the highest producing zones of a yet-to-be completed oil well comprising:

a. collecting a series of non-liquid material samples representative of a plurality of locations across the yet-to-be completed oil well;

b. collecting a fluid essentially comprised of a liquid from the oil well or from a location that has been in contact with at least one part of the geologic unit within which the oil well has been placed under conditions permitting the transfer of a quantifiable amount of oil-associated compounds into the first liquid material from a well a) within the same geologic unit; b) within the same drilling pad; c) within 1 mile; d) having access to the same reservoir(s); or any combination of (a), (b), or (c); and c. directly measuring the amount of selected hydrocarbons within each of the fluid and the series of non-liquid samples; or d. directly measuring the amount of selected hydrocarbons having the same or similar carbon number within each of the fluid and series of non-liquid samples and further calculating one or more ratios between selected one or more hydrocarbons for each of the fluid and the series of non-liquid samples; and e. dividing the well bore length into location intervals;

f. determining the average absolute value or average ratio of the one or more selected hydrocarbons from the non-liquid samples from (b) for each of the defined location intervals;

g. assigning each value from (d) a scaling factor so as to assign each location interval a scale representative of its overall spatial contribution to the total length of the well to establish a collection of representative well interval values;

h. applying, to the collection of representative bore hole zone values from (e), a numerical method analysis capable of iterating various combinations of applied scaling factors, the scaling factors being an adjustable variable, and comparing the results of such iterations to a target value, wherein the target value is derived from the fluid sample; and further restricting the analysis according to other known one or more characteristics of the well;

i. Identifying the combination of scaling factors, which, when applied to each respective representative well interval values, results in a scaling of the well interval values, such that when all interval samples are combined, the combination most closely represents the profile of the fluid material; and j. utilizing the scaling of (g) to predict the highest producing zones of the yet-to-be completed oil well (aspect 153).

In aspects, the invention provides the method of aspect 153, wherein a known characteristic of the well is one or more locations within the well that are known to be accessible to a flow of oil, if present (aspect 154).

In aspects, the invention provides the method of any one or more of aspects 126-150, or 152-154, wherein the fluid sample, the series of non-liquid samples, or both the liquid and the series of non-liquid samples are taken from one or more wells drilled with a water-based drilling mud system (aspect 155).

In aspects, the invention provides the method of any one or more of aspects 126-155, wherein one of the fluid sample or the series of non-liquid samples is taken from a well drilled with a water-based drilling mud system and the other of the liquid sample or the series of non-liquid samples is taken from a well drilled with an oil-based drilling mud system (aspect 156).

In aspects, the invention provides the method of any one or more of aspects 1-156, wherein the method does not comprise subjecting any collected sample to an analysis using gas chromatography (GC); GC-mass spectrophotometry (MS); Fourier-transform ion cyclotron resonance (FTICR)-MS; thin layer chromatography (TLC); 2D TLC; capillary electrophoresis (CE); high performance liquid chromatography (HPLC); Fourier-transform infrared (FTIR) spectrophotometry; x-ray fluorescence (XRF); atomic absorption spectrometry (AAS); inductively coupled plasma (ICP)-MS; ion chromatography (IC); nuclear magnetic resonance (NMR); two-dimensional gas chromatography and time-of-flight mass spectrometry (GC×GC-TOFMS); saturate, aromatic, resin, and asphaltene (SARA); carbon, hydrogen, nitrogen, sulfur and oxygen content (CHNOS); elemental analysis; GC/infrared (IR)-MS, or any combinations thereof (aspect 157).

In aspects, the invention provides the method of any one or more of aspects 1-157, wherein a computer is used in the performance of the method to (a) receive results from one or more analytical instruments used in the method to measure one or more organic compounds; (b) to perform the analysis of the method described in aspect 127; (c) to provide an output comprising the results of the analysis of (b); or (d) all of (a-c) (aspect 158).

In aspects, the invention provides the method of aspect 158, wherein the output is utilized to (a) direct an existing petroleum operation; (b) select a location for drilling a lateral oil well; (c) select a site or location for the drilling of a new vertical or lateral petroleum wells; (d) select a site or location for fracking of an existing petroleum well; or (e) any combination of any or all thereof (aspect 159).

In aspects, the invention provides a method of selecting a location for drilling a lateral oil well based on the comparative analysis data resulting from the application of any one or more methods described in aspects 1-159 (aspect 160).

In aspects, the invention provides a method of utilizing comparative analysis methods described in any one or more of aspects 1-159 to select a site or location for the drilling of a new vertical or lateral petroleum wells or also or alternatively to select a site or location for fracking of an existing petroleum well (aspect 161).

In aspects, the invention provides the method of any one or more of aspects 1-161, wherein the method comprises determining the amount of release resistant water attributable to one or more zones of an oil well (aspect 162).

In aspects, the invention provides a method of analyzing an oil well production capability comprising determining two or more zones of an oil well based on the amount of release resistant water associated with each zone and using such information to map zones of potential oil productivity, the method optionally comprising using real world data concerning oil production as a factor in such evaluation (aspect 163).

In aspects, the invention provides the method of aspect 163, wherein the method further comprises incorporation of comparative data resulting from the application of any one or more methods described in aspects 1-159 (aspect 164).

In aspects, the invention provides a method of selecting a location for drilling a lateral oil well based on the comparative analysis data resulting from the application of the method of any one or more of aspects 162-164 (aspect 165).

In aspects, the invention provides a method of utilizing comparative analysis methods described in any one or more of aspects 162-164 to select a site or location for the drilling of a new vertical or lateral petroleum wells or also or alternatively to select a site or location for fracking of an existing petroleum well (aspect 166).

In aspects, the invention provides a method of utilizing comparative analysis methods described in any one or more of aspects 1-159 to identify oil-producing potential of a non-producing (dry) well (aspect 167).

In aspects, the invention provides a method according to any one or more of aspects 1-159, wherein the first fluid sample is a gas sample, and the method is applied to carbon capture storage reservoirs to determine whether leaking is occurring (aspect 168).

In aspects, the invention provides the method according to aspect 168, wherein the first fluid sample is carbon dioxide (aspect 169).

In aspects, the invention provides the method according to any one or both of aspects 168 or 169, wherein the method is capable of determining the location of a carbon dioxide leak if a carbon dioxide leak is present (aspect 170).

In aspects, the invention provides the method according to any one or more of aspects 1-159, wherein the method is applied to the characterization of a petroleum well, a carbon capture storage reservoir, or a geothermal well (aspect 171).

In aspects, the invention provides the method according to any one or more of aspects 1-159, wherein the method is applied to characterize $CO_2$ migration in enhanced oil recovery operations (aspect 172).

In aspects, the invention provides the method according to any one or more of aspects 1-159 or aspects 167-172, wherein the compounds analyzed as a part of the method are selected from a group comprising $CO_2$, COS, $CS_2$, $SO_2$, $H_2S$, C12, C13, or oxygen isotopes such as O16 and O18 (aspect 173).

In aspects, the invention provides the method according to any one or more of aspects 1-159 or aspects 167-172, wherein condensates comprise hydrocarbons that are in a liquid phase under surface conditions however reside in the subsurface in a gas phase (aspect 174).

In aspects, the invention provides the method according to any one or more of aspects 1-159 or aspects 167-172, wherein application of the method does not include application of a Monte Carlo iteration (aspect 175).

In aspects, the invention provides a method of evaluating the oil producing capability of at least one part of a well comprising:

(a) collecting a first sample of a fluid forming a first fluid material sample essentially comprised of a fluid from the well or from a location that has been in contact with at least one part of the geologic unit within which the well has been placed under conditions permitting the flow of a quantifiable amount of a number of oil-associated compounds into the first fluid material sample;

(b) collecting a second sample comprising solid material from a location in the well or from a location within the geologic unit in fluid communication with the oil well;

(c) subjecting the first fluid material sample to an analysis that identifies the approximate amount of 1-9 organic compound(s) in the fluid material sample selected from a group of less than 120 possible organic compounds;

(d) subjecting the second sample to an analysis that identifies the approximate amount of at least one of the 1-9 organic compound(s) in the second sample comprising subjecting the second sample to a negative pressure of about $1 \times 10^{-2}$ millibars or less applied at about room temperature for about 3-30 minutes, each of the second sample-derived organic compounds (i) corresponding to an organic compound in the first fluid sample or (ii) being a carbon-compositionally similar and structurally similar compound to the compound(s) in the first sample and differing from the compound(s) in the first sample by 0, 1, or 2 carbon atoms;

(e) evaluating the oil producing capability of the location of the at least second sample by comparing the amount of the measured compound(s) in the first fluid material sample to the amounts of the measured corresponding carbon-compositionally similar and structurally similar organic compound(s) in the second sample, wherein the greater presence of corresponding or structurally similar organic compounds in the second sample with respect to organic compounds identified in the first fluid material sample indicates an increased likelihood of the location from which the second sample was collected contributing to the first fluid material produced by the well;

(f) determining whether the comparison in step (e) is sufficient to identify the characteristics of the first fluid material as being established by material contributed from the location at which the second sample was collected;

(g) in the event the comparison in step (e) is not sufficient to identify the characteristics of the first fluid material as being established by material contributed from the location at which the second sample was collected, collecting at least one additional sample comprising solid material from at least one additional location of the geologic unit;

(h) subjecting the one or more additional samples to an analysis that identifies the approximate amount of at least one of the 1-9 organic compound(s) in each of the one or more additional samples comprising subjecting the one or more additional samples to a negative pressure of about $1 \times 10^{-2}$ millibars or less applied at about room temperature for about 3-30 minutes, each of the organic compounds derived from the one or more additional samples (i) corresponding to an organic compound in the first fluid material sample or (ii) being a carbon-compositionally similar and structurally similar compound to the compound(s) in the first fluid material sample and differing from the compound(s) in the first sample by 0, 1, or 2 carbon atoms; and (i) evaluating the oil producing capability of the at least one additional location of the geologic unit represented by the location from which each of the at least one additional samples was collected by comparing the amount of the measured compound(s) in the first fluid material sample to the amounts of the measured corresponding carbon-compositionally similar and structurally similar organic compound(s) in each of the additional samples, wherein an increased presence of corresponding or structurally similar organic compounds in one or more of the additional samples with respect to organic compounds identified in the first sample indicates a higher likelihood of the location from which such one or more sample(s) was collected contributing to the characteristics of the first fluid material (aspect 176).

In aspects, the invention provides the method of aspect 176, wherein 2-9 organic compounds are measured in the first fluid material sample and any additional solid material sample (aspect 177).

In aspects, the invention provides the method of any one or both of aspects 176-177, wherein the first liquid material sample is a produced oil and the second, solid material, sample and any additional solid material samples comprise drill cuttings or core samples (aspect 178).

In aspects, the invention provides the method of any one or more of aspects 176-178, wherein the method comprises measuring organic compounds in at least two solid material samples, each of the at least two solid material samples collected at intervals of no more than 120 feet (aspect 179).

In aspects, the invention provides the method of any one or more of aspects 176-179, wherein the first fluid material sample, the second, solid material, sample and any additional solid material samples are collected from a single well (aspect 180).

In aspects, the invention provides the method of any one or more of aspects 176-179, wherein the first fluid material sample and at least one of the second, solid material, sample and any additional solid material sample(s) are collected from different wells (aspect 181).

In aspects, the invention provides the method of any one or more of aspects 176-179, wherein at least most of the organic compounds in the first fluid material sample and at least the second sample comprise a detectable amount of C4-C11 hydrocarbons (aspect 182).

In aspects, the invention provides the method of any one or more of aspects 176-182, wherein the organic compounds are C5-C10 hydrocarbon(s) (aspect 183).

In aspects, the invention provides the method of any one or more of aspects 176-183, wherein at least most of the C4-C10 hydrocarbon consist of alkane or cycloalkyl compound(s) (aspect 184).

In aspects, the invention provides the method of any one or more of aspects 176-180, wherein the method comprises (a) dividing the well from which the first fluid material sample is collected into representative zones prior to the analysis of solid material samples from the well and (b) providing an initial scaling factor for each solid material sample analyzed in the method according to its spatial contribution to the overall length of the well from which samples were collected (aspect 185).

In aspects, the invention provides the method of any one or more of aspects 176-185, wherein only zones associated with locations of the well open to an influx of fluid are considered in determining the relative contributions of each part of the well (aspect 186).

In aspects, the invention provides the method of any one or more of aspects 176-186, wherein the method comprises establishing one or more ratios comprising amounts of alkane/(alkane+cycloalkane) compounds in the first fluid material sample, second sample, and any subsequent samples, wherein the presence of most or all of the measured compounds identified in the first fluid material sample within the second, solid material, sample and any additional solid material samples, or any combination thereof is indicative of oil being associated with the part of the well from which such second or additional sample(s) were collected (aspect 187).

In aspects, the invention provides the method of any one or more of aspects 176-187, wherein the method is used to select one or more locations for a) drilling a new lateral or vertical well, b) directing drilling operations on an existing lateral or vertical well, c) fracking an existing well, or d) any combination of (a)-(c), based on the comparative analysis data resulting from the application of the method (aspect 188).

In aspects, the invention provides the method of any one or more of aspects 176-188, wherein the second, solid material, sample and any additional samples are subjected to an analysis that identifies the approximate amount of at least two organic compounds measured in the first fluid material sample that each comprise at least four covalently bonded carbons, wherein the at least two organic compounds are compounds that: i) have the same number of carbon atoms as one another; ii) each have at least five covalently bound carbon atoms; iii) each have at least five covalently bound carbon atoms and further if each compound does not share the same number of carbon atoms, the difference in the number of carbon atoms between any two compounds is no greater than 2; iv) are not subject to interfering rock interactions with the rocks of the geologic unit in ways which are known to be significantly different from one another; or v) any one or more of (i)-(iv) are true (aspect 189).

In aspects, the invention provides the method of any one or more of aspects 176-189, wherein the first fluid material sample comprises a produced condensate (aspect 190).

In aspects, the invention provides a method of assigning a highly contributing source of produced hydrocarbon liquid samples comprising:

(a) collecting a first sample of a fluid essentially comprised of a fluid from an oil well or from a location known to be or have been in contact with at least one part of a geologic unit within which the well is located under conditions permitting the flow of a quantifiable amount of a number of oil-associated compounds into the first fluid material;

(b) collecting a sample of a second fluid establishing a second fluid sample collected from a location known to be or have been in contact with at least one part of the geologic unit within which the well has been placed under conditions permitting the flow of a quantifiable amount of a number of oil-associated compounds into the second fluid material;

(c) subjecting the first fluid sample to an analysis that identifies the approximate amount of 1-9 organic compound(s) in the fluid sample selected from a group of less than 120 possible organic compounds;

(d) subjecting the second fluid sample to an analysis that identifies the approximate amount of 1-9 organic compound(s) in the fluid sample selected from a group of less than 120 possible organic compounds;

(e) evaluating the likelihood of the first fluid sample and second fluid sample originate from the same source by comparing the amount of the measured compound(s) in the first fluid sample to the amounts of the measured corresponding carbon-compositionally similar and structurally similar organic compound(s) in the second fluid sample, wherein the greater presence of corresponding or structurally similar organic compounds in the second fluid sample with respect to organic compounds identified in the first sample increases the likelihood of the first fluid sample and the second fluid sample having the same location of origin;

(f) determining whether the comparison in step (e) is sufficient to identify the characteristics of the first fluid sample as being contributed by fluid located at the location from which the second fluid sample was collected;

(g) in the event the comparison in step (e) is not sufficient to identify the characteristics of the first fluid sample as being contributed by fluid located at the location from which the second fluid sample was collected, collecting one or more additional fluid samples from one or more location(s) that are or have been in contact with at least one part of the geologic unit within which the well has been placed under conditions permitting the flow of a quantifiable amount of a number of oil-associated compounds into the one or more fluid samples;

(h) subjecting the one or more additional fluid samples to an analysis that identifies the approximate amount of 1-9 organic compound(s) in the one or more additional fluid samples selected from a group of less than 120 possible organic compounds; and (i) evaluating the likelihood of the first fluid sample and the one or more additional samples having the same location of origin by comparing the amount of the measured compound(s) in the first fluid sample to the amounts of the measured corresponding carbon-compositionally similar and structurally similar organic compound(s) in the one or more additional samples, wherein the greater presence of corresponding or structurally similar organic compounds in one or more of the one or more additional samples with respect to organic compounds identified in the first sample increases the likelihood of the first fluid sample and one or more of the one or more additional samples having the same location of origin (aspect 191).

In aspects, the invention provides the method of aspect 191, wherein the first fluid sample comprises a produced condensate (aspect 192).

In aspects, the invention provides the method of any one or both of aspect 191 and 192, wherein steps (c), (d), and (h) comprise subjecting the fluid samples to an analysis that identifies the approximate amount of at least one of the 1-9 organic compound(s) in the second sample comprising subjecting the second sample to a negative pressure of about $1 \times 10\text{-}2$ millibars or less applied at about room temperature for about 3-30 minutes (aspect 193).

In aspects, the invention provides the method of any one or more of aspects 191-193, wherein the method comprises analyzing fluid samples collected from a single well and (a) dividing the well into representative zones prior to the analysis of fluid samples from the well and (b) providing an initial scaling factor for each fluid sample analyzed in the method according to its spatial contribution to the overall length of the well from which samples were collected (aspect 194).

In aspects, the invention provides the method of any one or more of aspects 191-194, wherein only zones associated with locations of the well open to an influx of fluid are considered in determining the relative contributions of each part of the oil well (aspect 195).

In aspects, the invention provides the method of any one or more of aspects 191-195, wherein the method comprises establishing one or more ratios comprising amounts of alkane/(alkane+cycloalkane) compounds in the first fluid sample, second fluid sample, and any subsequent additional samples, wherein the presence of most or all of the measured compounds identified in the first fluid sample present in the second fluid sample, or one or more of any additional samples is indicative of any such samples having the same location of origin (aspect 196).

In aspects, the invention provides the method of any one or more of aspects 1-196, wherein the method is used to select one or more locations for a) drilling a new lateral or vertical oil, b) directing drilling operations on an existing lateral or vertical oil well, c) fracking an existing oil well, or d) any combination of (a)-(c), based on the comparative analysis data resulting from the application of the method (aspect 197).

In aspects, the invention provides the method of any one or more of aspects 1-197, wherein comparing the amounts comprises generating a ratio and comparing the ratio against a similar ratio generated by the second sample or against the standard (aspect 198).

In aspects, the invention provides the method according to any one of aspects 1-198, wherein a fluid sample is a condensate sample, and the condensate(s) include hydrocarbons that are in a liquid phase under surface conditions however reside in the subsurface in a gas phase (aspect 199).

In aspects, the invention provides the method according to any one of aspects 1-199, wherein application of the method does not include application of a Monte Carlo iteration (aspect 200).

What is claimed is:

1. A method of evaluating the oil-producing capability of at least one part of a geologic unit comprising:

(a) analyzing the amount of each of 1-9 organic compounds in a first fluid material sample from a fluid sample location in the geologic unit, the analysis comprising subjecting the first fluid material sample to a process that determines the amount of each of the 1-9 organic compounds in the first fluid material sample;

(b) analyzing the amount of each of 1-9 organic compounds in a second solid material sample from a solid sample location that is (1) in an oil well in the geologic unit or (2) from a location within the geologic unit that is not in an oil well but is in fluid communication with the fluid sample location, each of the 1-9 organic compounds in the second solid material sample being identified as corresponding to one of the 1-9 organic compounds in the first fluid material sample by (A) having the same composition and structure as one of the 1-9 organic compounds in the first fluid material sample or (B) being a compound that differs from the 1-9 organic compounds in the first fluid material sample but has a carbon atom content that differs from one of the organic compounds of the 1-9 organic compounds in the first fluid material sample by 0, 1, or 2 carbon atoms, comprising subjecting the second solid material sample to a process that determines the amount of each of the 1-9 organic compounds in the second solid material sample;

(c) comparing the amount of each of the 1-9 organic compounds in the first fluid material sample to the amount of the corresponding 1-9 organic compound in the second solid material sample;

(d) determining from the comparison performed in step (c) whether at least 50% of the first fluid material sample originates from the solid sample location, and if at least 50% of the first fluid material sample originates from the solid sample location, using the comparison of step (c) to evaluate the oil-producing capability of the solid sample location:

(e) if the result of the determination of step (d) is that less than 50% of the first fluid material sample originates from the solid sample location, analyzing the amount of each of 1-9 organic compounds in each of one or more additional solid material samples from one or more additional solid sample locations that are (1) in an oil well in the geologic unit or (2) from one or more locations that are not in an oil well of the geologic unit but are in fluid communication with the fluid sample location, each of the 1-9 organic compounds in the one or more additional solid material samples being identified as corresponding to one of the 1-9 organic compounds in the first fluid material sample by (A) having the same composition and structure as one of the 1-9 organic compounds in the first fluid material sample or (B) being a compound that differs from the 1-9 organic compounds in the first fluid material sample but has a carbon atom content that differs from a corresponding organic compound of the 1-9 organic compounds in the first fluid material sample by 0, 1, or 2 carbon atoms, by subjecting each of the one or more additional solid material samples to a process that determines the amount of each of the 1-9 organic compounds in each of the one or more additional solid material samples; and (f) if step (e) of the method is performed, evaluating the oil-producing capability of the one or more additional solid sample locations by comparing the amount of each of the 1-9 organic compounds in the first fluid material sample to the amount of each of the corresponding 1-9 organic compounds in the one or more additional solid material samples.

2. The method of claim 1, wherein the method further comprises:

(h) at least 95% of the first fluid material sample is composed of a fluid originating from an oil well in the geologic unit or from a location that has been in contact with at least one part of the geologic unit within which the well has been placed under conditions permitting the flow of a quantifiable amount of oil-associated compounds into the first fluid material sample; and (i) (1) determining the amount of each of the 1-9 organic compounds present in the second solid material sample collected by a process that comprises subjecting the second solid material sample to a negative pressure of $1\times10^{-2}$ millibars or less applied at about room temperature for about 3 minutes to about 30 minutes or (2) determining the amount of each of the 1-9 organic compounds present in the one or more additional solid material samples by a process that comprises subjecting the one or more additional solid material samples to a negative pressure of $1\times10^{-2}$ millibars or less applied at about room temperature for about 3 minutes to about 30 minutes.

3. The method of claim 2, wherein the step of evaluating the oil-producing capability of the solid sample location or one or more additional solid sample locations comprises analyzing the amount of each of 2-9 organic compounds in the first fluid material sample as well as in the second solid material sample or any of the one or more additional solid material samples.

4. The method of claim 3, wherein the method comprises determining the amount of each of the 2-9 organic compounds in each sample of two or more additional solid material samples, wherein each of the two or more additional solid material samples is collected from a separate location from among two or more locations in the geologic unit, wherein the two or more locations are separated by no more than 120 feet.

5. The method of claim 4, wherein the first fluid material sample is collected from an oil well, and the two or more additional solid material samples are collected from locations spanning most of the full length of the oil well.

6. The method of claim 3, wherein the method further comprises the steps of (1) calculating a ratio of the amounts of at least 2 organic compounds of the 2-9 organic compounds in the first fluid material sample and (2) (A) calculating a ratio of the amounts of the corresponding at least 2 organic compounds of the 2-9 organic compounds in the second solid material sample or (B) calculating a ratio of the amounts of the corresponding at least 2 organic compounds of the 2-9 organic compounds in the one or more additional solid material samples, and (3) comparing the calculated ratios derived from the first fluid material sample to the calculated ratios derived from the second solid material sample or the one or more additional solid material samples to estimate the oil producing capabilities of one or more locations from which the second solid material sample or the one or more additional solid material samples were collected.

7. The method of claim 2, wherein the first fluid material sample is a produced oil and the second solid material sample consists of drill cuttings and, if applicable, at least most of the one or more additional solid material samples consist of drill cuttings.

8. The method of claim 2, wherein the first fluid material sample, the second solid material sample, and the one or more additional solid material samples, if applicable, are collected from a single oil well within the geologic unit.

9. The method of claim 8, wherein the method comprises (a) dividing the oil well from which the first fluid material sample and the one or more additional solid material samples, if applicable, are collected into zones and (b) providing a scaling factor for each of the solid material samples analyzed according to the zone's spatial contribution to the overall length of the oil well from which the solid material samples were collected.

10. The method of claim 9, wherein only zones associated with locations of the oil well open to an influx of fluid are considered in determining the relative contributions of each zone of the oil well.

11. The method of claim 2, wherein the first fluid material sample is collected from an oil well in the geologic unit, and the second solid material sample and any of the one or more additional solid material samples, if applicable, are collected from one or more other locations within the geologic unit that are in fluid communication with the oil well.

12. The method of claim 2, wherein the 1-9 organic compounds in the first fluid material sample comprise one or more C4-C11 hydrocarbons, the 1-9 organic compounds in the second solid material sample comprise one or more corresponding C4-C11 hydrocarbons, and, if applicable, the 1-9 organic compounds present in the one or more additional solid material samples comprise one or more corresponding C4-C11 hydrocarbons.

13. The method of claim 12, wherein the 1-9 organic compounds in the first fluid material sample comprise one or more C5-C10 hydrocarbons, the 1-9 organic compounds in the second solid material sample comprise one or more corresponding C5-C10 hydrocarbons, and if applicable, the 1-9 organic compounds in the one or more additional solid material samples comprise one or more corresponding C5-C10 hydrocarbons.

14. The method of claim 13, wherein at least 50% of the C5-C10 hydrocarbons in the 1-9 organic compounds consist of alkane or cycloalkyl compounds.

15. The method of claim 14, wherein the first fluid material sample is collected from an oil well, and wherein the method comprises calculating one or more ratios of the amount of one or more alkane compounds to the sum of the alkane compounds and one or more cycloalkane compounds in (1) the first fluid material sample and (2) the second solid material sample, or, if applicable, any of the one or more additional solid material samples, wherein more similarity between the calculated ratios of the amount of alkane compounds to the sum of the amount of alkane compounds and the amount of cycloalkane compounds in the first fluid material sample and the ratio of the amount of alkane compounds to the sum of the amount of alkane compounds and the amount of cycloalkane compounds in, as applicable, (a) the second solid material sample or (b) any of the one or more additional solid material samples is indicative of fluid associated with the fluid sample originating from the solid sample location from which the solid material sample having the more similar ratio was collected.

16. The method of claim 2, wherein the method comprises using the evaluation step of the method to select one or more locations for (a) drilling a new lateral or vertical well, (b) directing drilling operations on an existing lateral or vertical well, (c) fracking an existing well, or (d) performing any combination of (a)-(c).

17. The method of claim 2, wherein the second solid material sample and any of the one or more additional solid material samples are subjected to an analysis that identifies an amount of each of 2-9 organic compounds of the 1-9 organic compounds present in the first fluid material sample wherein (a) each of the 2-9 organic compounds have the same number of carbon atoms as one another; (b) each of the 2-9 organic compounds have at least five covalently-bonded carbon atoms; (c) the difference in the number of carbon atoms between any of the 2-9 organic compounds is no greater than 2; or (d) any combination of some or all of (a)-(c) is true.

18. The method of claim 2, wherein the first fluid material sample comprises a produced condensate.

19. The method of claim 2, wherein the determination in step (d) of the method comprises determining whether at least 75% of the first fluid material sample originates from the solid sample location and steps (e) and (f) of the method are only performed in the event the result of the evaluation in step (c) does not indicate that at least 75% of the first fluid material sample originates from the source from which the second solid material sample was collected.

20. The method of claim 19, wherein the determination in step (d) of the method comprises determining whether at least 95% of the first fluid material sample originates from the solid sample location and steps (e) and (f) of the method are only performed in the event the result of the evaluation in step (c) does not indicate that at least 95% of the first fluid material sample originates from the source from which the second solid material sample was collected.

21. A method of identifying a highly contributing source of produced hydrocarbon liquid samples comprising:

(a) analyzing the amount of each of 1-9 organic compounds present in a first fluid material sample by subjecting the first fluid material sample to a process that determines the amount of each of the 1-9 organic compounds in the first fluid material sample;

(b) analyzing the amount of each of 1-9 organic compounds present in a second fluid material sample, wherein each of the 1-9 organic compounds analyzed in the second fluid material sample are identified as corresponding to one of the 1-9 organic compounds in the first fluid material sample by (1) having the same composition and structure as one of the 1-9 organic compounds analyzed in the first fluid material sample or (2) being carbon-compositionally similar and structurally similar to one of the 1-9 organic compounds in the first fluid material sample, by subjecting the second fluid material sample to a process that determines the amount of each of the 1-9 organic compounds present in the second fluid material sample;

(c) comparing the amount of each of the 1-9 organic compounds in the first fluid material sample to the amount of each of the corresponding 1-9 organic compounds in the second fluid material sample, wherein a greater amount of each of the corresponding 1-9 organic compounds in the second fluid material sample with respect to the 1-9 organic compounds in the first fluid material sample increases the likelihood that the first fluid material sample and the second fluid material sample originate from the same source;

(d) determining from the comparison performed in step (c) whether at least 50% of the first fluid material sample originates from a source from which the second fluid material sample was collected;

(e) if the result of the evaluation in step (c) does not indicate that at least 50% of the first fluid material sample originates from the same source as the second fluid material sample, determining the amount of each of 1-9 organic compounds in one or more additional fluid material samples, each of the 1-9 organic compounds in each of the one or more additional fluid material samples identified as corresponding to an organic compound of the 1-9 organic compounds in the first fluid material sample by (1) having the same composition and structure as one of the 1-9 organic compounds in the first fluid material sample or (2) being carbon-compositionally similar and structurally similar to one of the 1-9 organic compounds in the first fluid material sample, by subjecting the one or more additional fluid material samples to a process that determines the amount of each of the 1-9 organic compounds present in the one or more additional fluid material samples;

(f) if step (e) of the method is performed, evaluating a likelihood of the first fluid material sample and the one or more additional fluid material samples originating from a same source by comparing the amount of each of the 1-9 organic compounds in the first fluid material sample to the amount of each of the corresponding 1-9 organic compounds in the one or more additional fluid material samples; and (g) providing a direction to perform oil drilling operations, fracking operations, or both, at one or more locations associated with the second fluid material sample or the one or more additional fluid material samples, and which are identified by the other steps of the method as having contributed an amount of the 1-9 organic compounds to the first fluid material sample.

22. The method of claim 21, wherein the method comprises calculating one or more ratios of the amount of one or more alkane compounds to the sum of the amount of the alkane compounds and the amount of one or more cycloalkane compounds in (1) the first fluid material sample and (2) (A) the second fluid material sample or (B) the one or more additional fluid material samples, wherein more similarity between the one or more calculated ratios of the amount of the alkane compounds to the sum of the amount of the alkane compounds and the cycloalkane compounds in the first fluid material sample and the ratio of the amount of the alkane compounds to the sum of the amount of the alkane compounds and the cycloalkane compounds in (a) the second fluid material sample or the one or more additional fluid material samples is indicative of fluid associated with the more similar ratio originating from the same source as the first fluid material sample.

23. The method of claim 21, wherein the method comprises using the amounts of organic compounds measured in the method to select one or more locations for (a) drilling a new lateral or vertical oil well, (b) directing drilling operations on an existing lateral or vertical oil well, (c) fracking an existing oil well, or (d) performing any combination of (a)-(c).

24. The method of claim 21, wherein the method further comprises (1) calculating a ratio of the amounts of at least 2 organic compounds of the 1-9 organic compounds present in the first fluid material sample, (2) (A) calculating a ratio of the amounts of at least 2 corresponding organic compounds in the second fluid material sample or (B) calculating a ratio of the amounts of at least 2 corresponding organic compounds of the 1-9 organic compounds present in any of the one or more additional fluid material samples, and (3) comparing the calculated ratios of the at least 2 organic compounds derived from the first fluid material sample to the calculated ratios of the at least 2 organic compounds derived from (A) the second fluid material sample or (B) any of the one or more additional fluid material samples.

25. The method of claim 21, wherein the method further comprises:

(h) each of the 1-9 organic compounds present in the first fluid material sample is selected from a group of less than 120 possible organic compounds; and (i) (1) at least 95% of the second fluid material sample is composed of a fluid originating from a location known to be or known to have been in contact with at least one part of the geologic unit within which the oil well has been placed under conditions permitting the flow of a quantifiable amount of oil-associated compounds into the second fluid material sample or (2) at least 95% of any of the one or more additional fluid material samples is composed of a fluid originating from one or more locations that are or have been in contact with at least one part of the geologic unit within which the oil well has been placed under conditions permitting the flow of a quantifiable amount of oil-associated compounds into the one or more additional fluid material samples.

26. The method of claim 25, wherein the first fluid material sample comprises a produced condensate.

27. The method of claim 26, wherein the steps of the method comprises subjecting all of the fluid material samples analyzed in the method to a process that determines the amount of at least one organic compound in all of the fluid material samples, the process comprising subjecting all the fluid material samples to a negative pressure of $1\times10^{-2}$ millibars or less applied at about room temperature for about 3 minutes to about 30 minutes.

28. The method of claim 21, wherein the determination in step (d) of the method comprises determining whether at least 75% of the first fluid material sample originates from the source from which the second fluid material sample was collected and steps (e) and (f) of the method are only performed in the event the result of the evaluation in step (c) does not indicate that at least 75% of the first fluid material sample originates from the source from which the second fluid material sample was collected.

29. The method of claim 28, wherein the determination in step (d) of the method comprises determining whether at least 95% of the first fluid material sample originates from the source from which the second fluid material sample was collected and steps (e) and (f) of the method are only performed in the event the result of the evaluation in step (c) does not indicate that at least 95% of the first fluid material sample originates from the source from which the second fluid material sample was collected.

* * * * *